US011644467B2

(12) United States Patent
Rimm et al.

(10) Patent No.: US 11,644,467 B2
(45) Date of Patent: May 9, 2023

(54) PREDICTION OF RESPONSE TO IMMUNE-MODULATORY THERAPIES

(71) Applicant: YALE UNIVERSITY, New Haven, CT (US)

(72) Inventors: David L. Rimm, Branford, CT (US); Kurt Schalper, Branford, CT (US)

(73) Assignee: YALE UNIVERSITY, New Haven, CT (US)

( * ) Notice: Subject to any disclaimer, the term of this patent is extended or adjusted under 35 U.S.C. 154(b) by 807 days.

(21) Appl. No.: 16/464,010

(22) PCT Filed: Nov. 30, 2017

(86) PCT No.: PCT/US2017/063986
§ 371 (c)(1),
(2) Date: May 24, 2019

(87) PCT Pub. No.: WO2018/102567
PCT Pub. Date: Jun. 7, 2018

(65) Prior Publication Data
US 2020/0386760 A1 Dec. 10, 2020

Related U.S. Application Data

(60) Provisional application No. 62/428,923, filed on Dec. 1, 2016.

(51) Int. Cl.
G01N 33/574 (2006.01)
C07K 16/28 (2006.01)
(52) U.S. Cl.
CPC ... G01N 33/57423 (2013.01); C07K 16/2818 (2013.01); G01N 2333/4739 (2013.01);
(Continued)

(58) Field of Classification Search
CPC ..... G01N 33/57423; G01N 2333/4739; G01N 2333/7051; G01N 2333/70514; G01N 2333/70517; G01N 2333/70589; G01N 2333/96436; G01N 2800/52; G01N 2333/96433; G01N 33/505;
(Continued)

(56) References Cited

U.S. PATENT DOCUMENTS

2013/0330325 A1* 12/2013 Grabe ................. G01N 33/574
435/7.1
2014/0086932 A1 3/2014 Traber et al.

OTHER PUBLICATIONS

Tumeh, et al., "PD-1 blockade induces responses by inhibiting adaptive immune response," Nature, Accessed via HHS Public Access, vol. 515, Iss. 7528, pp. 568-571, Nov. 27, 2014, doi:10.1038/nature13954. (Year: 2014).*

(Continued)

Primary Examiner — Jennifer Wecker
Assistant Examiner — Michael Paul Shimek
(74) Attorney, Agent, or Firm — Saul Ewing Arnstein & Lehr LLP; Kathryn Doyle; Justin W. Crotty

(57) ABSTRACT

The present disclosure provides a method of treating cancer by immune checkpoint blockade, or selecting patients for treatment with immune checkpoint blockers, by detecting tumors with high levels of T-lymphocytes with low levels of activation and proliferation. In various embodiments the tissue sample may be from a conventional biopsy. In various embodiments the cancer may be non-small cell lung cancer.

22 Claims, 45 Drawing Sheets

(52) U.S. Cl.
CPC ........... *G01N 2333/7051* (2013.01); *G01N 2333/70514* (2013.01); *G01N 2333/70517* (2013.01); *G01N 2333/70589* (2013.01); *G01N 2333/96436* (2013.01); *G01N 2800/52* (2013.01)

(58) Field of Classification Search
CPC ........... G01N 33/6875; C07K 16/2818; A61K 2039/505; A61K 39/395
See application file for complete search history.

(56) References Cited

OTHER PUBLICATIONS

International Search Report and Written Opinion for PCT International Application No. PCT/US2017/063986 dated Feb. 9, 2018.
Poster and Oral presentation of the concept and supporting data at the Santa Monica Targeted Therapies of Lung Cancer Meeting, Feb. 17, 2016.
Gettinger, et al., "A dormant TIL phenotype defines non-small cell lung carcinomas sensitive to immune checkpoint blockers", Nat Commun. 9(1), Aug. 2018, 3196.
Tumeh, et al., "PD-1 blockade induces responses by inhibiting adaptive immune resistance", Nature 515(7528), Nov. 2014, 568-571.

\* cited by examiner

| Target gene & predicted peptides | | | Mutant HLA typing and predicted binding affinity (nM) | | | | | |
|---|---|---|---|---|---|---|---|---|
| Genes | Mut_Peptide | WT_Peptide | A0201 | A2402 | B0702 | B3502 | C0401 | C0702 |
| MYO1G | HLFSINIVERA | HLFSICIVERA | 61.04 | 36141.06 | 24882.07 | 20341.60 | 14722.66 | 7169.76 |
| TMOD4 | IKIMCDIAAIL | [E]KMCDIAAIL | 34.21 | 9919.14 | 19191.6 | 17018.25 | 14013 | 4382.3 |
| TENM2 | VQLQDIEWWL | VQLQDISWWL | 81.75 | 2134.13 | 26982.58 | 10054.75 | 14852.45 | 3398.41 |
| GCNT1L1 | TLFGLLG[L] | TLFGLLG[F] | 14.95 | 19022.06 | 22695.73 | 18592.53 | 13517.05 | 5590.21 |
| MDN2 | HLIIACFTCA | HLINIACFTCA | 151.59 | 33685.63 | 19088.06 | 16327.03 | 17985.29 | 23699.6 |
| NID1 | FIQIGYTHYLI | FIHIGYTHYLI | 64.78 | 747.17 | 27278.95 | 14640.2 | 14329.76 | 13315.54 |
| RNOT2 | [K]LREEIHKA | [E]LREEIHKA | 414.31 | 37944.28 | 22695.78 | 41375.47 | 21617.22 | 24614.3 |
| RNOT2 | [K]LREEIMKI | [E]LREEIMKI | 176.24 | 11666.98 | 19088.05 | 37829.49 | 15625.39 | 9047.59 |
| MFSA | TMLIFIESEL | TML[S]IESEL | 102.05 | 13000.15 | 17791.74 | 5996.61 | 14485.65 | 11233.42 |
| ARHGAP9 | LITLINFTSL | LIM]LTNFTSL | 377.91 | 11604.04 | 2889.29 | 6461.57 | 10527.33 | 7247.76 |
| TBXAS1 | RLYGP[V]CGL | RLYGP[L]CGL | 22.32 | 23823.16 | 11385.87 | 29856.23 | 11079.16 | 2042.78 |
| GRM3A | WLNINIKMRV | MLNIDINMYRV | 15.03 | 7733.80 | 17038.15 | 24167.26 | 10027.04 | 6575.26 |
| HSF1 | ALM[Q]EVASL | ALM[R]EVASL | 27.05 | 19400.38 | 8519.79 | 20233.54 | 12117.27 | 4311.75 |
| CSGALNACT2 | [F]MFCDVDI | [L]MFCDVDI | 19.28 | 8950.22 | 21970.93 | 6006.64 | 16493.98 | 6575.26 |
| CUSP20 | KLMGV[D]TVV | KLMGV[E]TVV | 10.02 | 21617.22 | 10997.95 | 22518.93 | 12930.01 | 13070.67 |

FIG. 6A

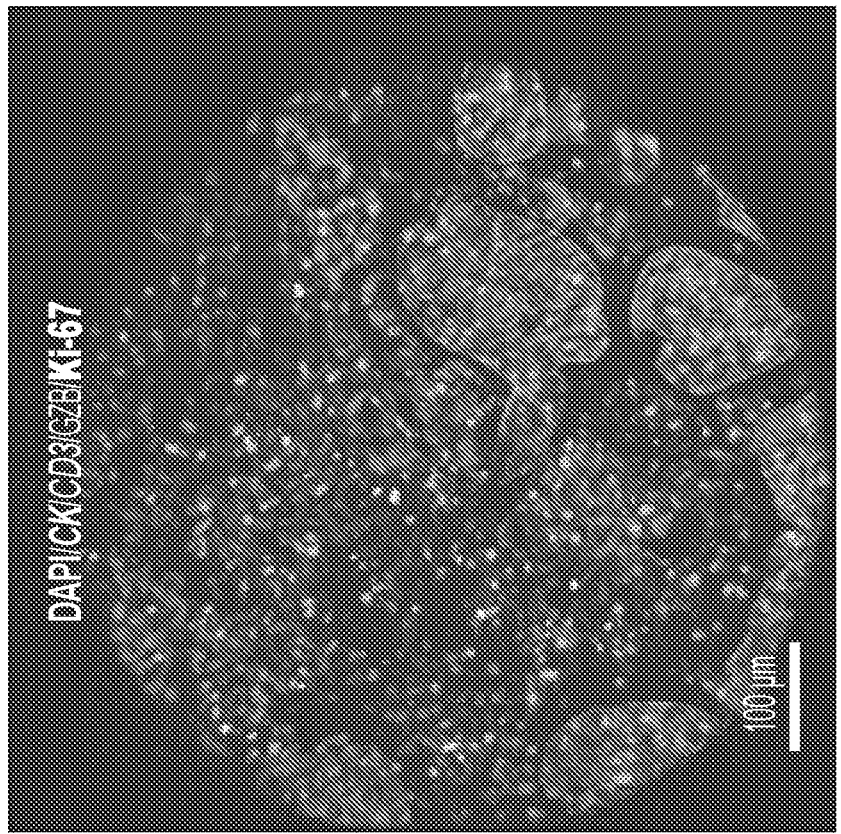
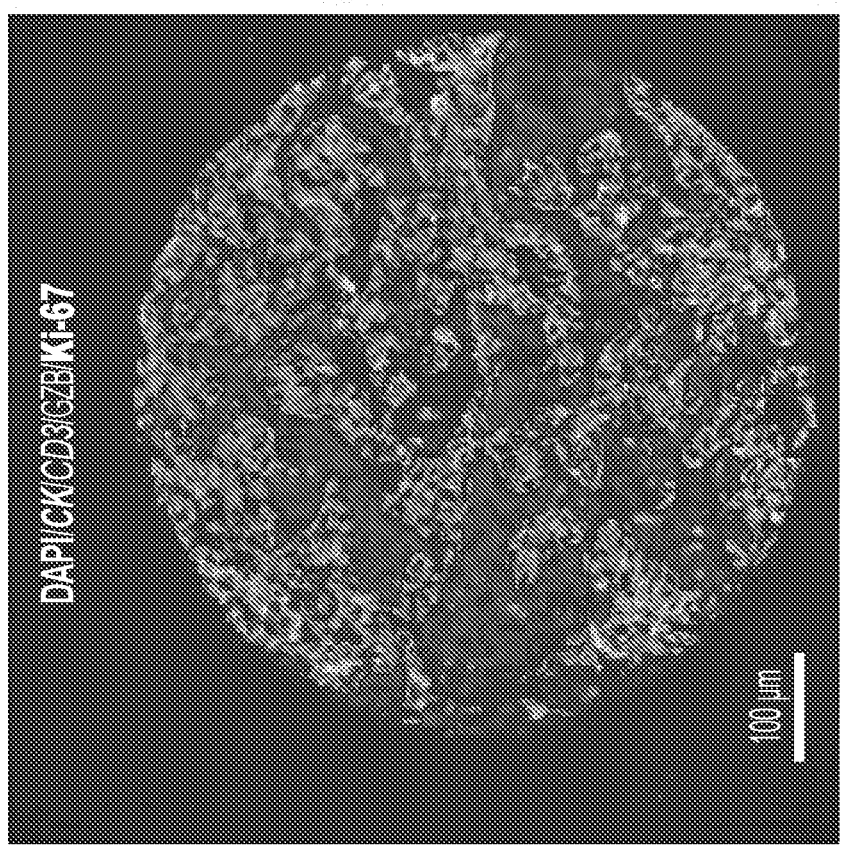
FIG. 9A

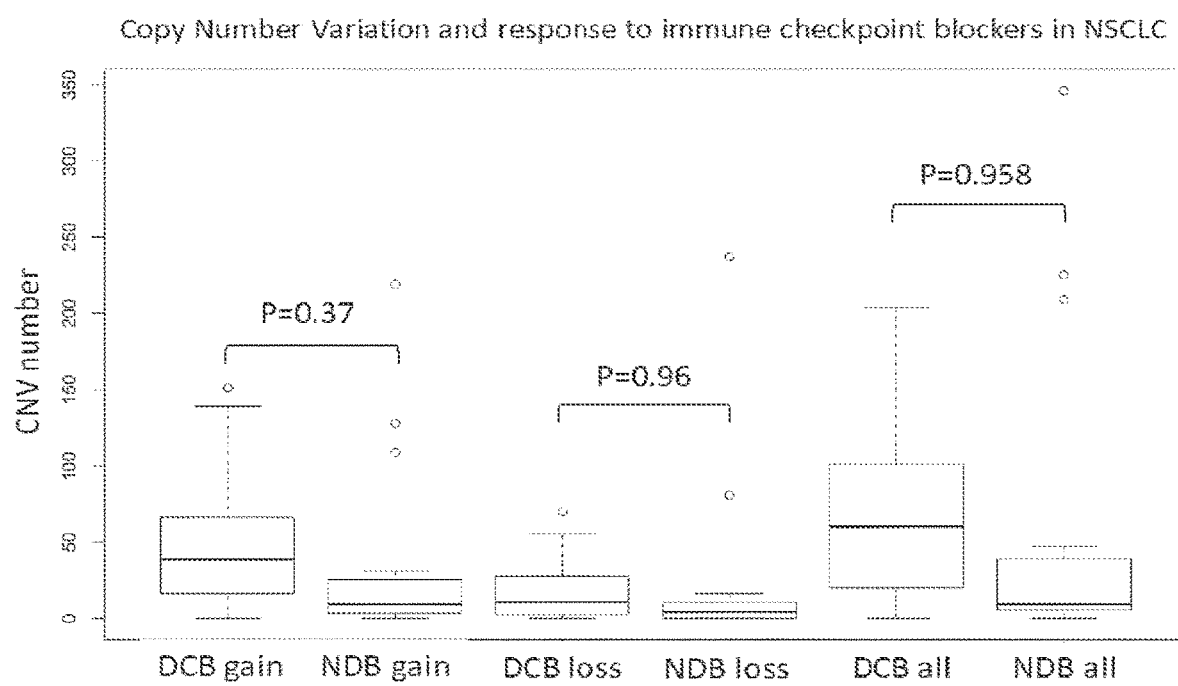

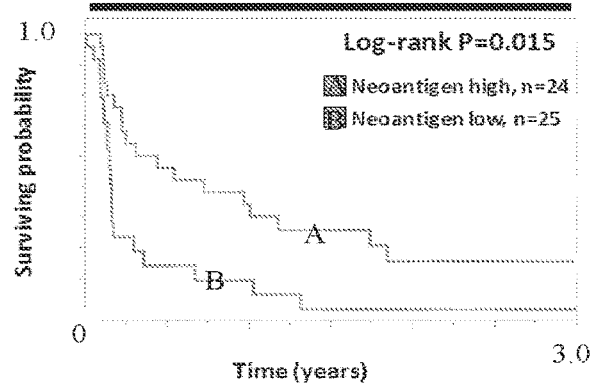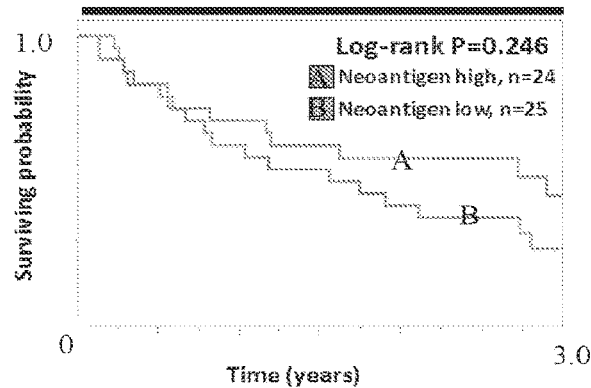
FIG. 16A Progression-free survival
FIG. 16B Overall survival

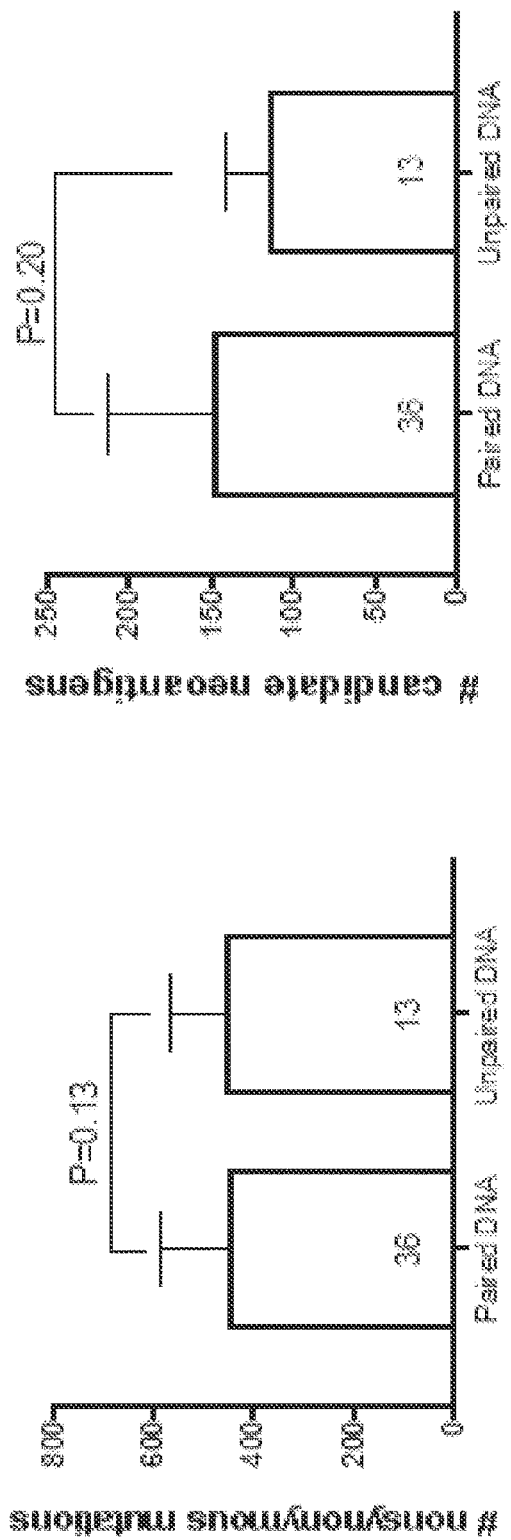
FIG. 20A
FIG. 20B
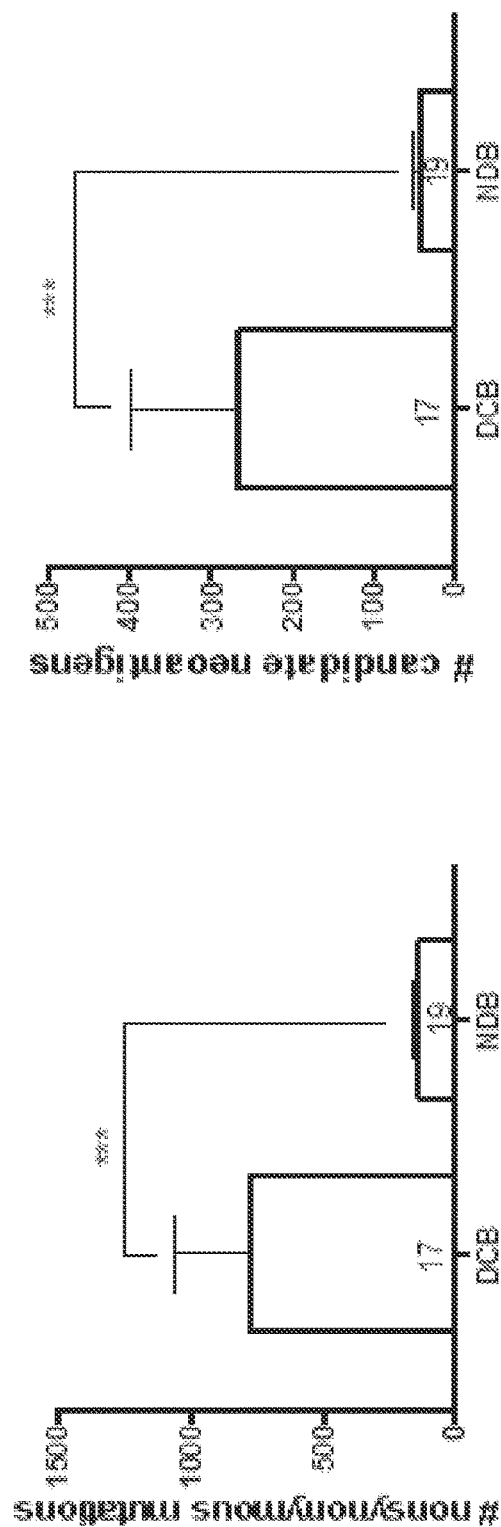
FIG. 20C
FIG. 20D

US 11,644,467 B2

PREDICTION OF RESPONSE TO IMMUNE-MODULATORY THERAPIES

CROSS-REFERENCE TO RELATED APPLICATIONS

The present application is a 35 U.S.C. § 371 national phase application from, and claims priority to, International Application No. PCT/US2017/063986, filed Nov. 30, 2017, and published under PCT Article 21(2) in English, which claims priority under 35 U.S.C. § 119(e) to U.S. Provisional Patent Application No. 62/428,923, filed Dec. 1, 2016, each of which is incorporated herein by reference in its entirety.

STATEMENT REGARDING FEDERALLY SPONSORED RESEARCH OR DEVELOPMENT

This invention was made with government support under Grant No. CA016359 and P50 CA196530 awarded by NIH National Cancer Institute. The government has certain rights in the invention.

BACKGROUND OF THE INVENTION

Immunostimulatory therapies using monoclonal antibodies to block the immune checkpoints PD-1 and CTLA-4 have revolutionized the treatment of diverse tumor types, including lung cancer. Treatment with PD-1 axis blockers induce durable responses in approximately 20% of patients with advanced non-small cell lung cancer (NSCLC). The combination of PD-1 and CTLA-4 blockers induce greater anti-tumor effect than monotherapy regimens in melanoma and is also active in NSCLC. However, the majority of NSCLC patients receiving immune checkpoint blockers do not derive substantial clinical benefit. Therefore, predictive biomarkers to select patients for these therapies are required. In addition, understanding the biological determinants mediating resistance and sensitivity to immune checkpoint blockade could support design of optimal treatment modalities.

Current in situ methods can identify cell type, but not the activity state of immune cells. Determination of activity state requires multiplexed assessment of multiple proteins, sometimes including post-translational modifications to define classifications associated with cellular function. The existing methods to detect immune-related protein biomarkers in tumor samples are usually limited to 1-2 phenotypic cell markers, are subjective and lack quantitative output. In addition, they lack the ability to interrogate specific cellular processes/functions through selective measurement of meaningful markers within the immune cells as defined by multiplexed co-localization.

There is currently no method for assessment of cell function without dissociation or grinding of the sample. A method to capture key information about the quantity and quality of the anti-tumor immune response using a defined combination of carefully selected markers that are measured in situ and with spatial resolution is sorely lacking. There is a need in the art for such a method of assessment. The present disclosure addresses this need.

SUMMARY OF THE INVENTION

In one aspect, the invention provides a method of treating cancer comprising measuring a level of at least one marker for T-lymphocytes, a level of at least one marker for proliferation in the T-lymphocytes and a level of at least one marker for activation in the T-lymphocytes in a tumor tissue sample from a patient, comparing the level of the marker for T-lymphocytes, the level of the marker for activation and the level of the marker for proliferation to corresponding pre-determined reference levels, wherein when the level of the marker for T-lymphocytes is above the corresponding reference level, when the level of the marker for activation is below the corresponding reference level and when the level of the marker for proliferation is below the corresponding reference level, treating the patient with at least one immune checkpoint blocker.

In various embodiments, the marker for T-lymphocytes is CD3, CD8, CD4 or CD45RO.

In various embodiments, the marker for activation is granzyme-B, granzyme-A or perforin.

In various embodiments, the marker for proliferation is ki-67, PCNA or a Cyclin or modified cyclin.

In various embodiments, the level of the markers is measured using quantitative immunofluorescence or quantitative in situ assessment by heavy metal tags, nucleic acid tags or bar-codes.

In various embodiments, the tumor tissue is a formalin-fixed paraffin embedded sample from a conventional biopsy.

In various embodiments, the cancer is blastoma, carcinoma, lymphoma, melanoma, myeloma, sarcoma or germ cell tumor.

In various embodiments, the cancer is non-small cell lung cancer or melanoma.

In various embodiments, the immune checkpoint blocker comprises a PD-1 inhibitor or a CTLA4 inhibitor.

In various embodiments, the PD-1 inhibitor is atezolizumab, avelumab, durvalumab, nivolumab or pembrolizumab.

In various embodiments, the CTLA4 inhibitor is ipilimumab or tremilumimab.

In another aspect, the invention provides a method of selecting patients for treatment with immune checkpoint blockers comprising measuring a level of at least one marker for T-lymphocytes, a level of at least one marker for proliferation in the T-lymphocytes and a level of at least one marker for activation in the T-lymphocytes in a tumor tissue sample from a patient, comparing the level of the marker for T-lymphocytes, the level of the marker for activation and the level of the marker for proliferation to corresponding pre-determined reference levels, wherein when the level of the marker for T-lymphocytes is above the corresponding reference level, when the level of the marker for activation is below the corresponding reference level and when the level of the marker for proliferation is below the corresponding reference level, the patient is selected for treatment with at least one immune checkpoint blocker.

In various embodiments, the marker for T-lymphocytes is CD3, CD8, CD4 or CD45RO.

In various embodiments, the marker for activation is granzyme-B, granzyme-A or perforin.

In various embodiments, the marker for proliferation is ki-67, PCNA or a cyclin or modified cyclin.

In various embodiments, the level of the markers is measured using quantitative immunofluorescence or quantitative in situ assessment by heavy metal tags, nucleic acid tags or bar-codes.

In various embodiments, the tumor tissue is a formalin-fixed paraffin embedded sample from a conventional biopsy.

In various embodiments, the cancer is blastoma, carcinoma, lymphoma, melanoma, myeloma, sarcoma or germ cell tumor.

In various embodiments, the cancer is non-small cell lung cancer or melanoma.

In various embodiments, the immune checkpoint blocker comprises a PD-1 inhibitor or a CTLA4 inhibitor.

In various embodiments, the PD-1 inhibitor is atezolizumab, avelumab, durvalumab, nivolumab or pembrolizumab.

In various embodiments, the CTLA4 inhibitor is ipilimumab or tremlimumab.

In another aspect, the invention provides a kit comprising reagents for an immunohistochemical assay and written instructions, the written instructions comprising measuring a level of at least one marker for T-lymphocytes in the tumor tissue, a level of at least one marker for proliferation in the T-lymphocytes and a level of at least one marker for activation in the T-lymphocytes in a tumor tissue sample from a patient, comparing the level of the marker for T-lymphocytes, the level of the marker for activation and the level of the marker for proliferation to corresponding predetermined reference levels, wherein when the level of the marker for T-lymphocytes is above the corresponding reference level, when the level of the marker for activation is below the corresponding reference level and when the level of the marker for proliferation is below the corresponding reference level, the patient is selected for treatment with at least one immune checkpoint blocker.

In various embodiments, the marker for T-lymphocytes is CD3, CD8, CD4 or CD45RO.

In various embodiments, the marker for activation is granzyme-B, granzyme-A or perforin.

In various embodiments, the marker for proliferation is ki-67, PCNA or a cyclin or modified cyclin.

In various embodiments, the level of the markers is measured using quantitative immunofluorescence, or quantitative in situ assessment by heavy metal tags, nucleic acid tags or bar-codes.

In various embodiments, the tumor tissue is a formalin-fixed paraffin embedded sample from a conventional biopsy.

In various embodiments, the cancer is blastoma, carcinoma, lymphoma, melanoma, myeloma, sarcoma or germ cell tumor.

In various embodiments, the cancer is non-small cell lung cancer or melanoma.

In various embodiments, the immune checkpoint blocker comprises a PD-1 inhibitor or a CTLA4 inhibitor.

In various embodiments, the PD-1 inhibitor is atezolizumab, avelumab, durvalumab, nivolumab or pembrolizumab.

In various embodiments, the CTLA4 inhibitor is ipilimumab or tremlimumab.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 3A and 3B, together depict patterns of T-cells and benefit from immune checkpoint blockers in NSCLC.

FIG. 3D depicts the association between predicted class-I neoantigens and specific TIL patterns found in lung tumors from patients treated with immune checkpoint blockers. NS=not significant with Mann-Whitney P>0.05.

FIGS. 4A-4E show the association between local T-cell infiltration, activation/proliferation and survival in NSCLC patients not treated with immune checkpoint blockade.

FIG. 5A is a chart showing the number of somatic mutations (upper panel), candidate MHC class-I neoantigens (middle panel) and frequency of specific nucleotide substitution (lower panel); and association with DCB to immune checkpoint blockade (star) in 49 NSCLC cases. The presence of mutations in genes associated with DNA repair is indicated with arrows over each case. The specific variant type is indicated within the chart. FIGS. 5B-5C depict the association between the mutational load (FIG. 5B) and predicted MHC class-I neoantigens (FIG. 5C) with durable clinical benefit (DCB) and non-durable benefit (NDB) to immune checkpoint blockade. The number of cases in each group is indicated in each bar. FIGS. 5D-5E depict the association between the mutational load and 3-year progression-free survival (FIG. 5D) and overall survival (FIG. 5E) after treatment with immune checkpoint blockaders. The median mutational/candidate MHC class-I neoantigen number was used as stratification cut point. The log-rank P value is indicated within each chart.

FIG. 6A-6E depict the experimental validation of predicted MHC class-I neoantigens detected in NSCLC using HLA-A2 peptide stabilization assay. FIG. 6A is a table showing the gene name, mutant neopeptide, wild type peptide sequence and predicted nanomolar affinity for the HLA-A/B/C found in NSCLC samples from a patient with HLA*A2 type over the course of disease. The calculated affinity of the mutant peptides for HLA-A is highlighted. FIG. 6B depicts a representative flow cytometry histogram showing the relative PE-Cy7 fluorescence of surface HLA-A2 in LCL-A2 cells in the control condition or after incubation with recombinant MYO16 mutant neopeptide. FIG. 6C depicts the distribution of stabilization signal scores for each recombinant neopeptide binding to HLA-A2 protein in LCL-174 cells. Scores are expressed a fold change relative to the signal obtained using the negative control. The data presented correspond to neoepitopes identified in 3 different tumor samples from one patient (primary tumor, metastasis and recurrence). Each score obtained in two replicates was averaged and a ratio was calculated respect to the average of two replicates using the negative control peptide. FIG. 6D depicts a histogram showing the association between the predicted nanomolar affinity of each mutant neoantigenic sequence to HLA-A and the actual binding to HLA-A2 in LCL-174 cells. The HLA-A2 signal was measured using flow cytometry as indicated in the methods section. FIG. 6E depicts a histogram showing the association between the predicted nanomolar affinity of each mutant neoantigenic sequence and the non-mutant (wild-type) sequence.

FIG. 7A depicts the association between the mutational load and the level of cigarette smoking in lung cancer patients treated with immune checkpoint blockers. R=Spearman's rho rank correlation coefficient. FIGS. 7B-7C are charts showing the number of nonsynonymous mutations (FIG. 7B) or candidate HLA class-I and class-II neoantigens (FIG. 7C) in lung tumors treated with immune checkpoint blockers harboring mutations in EGFR, KRAS or lacking mutations in both oncogenes. FIG. 7D depicts the frequency of the specific variants identified in NSCLCs with EGFR (left panel) and KRAS mutations (right panel) *=Mann-Whitney P value<0.05; **=Mann-Whitney P value<0.01.

FIG. 8A depicts the distribution of in situ CD3 (left Y axis), T-cell GZB (right Y axis) and T-cell Ki-67 signal (right Y axis) in lung tumors from patients treated with immune checkpoint blockers. FIGS. 8B-8D de[ict the association between the level of CD3 (FIG. 8B), T-cell GZB (FIG. 8C) and T-cell Ki-67 (FIG. 8D) with durable clinical benefit (DCB) or non-durable benefit (NDB) to immune checkpoint blockade. The number of cases in each group is indicated within each bar. NS=not significant with Mann-Whitney P>0.05. *=Mann-Whitney P value<0.05. FIG. 8E depicts representative multiplexed fluorescence pictures showing lung tumors with a type 1 TIL pattern containing low CD3 level (left panel), a type 2 pattern with high CD3 but low T-cell GZB/Ki-67 (center panel); and a type 3 TIL phenotype with high CD3 and elevated T-cell GZB/Ki-67 (right panel). Bar=100 μm. FIGS. 8F-8G depict Kaplan-Meier graphical analysis of 3-year progression free survival (FIG. 8F) and overall survival (FIG. 8G) of lung cancer cases treated with immune checkpoint blockers according to their TIL phenotype panel. The number of cases in each group and the log-rank P value is indicated in the chart.

FIGS. 9A-9D depict the association between local T-cell infiltration, activation/proliferation and survival in NSCLC patients not treated with immune checkpoint blockade. FIG. 9A depicts immunofluorescent staining of a lung tumor with low (left) and high (right) T-cell activation/proliferation. Slides were simultaneously stained with a multiplex QIF panel containing CD3, Ki-67, GZB, DAPI, and cytokeratin. Bar=100 um. FIG. 9B depicts the distribution of in situ CD3 (left Y axis), T-cell GZB (right Y axis) and T-cell Ki-67 signal (right Y axis) in lung tumors from patients not receiving immune checkpoint blockers. FIG. 9C depicts the association between the level of T-cell GZB and T-cell Ki-67 in the cohort. R=Spearman's correlation coefficient. The P value for the correlation is indicated within each chart. FIG. 9D depicts Kaplan-Meier graphical analysis of 5-year overall survival of NSCLC cases not treated with immune checkpoint blockers according to their TIL activation subtypes. A type 1 TIL pattern was with low CD3, a type 2 pattern with high CD3 but low T-cell GZB/Ki-6; and a type 3 TIL phenotype with high CD3 and elevated T-cell GZB/Ki-67. The number of cases in each group and the log-rank P value is indicated in the chart.

FIG. 10A depicts a biaxial plot of Ki-67 vs GZB expression in TILs (CD3+) before engraftment (Pretx) and at the moment of sacrifice (Postx) in control (upper panels) and anti-PD-1 treated (lower panels) tumor-bearing mice. FIG. 10B is a viSNE map of each biaxial plot of Ki-67 vs GZB quadrant. FIG. 10C depicts a series of images in which three subpopulations were clustered using viSNE: CD4, CD8 and γδTCR T cells. Expression profile of each quadrant is depicted in small panels. Numbers indicate the median mass intensity for each marker. Expression of quadrant Ki-67-GZB- was used as a reference.

FIGS. 11A-B) depict the association between the mutational load (FIG. 11A) or predicted class-I neoantigens (FIG. 11B) and specific TIL patterns found in lung tumors from patients treated with immune checkpoint blockers. NS=not significant with Mann-Whitney P>0.05. FIG. 11C depicts a chart showing the level of CD3 (white bars), T-cell GZB (black bars) and T-cell Ki-67 (gray bars) in lung tumors from patients treated with immune checkpoint blockers harboring mutations in EGFR, KRAS or lacking mutations in both oncogenes. *=Mann-Whitney P value<0.05. FIGS. 11D-11F depict the association between the mutational load and the level of CD3 (FIG. 11D), T-cell GZB (FIG. 11E) and T-cell Ki-67 (FIG. 11F) in lung cancer patients treated with immune checkpoint blockers. R=Spearman's correlation coefficient. The P value for the correlation is indicated within each chart.

FIG. 15 depicts the association between copy number gain/loss (CNV) and response to immune checkpoint blockers in NSCLC.

FIGS. 16A and 16B depict the association between the level of candidate MHC-class I neoantigens and progression-free survival (FIG. 16A) and overall survival (FIG. 16B) in NSCLC patients treated with immune checkpoint blockers.

FIGS. 20A-20F depict the association between the mutational load, candidate MHC class-I neoantigens (FIGS. 20A-20D) and outcome (FIGS. 20E and 20F) in NSCLC cases with paired germline/tumor DNA and excluding cases with unpaired DNA samples.

DETAILED DESCRIPTION

Definitions

Figure 1A:
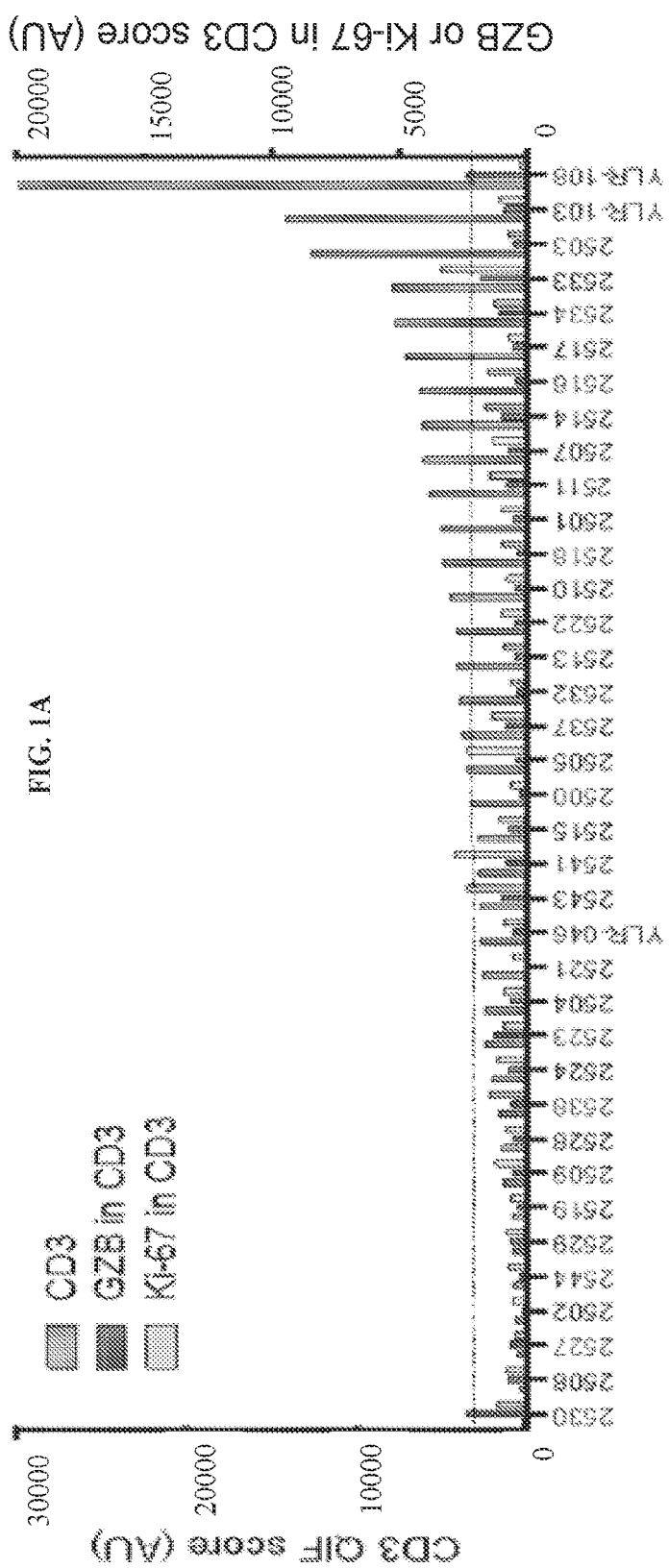
FIG. 1A depicts the distribution of in situ CD3, T-cell granzyme-B and T-cell ki-67 signal in lung tumors from patients treated with immune checkpoint blockers. The dashed black line indicates the median CD3 score.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "biomarker" or "marker," as used herein, refers to a molecule that can be detected. Therefore, a biomarker according to the present invention includes, but is not limited to, a nucleic acid, a polypeptide, a carbohydrate, a lipid, an inorganic molecule, an organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. As defined by the Food and Drug Administration (FDA), a biomarker is a characteristic (e.g. measurable DNA and/or RNA or a protein) that is "objectively measured and evaluated as an indicator of normal biologic processes, pathogenic processes, or pharmacologic responses to a therapeutic intervention or other interventions". Biomarkers also include any calculated indices created mathematically or combinations of any one or more of the foregoing measurements, including temporal trends and differences. Biomarkers may be measured at any level spatial or temporal localization, including but not limited to within a tumor, within in a cell, or on the membrane of a cell.

As used herein, "immune checkpoint blocker" means a biologic or small molecule drug that may trigger an immune reaction by a patient's immune system against cancer cells in the patient's body by targeting an immune checkpoint protein, by way of non-limiting example, PD-1.

As used herein, "immune checkpoint therapy" means the treatment of a patient with at least one immune checkpoint blocker.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The "level" of one or more biomarkers means the absolute or relative amount or concentration of the biomarker in the sample as determined by measuring mRNA, cDNA or protein, or any portion thereof such as oligonucleotide or peptide. A level of a biomarker may refer, based on context, to a global level or a level within some subdivision of an organism, by way of non-limiting example a level may refer to the amount or concentration of a biomarker in a cell, in a particular type of cell, on the cell membrane, in a particular tumor or on the cell membrane of a particular cell type in a particular tumor, in an area delineated by another marker or any other configuration.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "reference level" of a biomarker means a level of a biomarker that is indicative of the presence or absence of a particular phenotype or characteristic. When the level of a biomarker in a subject is above the reference level of the biomarker it is indicative of the presence of, or relatively heightened level of, a particular phenotype or characteristic. When the level of a biomarker in a subject is below the reference level of the biomarker it is indicative of a lack of or relative lack of a particular phenotype or characteristic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Method of Treating Cancer

Without wishing to be limited by theory, a TIL signature has been identified in pre-treatment tumor samples characterized by a dormant phenotype that is prominently associated with clinical benefit from treatment with immune checkpoint blockers. In its various embodiments the invention relates to the unexpected finding that patients with tumors having high levels of T-lymphocytes with low levels of activation and proliferation (the dormant phenotype) respond more favorably to immune checkpoint therapy than other cancer patients. The invention is generally directed to the detection of this phenotype and provision of immune checkpoint therapy to appropriate patients. In one aspect the invention comprises a method of treating cancer by measuring a level of at least one marker of T-lymphocytes in tumor tissue obtained from a patient, a level of at least one marker for proliferation and a level of at least one marker for activation in the T-lymphocytes. Then comparing the level of the marker of T-lymphocytes, the level of the marker for activation and the level of the marker for proliferation to corresponding predetermined reference levels, if the level of the marker for T-lymphocytes is above the corresponding reference level, and if the level of the markers for activation and proliferation are below the corresponding reference levels, providing treatment to patients who are likely to clinically benefit from it.

Various embodiments may be directed to various cancers. Various embodiments comprise the treatment of blastoma, carcinoma, lymphoma, melanoma, myeloma, sarcoma or germ cell tumor. In some embodiments the carcinoma is ovarian cancer, vaginal cancer, cervical cancer, uterine cancer, prostate cancer, anal cancer, rectal cancer, colon cancer, stomach cancer, pancreatic cancer, insulinoma, adenocarcinoma, adenosquamous carcinoma, neuroendocrine tumor, breast cancer, lung cancer, esophageal cancer, oral cancer, brain cancer, medulloblastoma, neuroectodermal tumor, glioma, pituitary cancer, and bone cancer. In some embodiments the lymphoma is small lymphocytic lymphoma, lymphoplasmacytic lymphoma, Waldenstrom macroglobulinemia, splenic marginal zone lymphoma, plasmacytoma, extranodal marginal zone B cell lymphoma, MALT lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, Burkitt lymphoma, B cell chronic lymphocytic lymphoma, classical Hodgkin lymphoma, nodular lymphocyte-predominant Hodgkin lymphoma, adult T cell lymphoma, nasal type extranodal NK/T cell lymphoma, enteropathy-type T cell lymphoma, hepatosplenic T cell lymphoma, blastic NK cell lymphoma, mycosis fungoide, Sezary syndrome, primary cutaneous CD30-positive T cell lympho-proliferative disorders, primary cutaneous anaplastic large cell lymphoma, lymphomatoid papulosis, angioimmunoblastic T cell lymphoma, unspecified peripheral T cell lymphoma, or anaplastic large cell lymphoma. Exemplary forms of classical Hodgkin lymphoma include: nodular sclerosis, mixed cellularity, lymphocyte-rich, and lymphocyte-depleted or not depleted. In some embodiments the sarcoma is Askin's tumor, botryodies, chondrosarcoma, Ewing's-PNET, malignant Hemangioendothelioma, malignant Schwannoma, osteosarcoma or soft tissue sarcomas. Subclasses of soft tissue sarcomas include: alveolar soft part sarcoma, angiosarcoma, cystosarcoma phyllodes, dermatofibrosarcomadesmoid tumor, desmoplastic small round cell tumor, epithelioid sarcomaextraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcomal, lymphosarcoma, malignant fibrous histiocytoma, neurofibrosarcoma, rhabdomyosarcoma, and synovial sarcoma. In some embodiments the melanoma is metastatic melanoma, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma. In some embodiments the cancer may be lung cancer, NSCLC, lung adenocarcinoma, squamous cell carcinoma, or large cell lung cancer.

The corresponding tumor tissue sample may be from any solid tumor. In various embodiments, the tumor tissue may be acquired according to methods of conventional biopsy known in the art. In some embodiments the tumor tissue is formalin-fixed paraffin embedded (FFPE) tumor tissue.

Figure 2A:
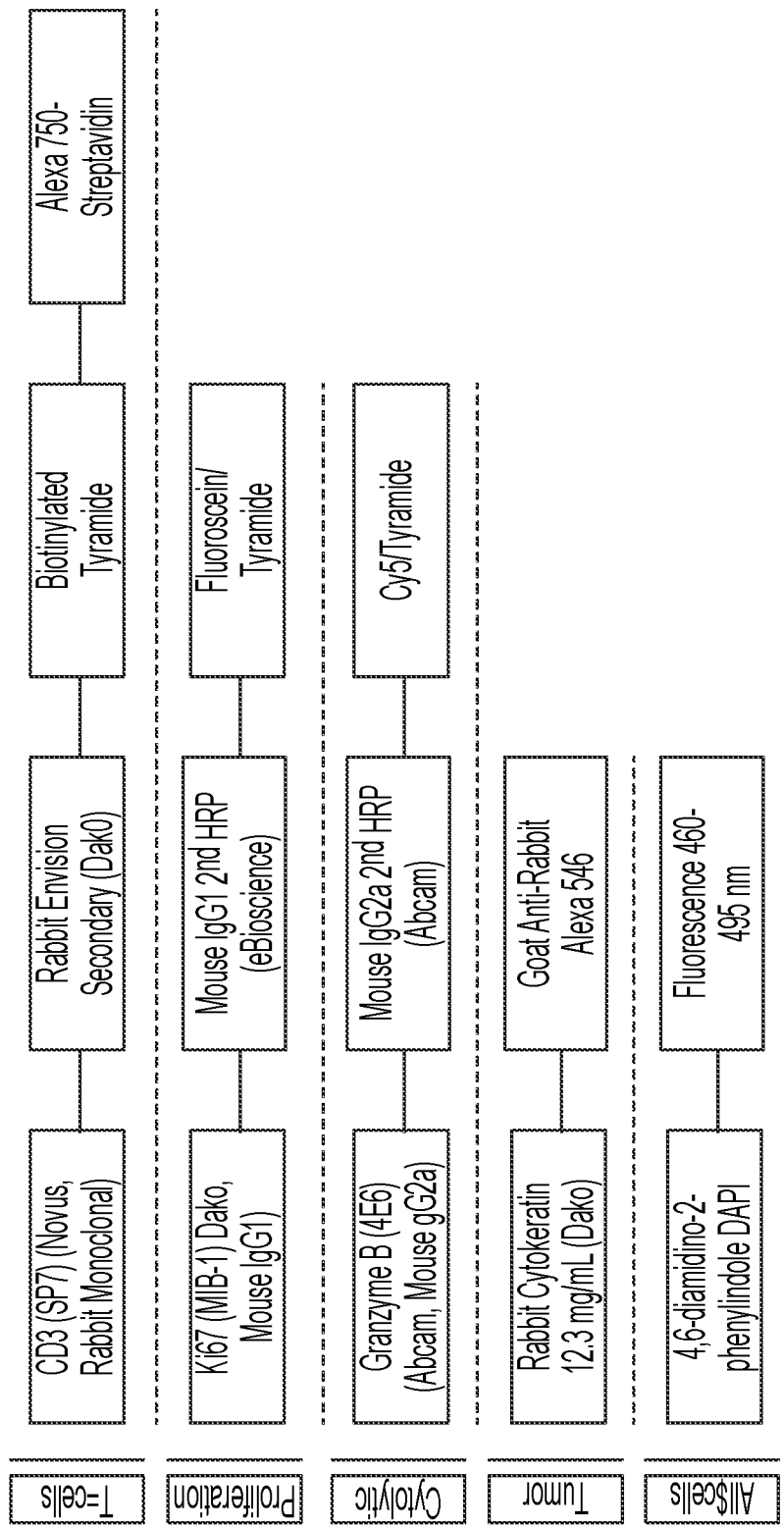
FIG. 2A depicts stains that may be used to detect and/or quantify cells, tumor cells, T-cells, T-cell activation and T-cell proliferation.
Figure 2B:
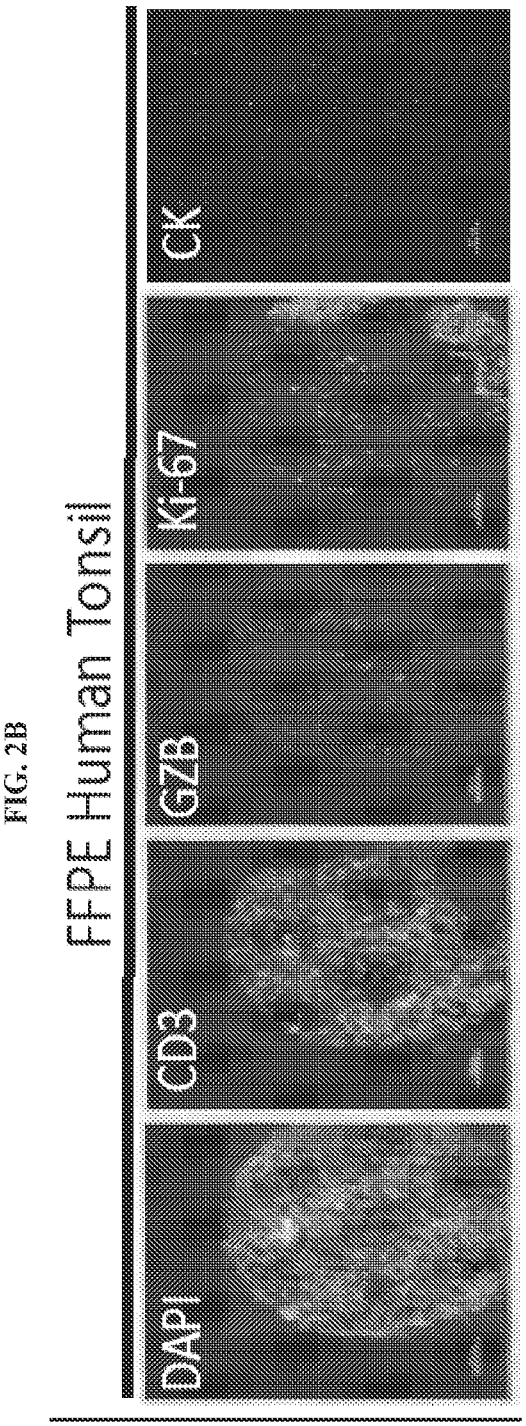
FIG. 2B depicts formalin fixed paraffin embedded human tonsil samples exposed to the stains in FIG. 2A.
Figure 2C:
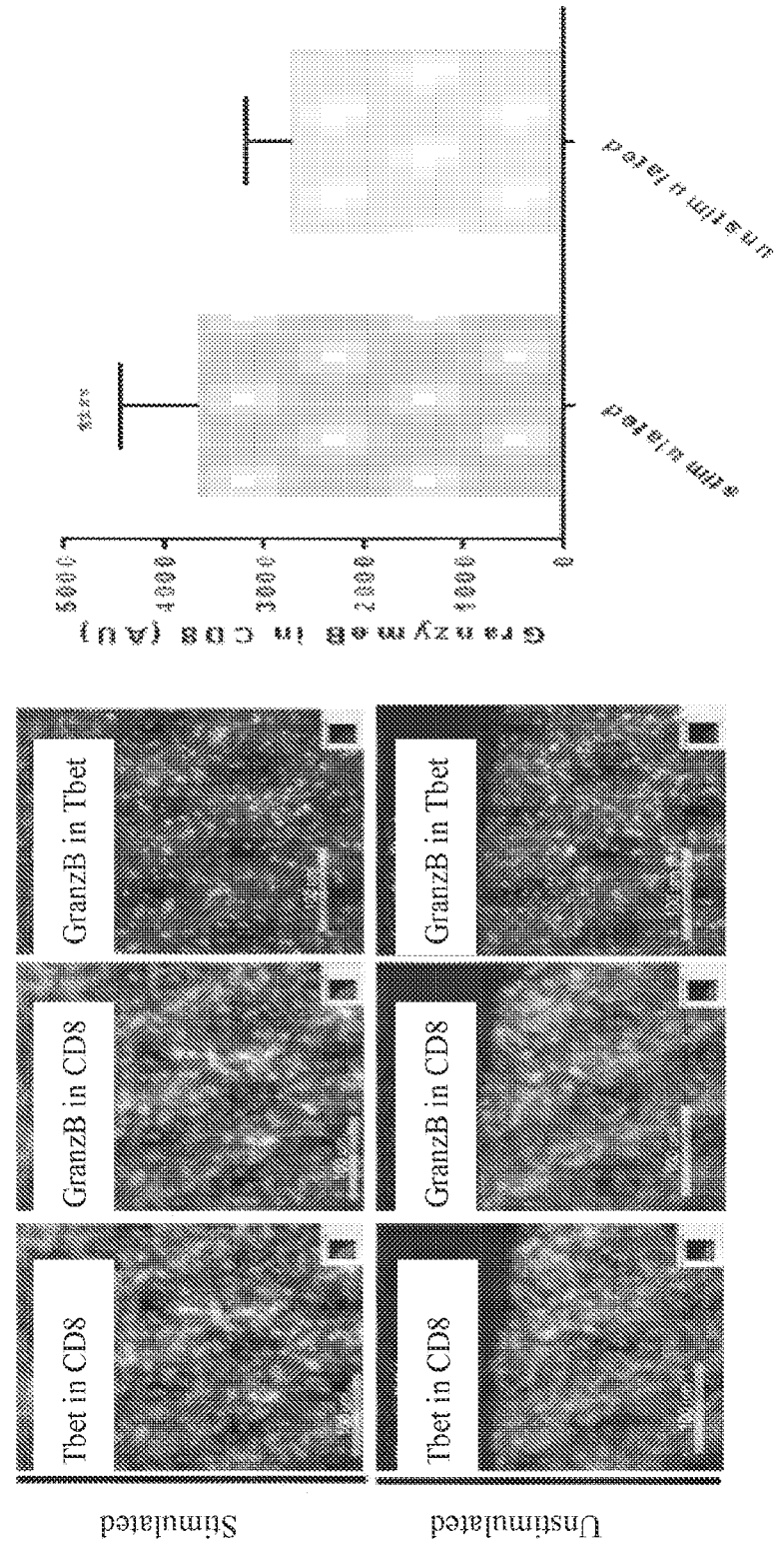
FIG. 2C depicts human peripheral blood mononuclear cells unstimulated or stimulated with CD3/CD28 antibodies; the inset bar graph shows the relative levels of granzyme-B in each group.

In various embodiments, markers are measured within specific compartments defined by the presence of other markers in the sample. The markers may be sequentially or simultaneously stained in slides from tumor tissue using previously validated isotype specific primary antibodies. The methods used to achieve this may include current standard strategies as well as novel methods, such as recombinant antibody labeling, to generate valid multiplexed results. The process may be performed under standard laboratory conditions by personnel using commercial autostainers. After the staining, the slides may be captured using multispectral imaging microscopes to collect the fluorescence intensity of each marker. Commercial software may be used to objectively quantify the fluorescence produced in specific cells or compartments. The result may then be integrated and reported as a metric of the marker amount in specific cell types. In some embodiments the markers may be measured by quantitative immunofluorescence or by quantitative in situ assessment by heavy metal tags, nucleic acid tags or bar-codes, though a skilled artisan will understand that the precise method of measurement may vary and that levels of markers may be quantified using a variety of techniques. FIG. 2 shows the validation of this method using control FFPE preparations of human tonsil, lymph node and unstimulated human peripheral blood mononuclear cells (PBMCs) or PBMCs stimulated with CD3/CD28 antibodies. By integrating key biological readouts with objective target quantification and contextual information it is possible to interrogate the anti-tumor immune response with high sensitivity and reproducibility.

Figure 3A:
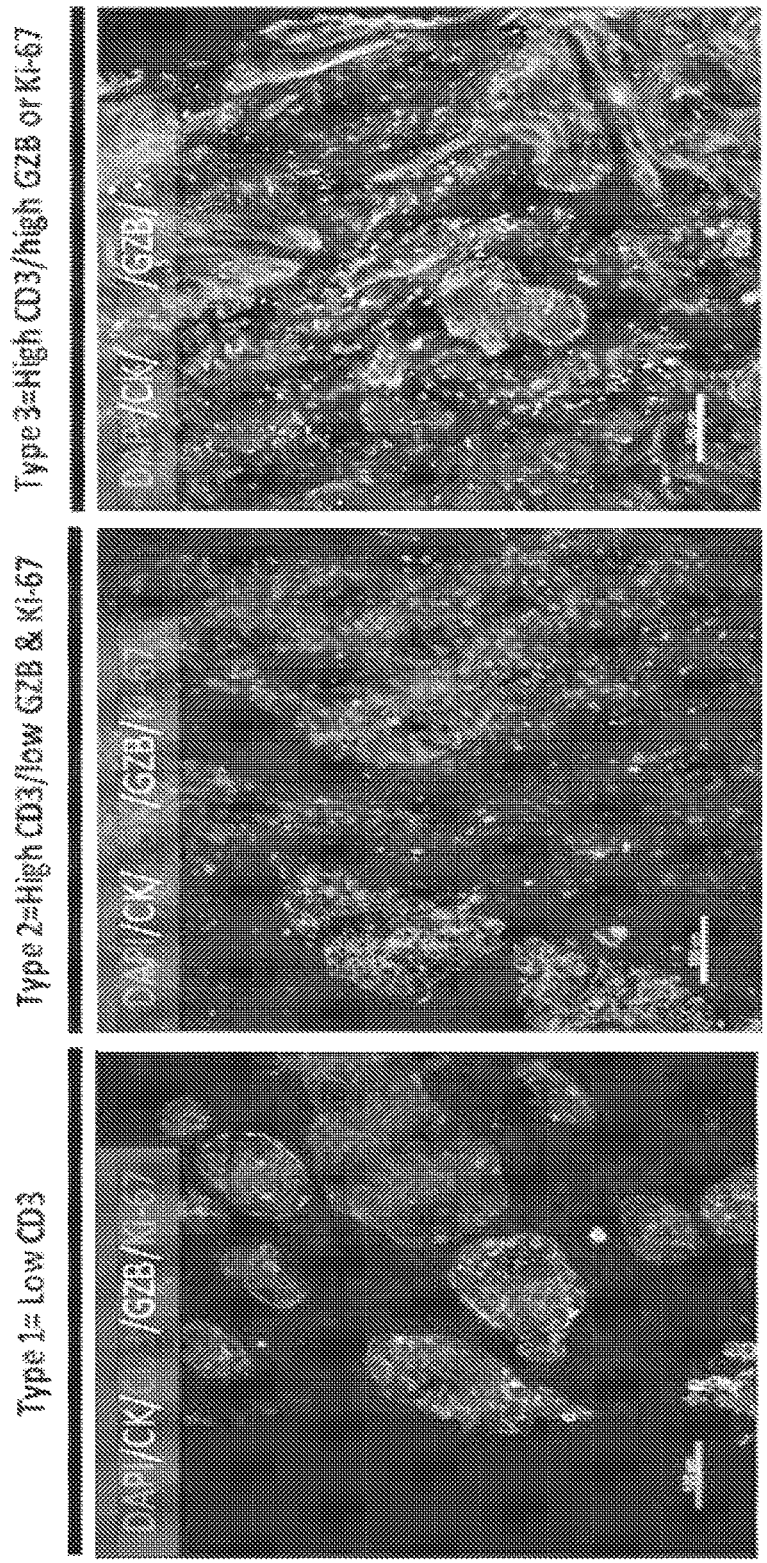
FIG. 3A depicts representative fluorescence pictures showing lung tumors with a type 1 tumor infiltrating lymphocyte (TIL) pattern containing low CD3 level (left panel), a type 2 pattern with high CD3 but low T-cell granzyme-B/ki-67 (center panel); and a type 3 TIL phenotype with high CD3 and elevated T-cell granzyme-B/ki-67 (right panel).
Figure 3B:
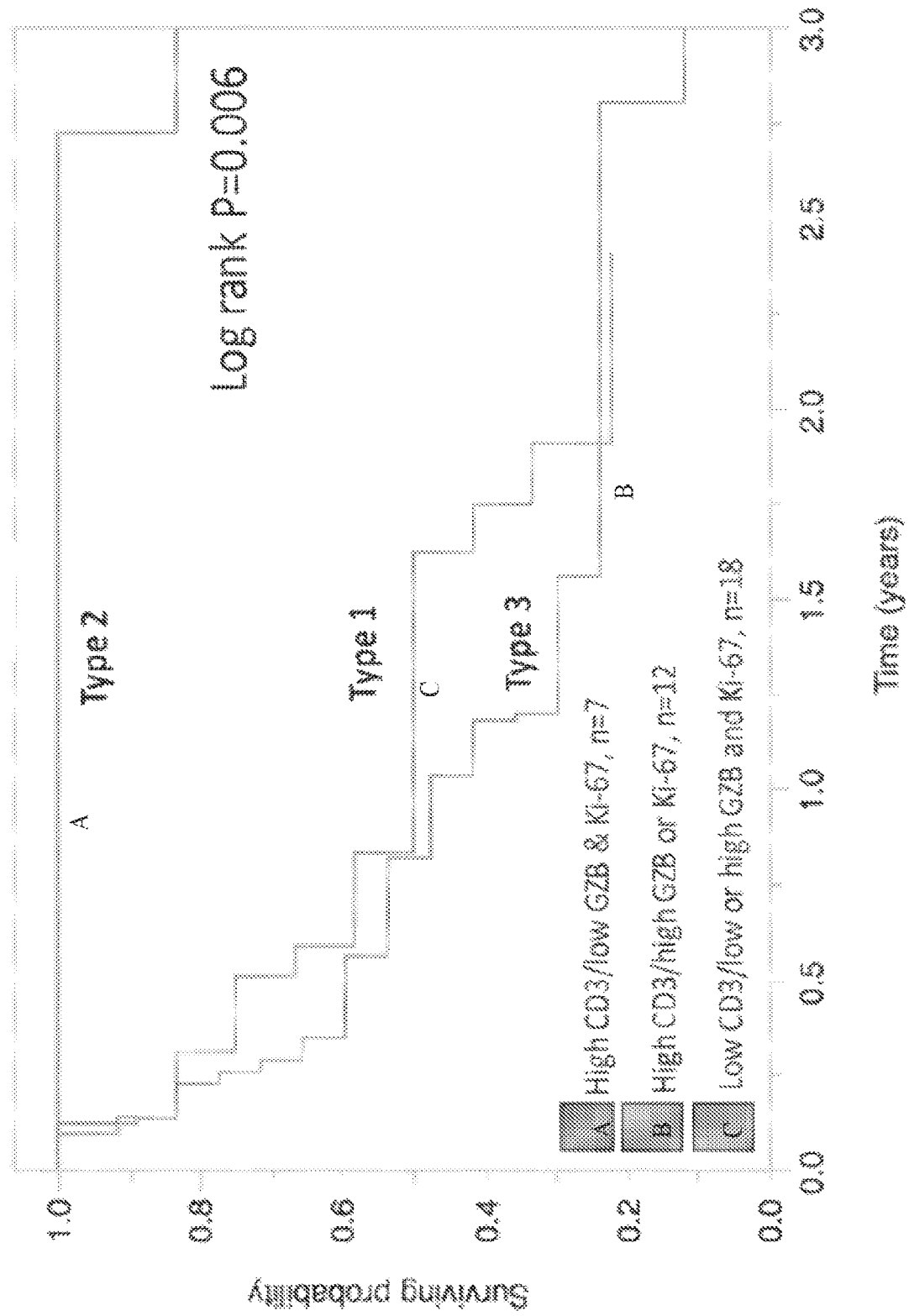
FIG. 3B depicts Kaplan-Meier graphical analysis of 3-year overall survival of lung cancer cases treated with immune checkpoint blockers according to their TIL phenotype panel. The number of cases in each group and the log-rank P value is indicated in the chart.
Figure 3B:
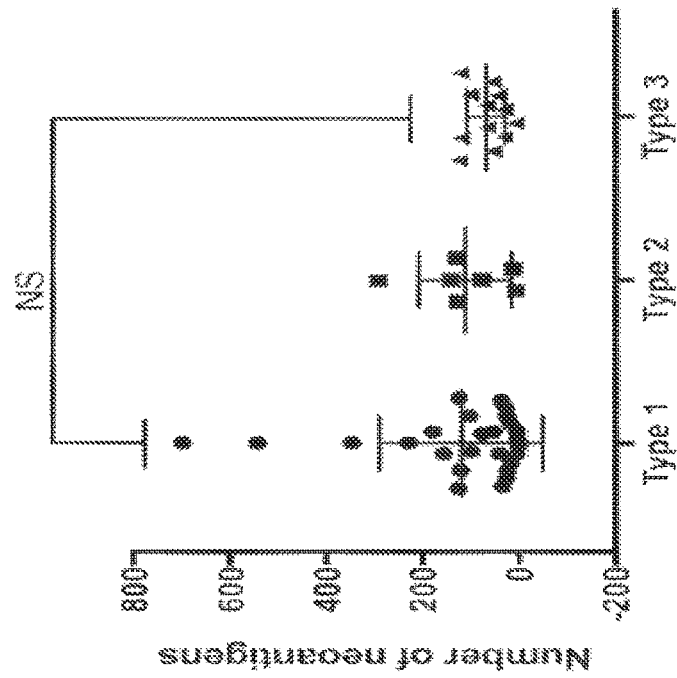

In general embodiments of the invention are not intended to be limited by the markers that may be used to detect and measure levels of T-lymphocytes and levels of activation and proliferation in T-lymphocytes. However, in some embodiments, the marker for T-lymphocytes is CD3, CD8, CD4 or CD45RO, the marker for T-cell activation may be granzyme-B, granzyme-A or perforin and the marker for cell proliferation may be ki-67, PCNA or a Cyclin or modified cyclin. FIG. 3A shows TILs separated into three groups along the axis of tumor infiltration, activation and proliferation by staining for CD3, granzyme-B and ki-67. FIG. 3B illustrates the relationship between the survival of patients treated with immune checkpoint blockers and the three types of TILs as illustrated in 3A. Type 1 patients exhibit low levels of CD3, indicating low levels of T-lymphocytes. Type 2 patients, exhibit high levels of TILs, as measured by staining for CD3, with low levels of activation/proliferation, as measured by staining for granzyme-B and ki-67, respectively. Type 2 patients have substantially higher survival when treated with immune checkpoint therapy than other patients. Type 3 patients exhibit high levels of T-lymphocytes with high levels of activation and proliferation. As shown in FIG. 4, improved prognosis is seen only in patients with high levels of TILs with low levels of activation and proliferation who are treated by immune checkpoint therapy, rather than a general feature of high levels of TILs with low levels of activation/proliferation generally.

Figure 1D:
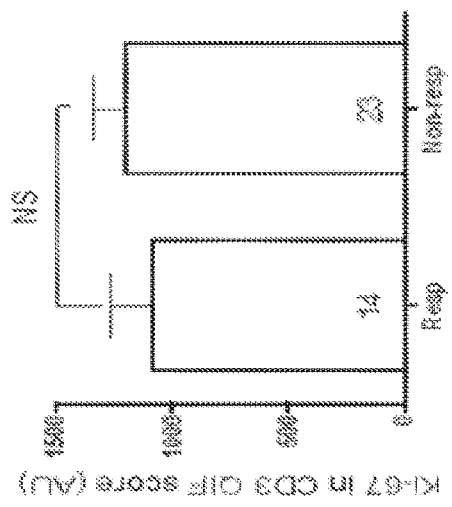
FIG. 1D shows the association between the level of T-cell ki-67 and short-term response to immune checkpoint blockade. For each of FIGS. 1B-D, the number of cases in each group is indicated within each bar. NS=not significant with Mann-Whitney P>0.05.
Figure 1C:
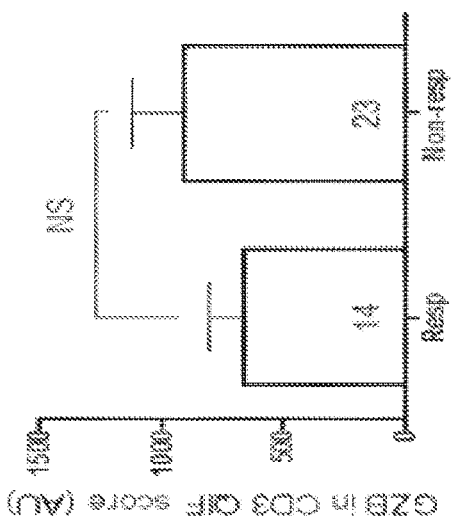
FIG. 1C shows the association between the level of T-cell granzyme-B (GZB) and short-term response to immune checkpoint blockade.
Figure 1B:
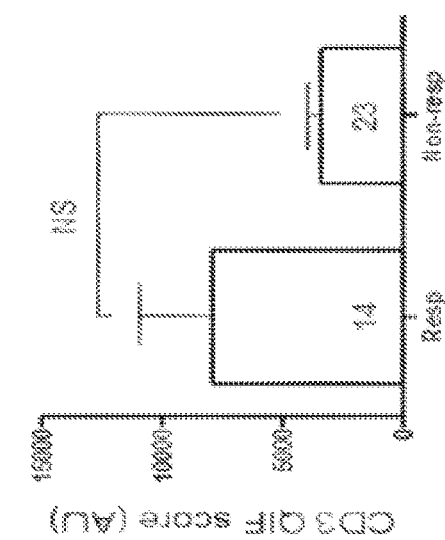
FIG. 1B shows the association between the level of CD3 and short-term response to immune checkpoint blockade.
Figure 1E:
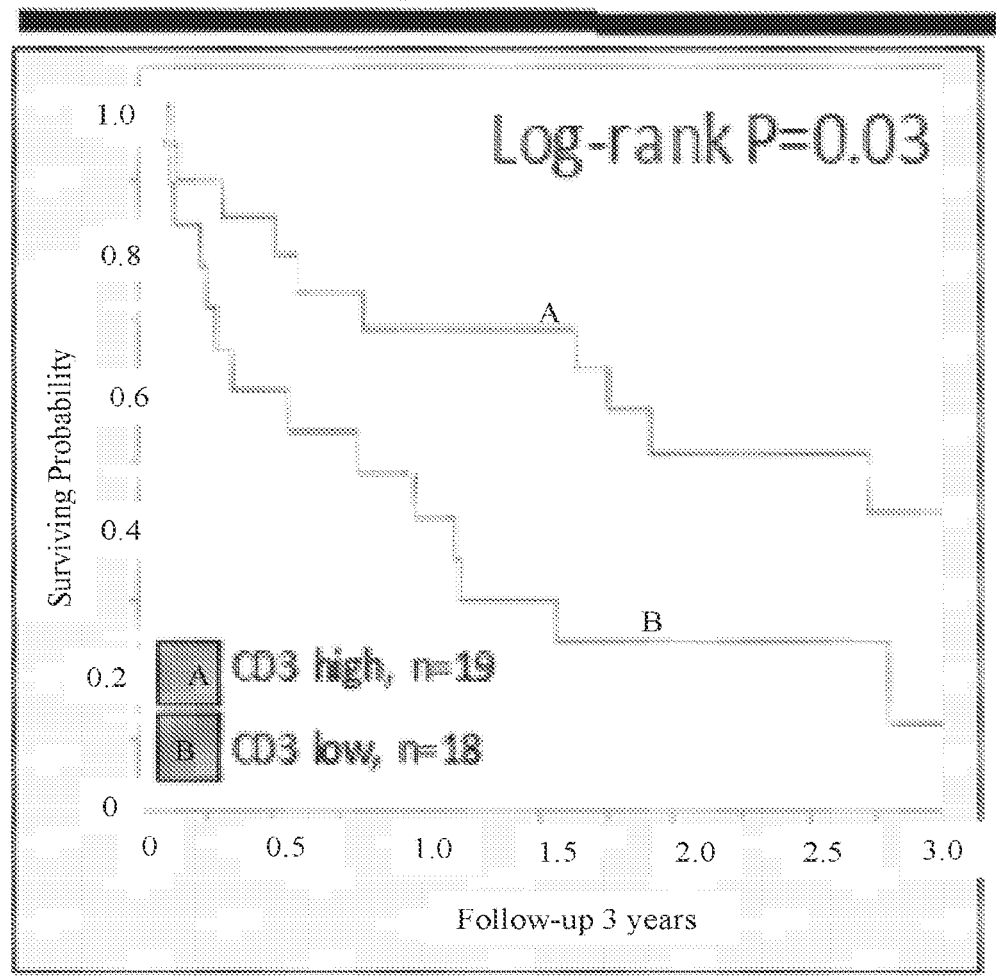
FIG. 1E shows the association between the levels of CD3 and 3-year overall survival after treatment with immune checkpoint blockade.
Figure 1F:
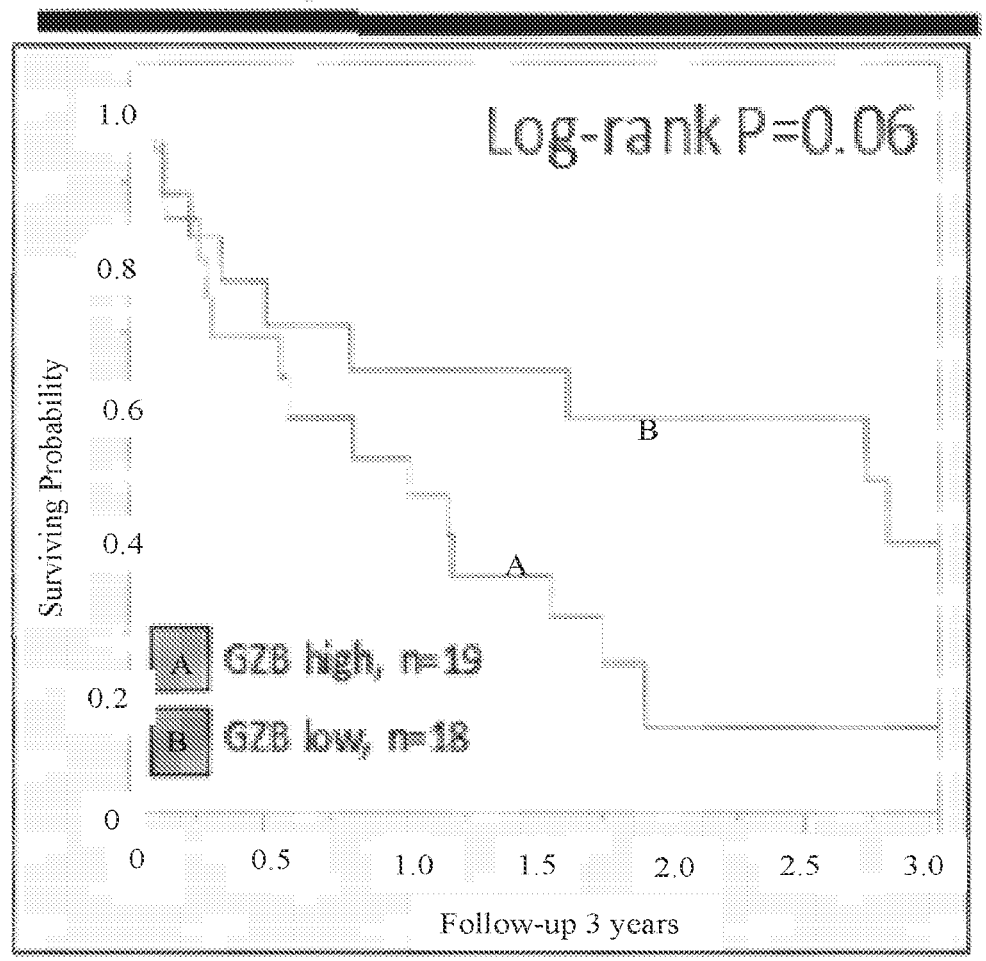
FIG. 1F shows the association between the levels of T-cell granzyme-B and 3-year overall survival after treatment with immune checkpoint blockade.
Figure 1G:
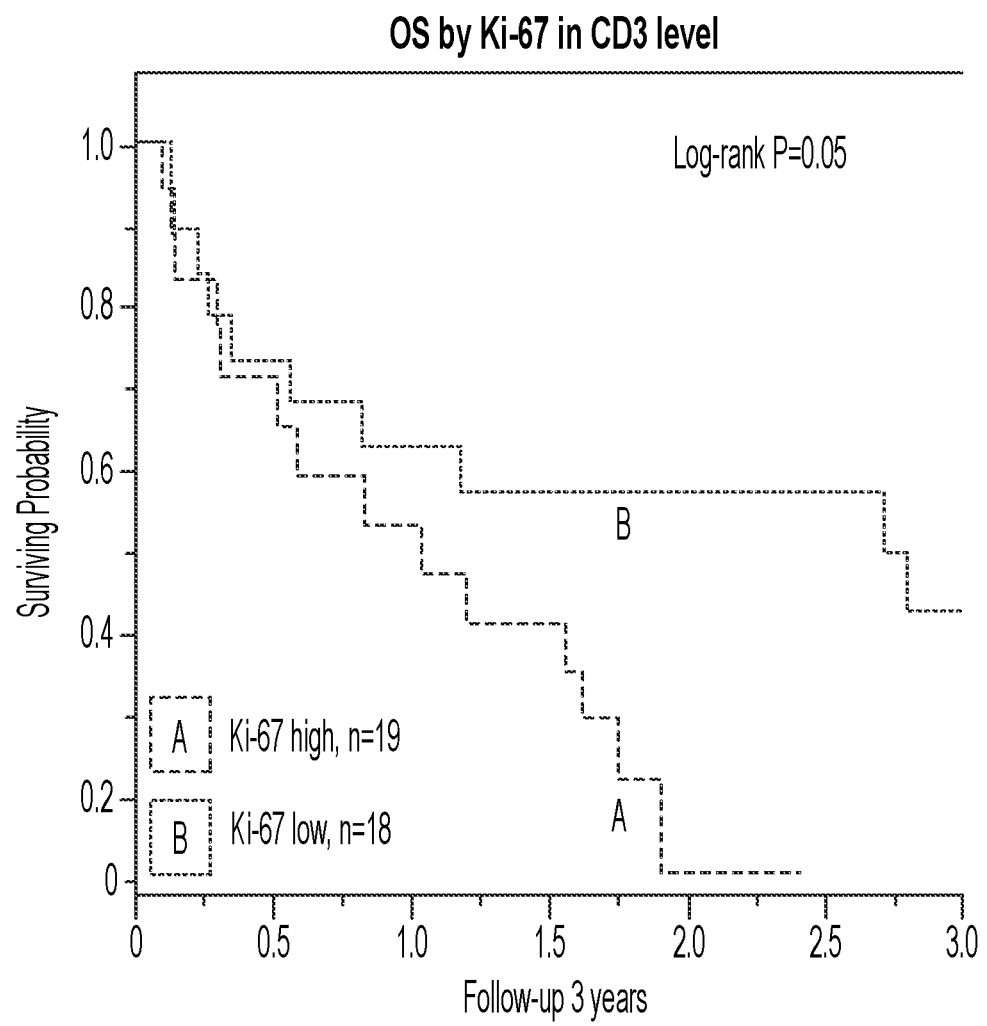
FIG. 1G shows the association between the level of T-cell Ki-67 and 3-year overall survival after treatment with immune checkpoint blockade. For each of FIGS. 1E-1G, the median score of each marker was used as stratification cut point. The log-rank P value is indicated within each chart.

It is within the level of ordinary skill in the art to determine a reference level for a biomarker within a population of patients. FIG. 1A shows the median levels of CD3, granzyme-B and ki-67, as determined by QIF score. FIGS. 1B-D correlate the short term response to immune checkpoint blockers with the level of each marker. Reference levels are defined by construction of standardized controls with mixtures of cell lines (as shown in FIGS. 1, 3 and 4). The control arrays are then used to define reproducible cutpoints.

The invention is not intended to be limited to any particular type of immune checkpoint therapy and a variety of methods known in the art may be used. Various embodiments of the invention may comprise treatment with any known form of immune checkpoint blocker or with methods not yet discovered that a person of skill in the art would recognize as immune checkpoint blockers. By way of non-limiting example, the immune checkpoint blocker may be a PD-1 inhibitor or a CTLA4 inhibitor. By way of further non-limiting example, the PD-1 inhibitor may be atezolizumab, avelumab, durvalumab, nivolumab or pembrolizumab or the CTLA4 inhibitor may be ipilimumab or tremilumimab.

Method of Selecting a Patient for Treatment with Immune Checkpoint Blockers

The invention further comprises a method for selecting a patient for treatment with immune checkpoint blockers using the above described method. In one aspect the invention comprises a method of selecting a patient for treatment with immune checkpoint blockers by measuring a level of at least one marker of T-lymphocytes in tumor tissue obtained from a patient, a level of at least one marker for proliferation and a level of at least one marker for activation in the T-lymphocytes. Then comparing the level of the marker of T-lymphocytes, the level of the marker for activation and the level of the marker for proliferation to corresponding predetermined reference levels, if the level of the marker for T-lymphocytes is above the corresponding reference level, and if the level of the markers for activation and proliferation are below the corresponding reference levels, selecting the patient for treatment with at least one immune checkpoint blocker. Selecting may comprise at least one act intended to reduce or eliminate the patient's cancer by immune checkpoint therapy or an attempt to improve the efficiency of this treatment. By way of non-limiting example, selecting may comprise advising the patient to seek immune checkpoint therapy, providing the patient with immune checkpoint blockers or referring the patient for further testing intended to confirm the patient's suitability for immune checkpoint therapy. It is specifically contemplated that the method may be applied to patients who have already been advised to pursue treatment through immune checkpoint blockers, in which case selecting may comprise continuing the course of treatment. It is also anticipated that the method may be used as a tool to select between different individual or combinations of therapies, including both combination of immune therapies and combinations of immune therapy with conventional chemotherapies and other small molecule or targeted therapies.

Kit

In certain embodiments, a kit is provided. In general, kits will comprise detection reagents that are suitable for detecting the presence of biomarkers of interest and with instructions for use in accordance with the methods of the invention. The kit may comprise antibodies or other immunohistochemical reagents capable of binding to at least one biomarker. The biomarker may, for example, be selected from the group consisting of CD3, granzyme-B or ki-67. In some embodiments, the kit is useful for detecting TILs in a tumor or for measuring levels activation/proliferation in a tumor sample from a test subject. The kit may further comprise other stains or reagents for use as controls or to enhance visualization. In certain embodiments these may comprise 4',6-Diamidino-2-Phenylindole (DAPI) for visualization of all cells or cytokeratin to detect tumor epithelial cells. In various embodiments, the kit may comprise further tools or reagents to conveniently and effectively perform the method of the invention on a tumor tissue sample from a conventional biopsy. In various embodiments, the kit may be configured for an FFPE tumor tissue sample.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the preferred embodiments of the present invention, and are not to be construed as limiting in any way the remainder of the disclosure.

The materials and methods employed in the experiments disclosed herein are now described.

Cases and Samples

Forty-five pre-treatment FFPE samples from lung cancer patients treated with immune checkpoint blockers were used in these studies. Clinico-pathological information was extracted from clinical records. Detailed description of the cohort is shown in Table 1.

TABLE 1

Characteristics of the cohort of NSCLC patients treated with immune checkpoint blockers.

| Characteristic | Number (%) |
|---|---|
| Age | |
| >70 | 7 (15.5) |
| <70 | 38 (84.5) |
| Gender | |
| Male | 33 (73.3) |
| Female | 12 (26.7) |
| Tumor histology | |
| Adencoarinoma | 31 (68.9) |
| Squamous carcinoma | 9 (20) |
| Other | 5 (11.1) |
| Tumor type | |
| Primary | 27 (60) |
| Metastatic | 18 (40) |
| Smoker | |
| Yes | 38 (84.5) |
| No | 7 (15.5) |
| Sample type | |
| Biopsy | 21 (46.7) |
| Resetion | 24 (53.3) |
| Treatment | |
| PD-1 blockade | 28 (62.2) |
| PD-L1 blockade | 12 (26.7) |
| PD-1 and CTLA-4 blockade | 5 (11.1) |

TABLE 1-continued

Characteristics of the cohort of NSCLC patients treated with immune checkpoint blockers.

| Characteristic | Number (%) |
|---|---|
| Ethnicitry | |
| Caucasian | 39 (86.7) |
| Hispanic | 5 (11.1) |
| Other | 1 (2.2) |
| Oncogenic mutation | |
| EGFR mutant | 8 (17.8) |
| KRAS mutant | 11 (24.4) |
| Other | 26 (57.8) |

All cases were diagnosed as NSCLC and treated with immune checkpoint blockers in the context of clinical trials: 28 cases PD-1 antibody monotherapy (nivolumab/pembrolizumab), 12 cases PD-L1 antibody monotherapy (atezolizumab) and 5 cases with dual PD-1/CTLA-4 blockade (nivolumab/ipilimumab). A retrospective collection containing 202 stages I-IV NSCLC not receiving immunotherapy and represented in tissue microarray format was also included. Detailed description of this cohort is provided in Table 2.

TABLE 2

Characteristics of the cohort of NSCLC patients not treated with immune checkpoint blockers.

| Characteristic | Number (%) |
|---|---|
| Age (Years) | |
| <70 | 129 (63.9%) |
| ≥70 | 73 (36.1%) |
| Gender | |
| Male | 96 (47.5%) |
| Female | 106 (52.5%) |
| Smoking Status | |
| Never | 14 (6.9%) |
| Smoker | 185 (91.6%) |
| Unknown | 3 (1.5%) |
| Histology | |
| Adenocarcinoma | 116 (57.4%) |
| Squamous | 33 (16.3%) |
| Other | 54 (26.3%) |
| Stage | |
| I-II | 126 (62.4%) |
| III-IV | 59 (29.2%) |
| Unknown | 17 (8.4%) |
| Primary Tumor Size | |
| <3 cm | 80 (39.6%) |
| ≥3 cm | 59 (29.2%) |
| Unknown | 63 (31.2%) |

Tissue Microarrays Were Prepared Using 0.6 mm Tissue Cores, Each in 2-Fold Redundancy Using Standard Procedures.

A further set of 49 pre-treatment FFPE samples from NSCLC patients who initiated immune checkpoint blockers was studied. Cases were obtained from Yale Pathology archive and clinico-pathological information was extracted from the clinical records. Detailed description of the cohort is shown in the Table 3.

TABLE 3

Clinico-pathologic characteristics of the cases in the NSCLC cohort treated with immune checkpoint blockers.

| Characteristic | Number (%) |
|---|---|
| Age | |
| >70 | 8 (16.3) |
| <70 | 41 (83.7) |
| Gender | |
| Male | 35 (71.4) |
| Female | 14 (28.6) |
| Tumor histology | |
| Non-squamous | 36 (73.5) |
| Squamous carcinoma | 11 (22.4) |
| Mixed (SCC/NSCC) | 2 (4.1) |
| Smoker | |
| Yes | 42 (85.7) |
| No | 7 (14.3) |
| Treatment | |
| PD-1 blockade | 30 (61.2) |
| PD-L1 blockade | 12 (24.5) |
| PD-1/PD-L1 and CTLA-4 | 7 (14.3) |
| Oncogenic mutation | |
| EGFR mutant | 11 (22.4) |
| KRAS mutant | 11 (22.4) |
| Other | 27 (55.2) |

Twenty-nine cases were treated with PD-1 antibody monotherapy (nivolumab/pembrolizumab), 12 cases with PD-L1 antibody (atezolizumab), 7 cases with dual PD-1/CTLA-4 blockade (nivolumab/ipilimumab or durvalumab/tremelimumab). A retrospective collection containing 110 NSCLCs not treated with immunotherapy and represented in tissue microarray (TMA) format was also included. Cases evaluated using TMAs were evaluated in 2-fold redundancy and using two independent blocks including cores from different areas of the tumor. Therefore, the results presented included integrated data from 2-4 independent tumor cores stained at least twice. Detailed description of this cohort is provided in Table 4.

TABLE 4

Clinico-pathologic characteristics of the cases in the NSCLC cohort not treated with immune checkpoint blockers.

| Characteristic | Number (%) |
|---|---|
| Age (Years) | |
| <70 | 59 (54.6%) |
| ≥70 | 49 (45.4%) |
| Gender | |
| Male | 55 (50.9%) |
| Female | 53 (49.1%) |
| Smoking Status | |
| Never | 6 (5.6%) |
| Smoker | 102 (94.4%) |
| Unknown | 0 (0.0%) |
| Histology | |
| Adenocarcinoma | 62 (57.4%) |
| Squamous | 23 (21.3%) |
| Other | 23 (21.3%) |
| Stage | |
| 0 | 8 (7.4%) |
| I-II | 71 (65.7%) |
| III-IV | 29 (26.9%) |
| Unknown | 0 (0.0%) |

TMAs were prepared using 0.6 mm cores, each in 2-fold redundancy using standard procedures.

Whole Exome Sequencing and Mutational Analysis

Genomic DNA from tumor and normal samples was captured on the Nimblegen 2.1 M human exome array and DNA libraries were sequenced on the Illumina HiSeq2500 instrument using 74-bp paired-end reads. Sequence reads were mapped to the human b37 reference genome using the Burrow-Wheeler Aligner-MEM (BWA-MEM) program and mutation calling was performed with GATK following the Best Practices guidelines. For matched tumor-normal pairs, somatic point mutations and indels were called by MuTect2 using Bayesian classifiers. For unmatched tumor samples, MuTect2 compared the tumor to the reference panel of normal samples of the same ethnicity. For all somatic mutations called, the mutations that were supported by at least two alternative non-reference alleles present in more than 5% of all sequencing reads or a total of eight independent reads were considered. Identified variants were further filtered based on their presence in repositories of common variations (1,000 Genomes, NHLBI exome variant server and 2,577 non-cancer exomes) and annotated using ANNOVAR. For all matched samples, somatic CNVs were analyzed using EXCAVATOR that normalizes the non-uniform whole-exome sequencing read depths taking GC-content, mappability, and exon-size into account and calculates the ratio of normalized read depth between tumor and normal for the exome capture intervals. LOH calling and purity estimation were performed as previously described.

HLA Typing and Class-I/II Neoantigen Prediction

The 4-digit patient-specific HLA class I type was determined by ATHLATES in silico. All nonsynonymous somatic mutations identified from the whole exome sequencing analysis were translated into 17-mer polypeptides flanking the mutant amino acid. The binding affinity of mutant nonamers to the patient-specific HLA class I type was predicted using NetMHCcons algorithms. Nonamers with IC50 below or equal to 500 nM were further tested for the recognition by the T-cell receptor using Class I immunogenicity resulting in putative neoantigens. HLA class II type for each patient was estimated using the PHLAT algorithm. 53-mer polypeptides were identified by the in-house script with the nonsynonymous somatic mutation in the middle at position 27. The binding affinity of 53-mer polypeptides to the patient-specific HLA class II type was calculated by NetMHCIIpan-3.0.

In Vitro HLA-A2 Stabilization Assay

Experimental validation of the HLA binding capacity of in silico predicted class-I mutant neoantigenic peptides identified in NSCLC was performed by measuring the stabilization of HLA-A2 protein after incubation of B-lymphoblastoid LCL-174 cells with recombinant mutant 9-mer peptides. LCL-174 cells are irradiated and immuno-selected human cells having specific deletions and lacking MHC-II genes and TAP proteins; and expressing only HLA-A2, -C1 and -B5 protein. Cells were incubated overnight with 50 μM recombinant 9-mer mutant peptides found in NSCLC and stained for HLA-A2 protein using a fluorescently labeled primary antibody by flow cytometry. Peptides inducing surface HLA-A2 signal above the negative control sample were considered as positive binders.

DNA and RNA Sequencing Analysis from TCGA Dataset

Gene expression and somatic mutation was analyzed for 514 lung adenocarcinomas and 504 lung squamous cell carcinomas from The Cancer Genome Atlas database (TCGA). Somatic mutational load was calculated as total number of mutations identified in each tumor sample. Normalized gene expression of tumor was downloaded from TCGA data portal and further analyzed to correct for batch effects using the MD Anderson GDAC's MBatch website (http://bioinformatics.mdanderson.org/tcgabatcheffects). Spearman's rank correlations were then calculated between the somatic mutational load and normalized expression levels of 9 immune-related genes using 464 LUAD and 178 LUSC samples that have both somatic mutation and gene expression data.

Immunohistochemistry

PD-L1 immunohistochemistry (IHC) was stained using the FDA-approved PD-L1 IHC 22C3 pharmDx kit on the Dako Link 48 platform according to manufacturer recommendations using 4 µm-thick whole tissue histology tumor preparations. The 22C3 antibody in this kit is provided already diluted at an unspecified ratio, was stained and scored by a trained pathologist using bright field microscopy and a semi-quantitative score. Values were expressed as percentage of tumor cells displaying predominant membrane signal.

Multiplexed Quantitative Immunofluorescence

The multiplexed TIL staining protocol was performed using 5-color multiplex fluorescence with simultaneous detection of 5 markers labeled using isotype specific antibodies. Fresh histology sections from the cases were deparaffinized and subjected to antigen retrieval using EDTA buffer (Sigma-Aldrich™, St Louis, Mo.) pH=8.0 and boiled for 20 min at 97° C. in a pressure-boiling container (PT module, Lab Vision™). Slides were then incubated with dual endogenous peroxidase block (DAKO™ #S2003, Carpinteria, Calif.) for 10 min at room temperature and subsequently with a blocking solution containing 0.3% bovine serum albumin in 0.05% Tween solution for 30 minutes. Slides were stained with 4',6-Diamidino-2-Phenylindole (DAPI) for visualization of all cells, cytokeratin to detect tumor epithelial cells, CD3 for T-lymphocytes, granzyme-B for T-cell activation and ki-67 as cell proliferation marker. Primary antibodies included cytokeratin clone M3515 from DAKO, CD3 clone E272 from Novus Biologicals™, Granzyme-B clone 4E6 from Abcam and ki-67 clone MIB1 from DAKO. Secondary antibodies and fluorescent reagents used were goat anti-rabbit Alexa546 (Invitrogen™), anti-rabbit Envision (K4009, DAKO™) with biotynilated tyramide/Streptavidine-Alexa750 conjugate (Perkin-Elmer™); anti-mouse IgG1 antibody (eBioscience™, CA) with fluorescein-tyramide (Perkin-Elmer™), anti-mouse IgG2a antibody (Abcam™, MA) with Cy5-tyramide (Perkin-Elmer™). Residual horseradish peroxidase activity between incubations with secondary antibodies was eliminated by exposing the slides twice for 7 min to a solution containing benzoic hydrazide (0.136 mg) and hydrogen peroxide (50 µl).

Tissue Fluorescence Measurement and Scoring

Quantitative measurement of the fluorescent signal was performed using the AQUA® method that enables objective and sensitive measurement of targets within user-defined tissue compartments. Briefly, the QIF score of each target in CD3+T-cell compartment was calculated by dividing the target pixel intensities by the area of CD3 positivity in the sample. Scores were normalized to the exposure time and bit depth at which the images were captured, allowing scores collected at different exposure times to be comparable. Stained slides were visually examined by a pathologist and defective samples or areas with staining artifacts were re-analyzed or excluded.

Patient-Derived Xenograft Model

Briefly, surgical specimens (10 mm$^2$) from primary lung carcinomas was divided in 2 halves. A portion of each half was used for morphology studies and most of the tissue was implanted subcutaneously into the flank of NOD-scid IL2rgc−/− mice. Four independent animals were engrafted and treated intraperitoneally with anti-hPD-1 mAbs (clone M3) or PBS at days 5 and 10. At day 12 mice were sacrificed and tumors were collected for analysis.

Cell Preparation and Mass Cytometry (CyTOF) Analysis

Tumors were minced and mechanically dissociated with the GentleMACS Dissociator (Miltenyi Biotec) in the presence of RPMI1640 with 0.5% BSA and 5 mM EDTA. The resulting cell suspension was filtered using a 70-µm cell strainer (BD Falcon). Cells were centrifuged at 600 g for 7 min at 4° C. and re-suspended in PBS with 0.5% BSA and 0.02% NaN3. $2 \times 10^6$ cells from each tumor were incubated with antibodies against CD16/32 at 50 ug/ml in a total volume of 50 µl for 10 min at RT to block Fc receptors. Surface marker antibodies were then added, yielding 100 µL final reaction volume and stained for 30 min at 4 C. Following staining, cells were washed twice with PBS containing 0.5% BSA and 0.02% NaN3. Then, cells were re-suspended with RPMI1640 and 10 µM Cisplatin (Fluidigm Corp) in a total volume of 400 ul for 1 min before quenching 1:1 with pure FBS to determine viability. Cells were centrifuged at 600 g for 7 min at 4 C and washed once with PBS with 0.5% BSA and 0.02% NaN3. Cells were then fixed using Fixation/Permeabilization Buffer (ebioscience) for 30 min at 4 C. After two washes with Perm buffer (ebioscience) cells were incubated with intracellular antibodies cocktail in 100 µl for 30 min at 4 C. Cells were washed twice in PBS with 0.5% BSA and 0.02% NaN$_3$ and then stained with 1 mL of 1:4000 191/193Ir DNA intercalator (Fluidigm) diluted in PBS with 1.6% PFA overnight. Cells were then washed once with PBS with 0.5% BSA and 0.02% NaN3 and then two times with double-deionized (dd)H20. Mass cytometry samples were diluted in ddH2O containing bead standards to approximately $10^6$ cells per mL and then analyzed on a CyTOF 2 mass cytometer (Fluidigm). All files were normalized together using the mass-cytometry data normalization algorithm and analyzed using viSNE.

Statistical Analyses

Mutational data and QIF signals were analyzed using Spearman's Rho rank regression functions. Cases data and characteristics were compared using non-parametric t-test for continuous variables and chi-square test for categorical variables. Overall survival functions were compared using Kaplan-Meier estimates and statistical significance was determined using the log-rank test. The mutational load, candidate class-I neoantigen content and TIL markers were stratified using the median score. Statistical analyses were performed using JMP® Pro software (version 9.0.0, 2010, SAS Institute Inc.™) and GraphPad Prism v6.0 for Windows™ (GraphPad Software, Inc™).

Figure 3C:
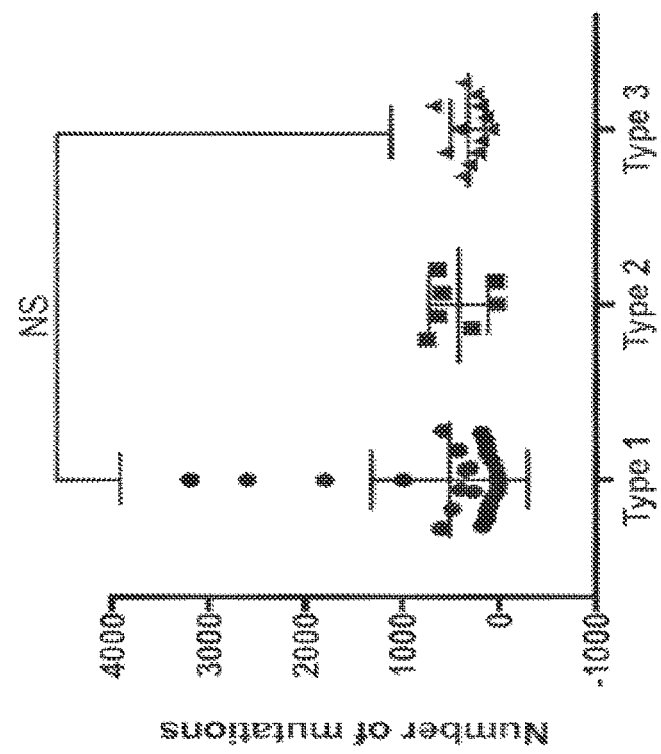
FIG. 3C depicts the association between the mutational load and specific TIL patterns found in lung tumors from patients treated with immune checkpoint blockers.

Example 1: Tumor Lymphocyte Infiltration, In Situ TIL Activation/Proliferation and Benefit from Immune Checkpoint Blockade in NSCLC In 37 cases from the cohort with available tumor tissue, levels of T-cells and in situ T-cell activation/proliferation was measured using multiplex quantitative immunofluorescence (QIF). Our QIF panel included the markers DAPI to highlight all cells/nuclei in the sample, cytokeratin to stain tumor lung epithelial cells, CD3 for T-lymphocytes, granzyme-B for T-cell activation and Ki-67 for cell proliferation. The level of CD3 was measured as a metric of T-cell infiltration and the amount of granzyme-B and ki-67 in CD3-positive cells as indicators for T-cell activation and proliferation, respectively. The design and performance of this panel was validated using control FFPE preparations of human tonsil, lymph node and unstimulated (control) human PBMCs or PBMCs stimulated with CD3/CD28 antibodies (FIG. 2). The level of CD3 signal showed a continuous distribution and a wide range going from virtually no TILs to prominent T-lymphocyte infiltration (FIG. 1A). The level of CD3 was not correlated with the level of T-cell cytolytic activity (R=0.16, P=0.33) and only moderately correlated with T-cell proliferation (R=0.39, P=0.01). As depicted in FIG. 1B, the level of T-cell infiltration was 2.3-fold higher in short-term responders than in non-responders, but this difference did not reach statistical significance. The level of TIL activation and proliferation was not associated with the presence or absence of response to therapy (FIGS. 1C-D). However, elevated levels of CD3 (FIG. 1E) and low levels of T-cell activation/proliferation (FIGS. 1F-G) were associated with longer 3-year overall survival, indicating that the highest clinical benefit to immune checkpoint blockade occurs in cases with abundant tumor T-cell infiltration but limited activation (e.g. "dormant TILs"). In support of this notion, stratification of the cases into 3 groups based on their CD3, T-cell granzyme-B and Ki-67 levels (FIGS. 3A-B) identified tumors with a dormant TIL phenotype as the one with the longest survival ("Type 2", log rank P<0.006, FIGS. 3A-B). Representative multicolor fluorescence pictures of the tumors showing distinct QIF-based TIL patterns are shown in FIG. 3A. A restricted survival benefit was seen in tumors with low T-cell infiltration ("Type 1") and those with elevated T-lymphocytes and marked in situ activation/proliferation (e.g. "Type 3"). Notably, the level of somatic mutations and predicted class-I neoantigens were not significantly different across the TIL NSCLC subtypes and the majority of cases with very high mutational load or candidate neoantigens displayed a type 1 TIL pattern (FIGS. 3C-D).

Figure 4A:
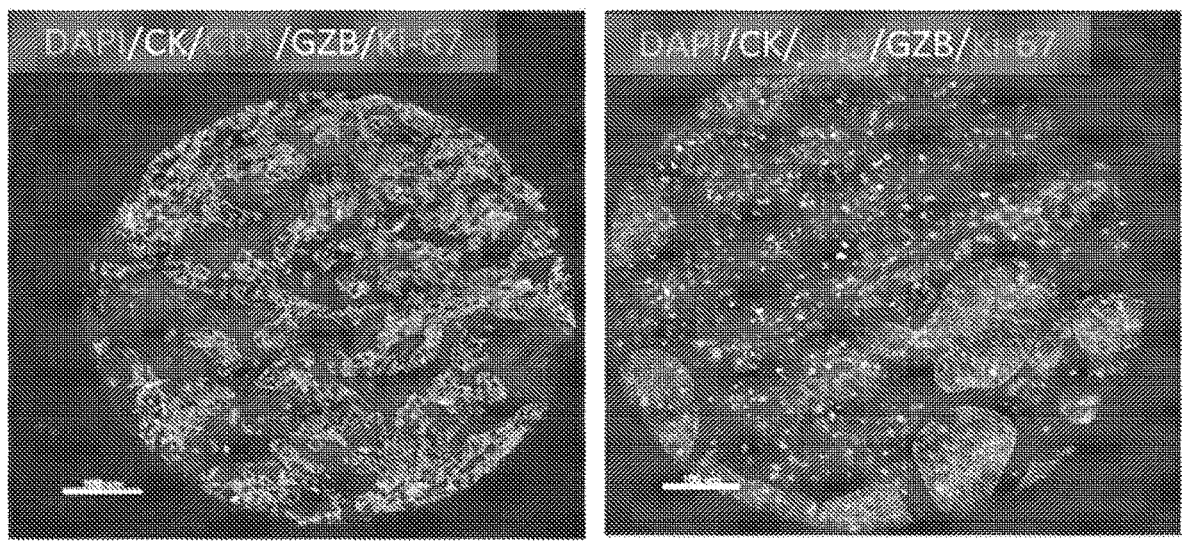
FIG. 4A depicts immunofluorescent staining of a lung tumor with low (left) and high (right) T-cell activation/proliferation. Slides were simultaneously stained with a multiplex QIF panel containing CD3, ki-67, granzyme-B, DAPI, and cytokeratin. Bar=100 μm.
Figure 4B:
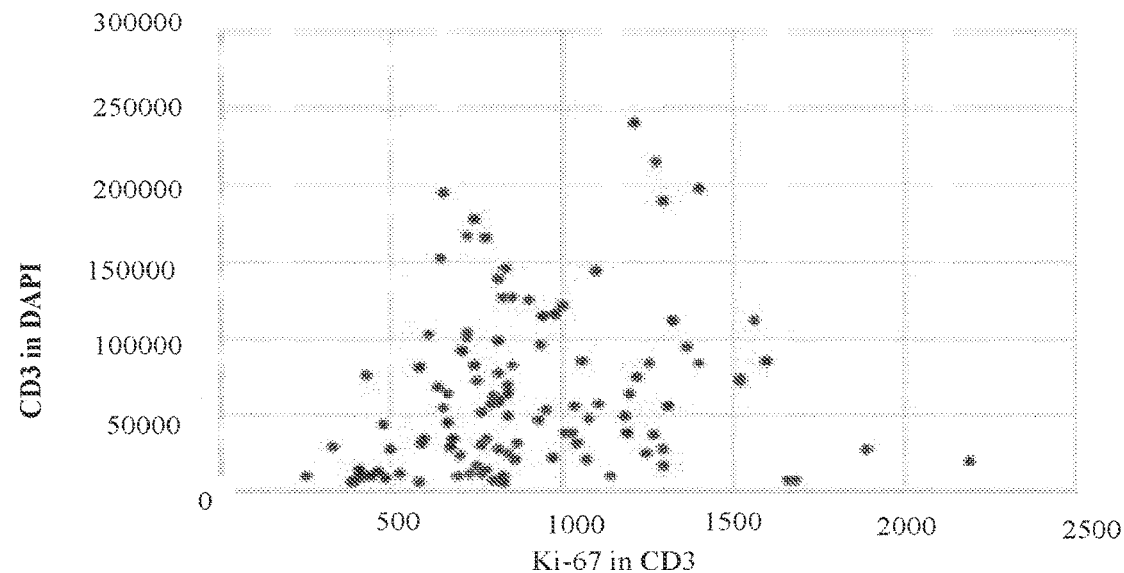
FIG. 4B depicts the association between the level of CD3 and T-cell ki-67 in 202 NSCLCs from a retrospective collection of samples from patients not treated with immune checkpoint blockers.
Figure 4C:
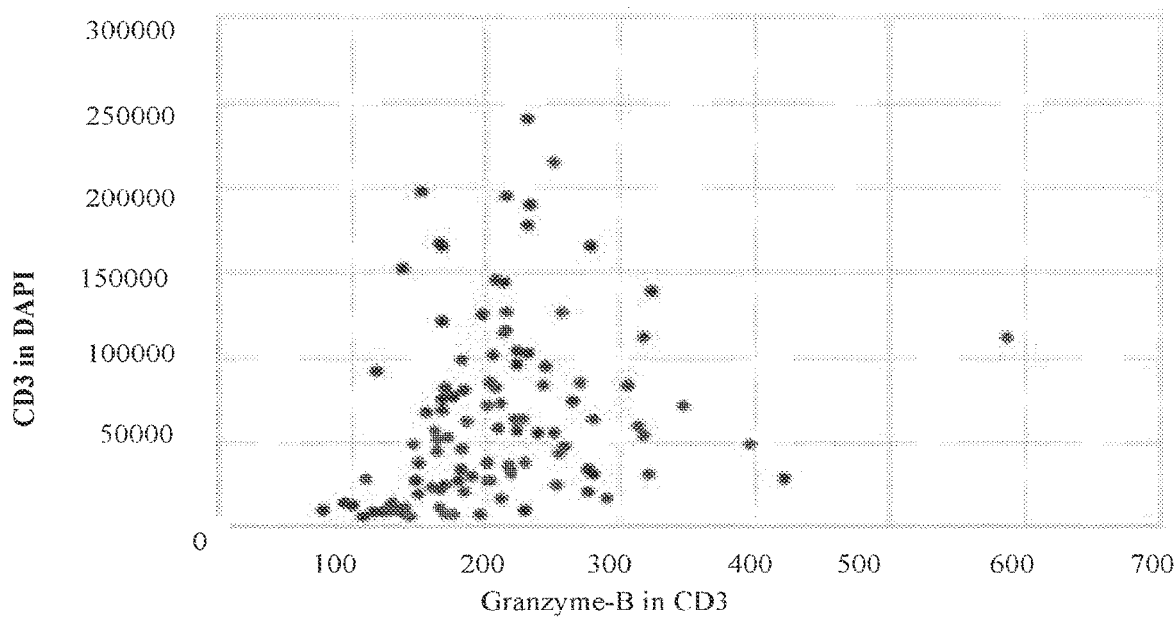
FIG. 4C depicts the association between the level of CD3 and T-cell granzyme-B in 202 NSCLCs from a retrospective collection of samples from patients not treated with immune checkpoint blockers.
Figure 4D:
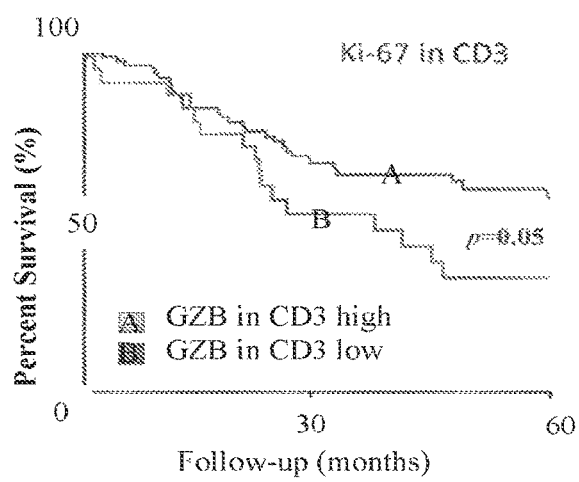
FIG. 4D depicts Kaplan-Meier graphical analysis of 5-year overall survival of lung cancer cases from a retrospective collection of samples from patients not treated with immune checkpoint blockers according to the levels of T-cell ki-67.
Figure 4E:
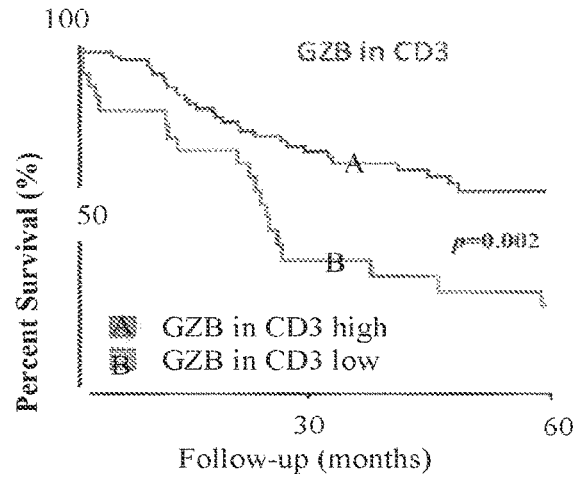
FIG. 4E depicts Kaplan-Meier graphical analysis of 5-year overall survival of lung cancer cases from a retrospective collection not treated with immune checkpoint blockers according to the levels of T-cell granzyme-B. In both FIG. 4D and FIG. 4E, the log-rank P value is indicated in the chart. Together.

To assess the specificity of the association between the QIF-based TIL signature and treatment with immune checkpoint blockers, levels of T-cell infiltration, activation and proliferation were measured in a retrospective collection of 202 stages I-IV NSCLCs not treated with immunotherapy and represented in tissue microarray format (FIG. 4A). Similar to the treated cases, the level of CD3 in lung tumors was variable and not directly associated with the T-cell activity/proliferation (FIGS. 4B-C). However, in this population a low cytolytic activity and proliferation of T-lymphocytes in the tumor microenvironment was associated with shorter overall survival (FIGS. 4D-E), supporting that the presence of a dormant TIL signature is associated with better outcome only after treatment with immune checkpoint blockers.

Figure 5A:
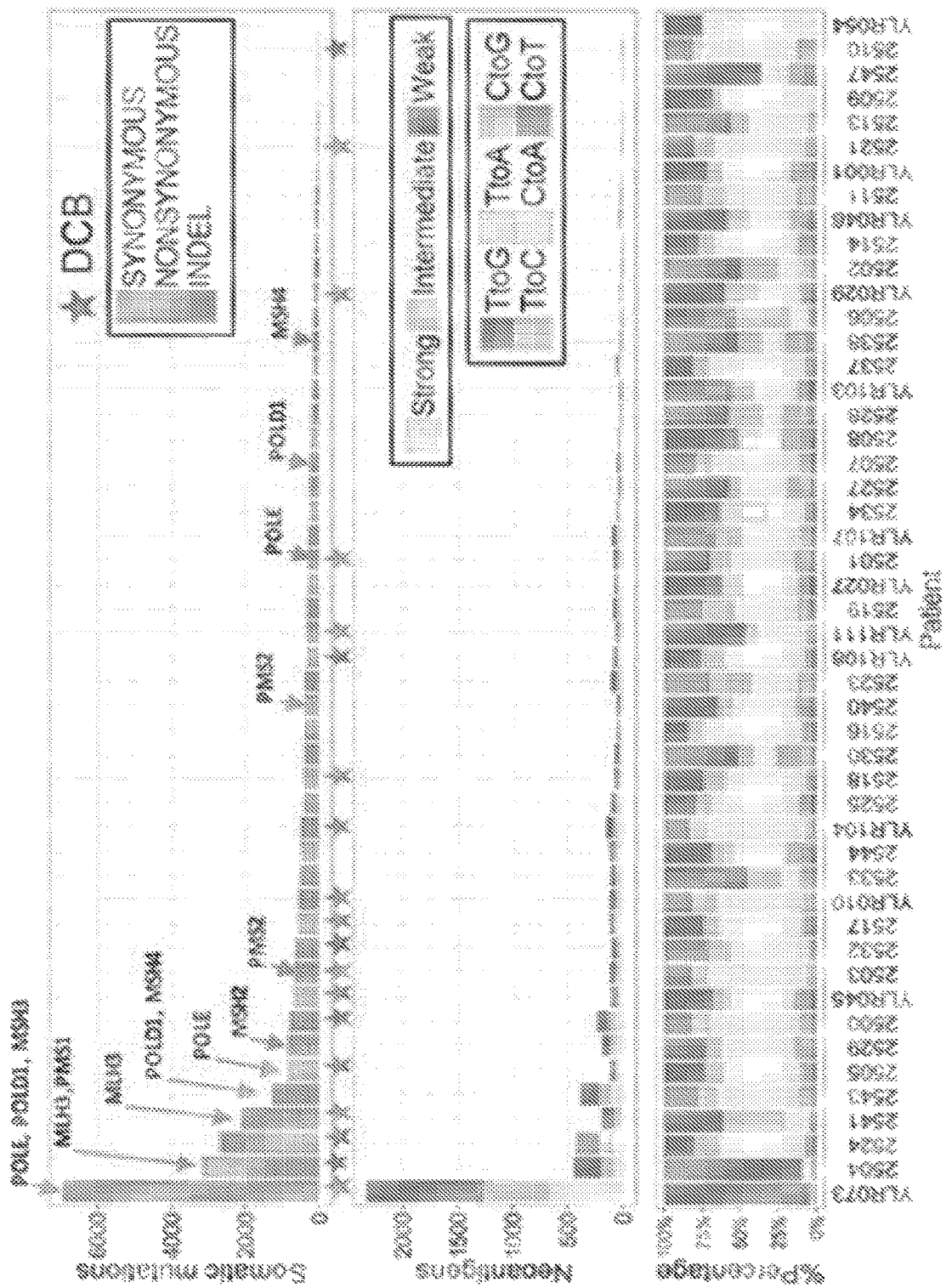
FIGS. 5A-5E depict the association between mutations, candidate class-I neoantigens and benefit from immune checkpoint blockers in NSCLC.

Example 2: Mutational Load, Predicted Class-I Neoantigens and Benefit from Immune Checkpoint Blockade in NSCLC To characterize the mutational landscape of our cohort and its association with clinical response, whole exome DNA sequencing analysis of pre-treatment formalin-fixed paraffin-embedded (FFPE) NSCLC samples from 49 patients treated with immune checkpoint blockers was performed. The mean target coverage was 206.3× and 97.08% of nucleotides read at least 20×. The average somatic mutation load was 633.27 (range 10-6926) with a median of 346. The average nonsynonymous mutational load was 444.7 (range 5-4577) with a median of 252 and the mean ratio of nonsynonymous to synonymous variants was 3.11. The association between the total mutational load and the number of nonsynonymous variants was high (Spearman's correlation coefficient [R]=0.99, P<0.0001). As shown in FIG. 1A, cases with a mutational burden above the median of the cohort showed a 3.6-fold higher frequency of durable clinical benefit (DCB [partial or complete response, or stable disease, by RECIST v1.1 lasting≥24 weeks]) than cases with lower mutational content (60 [15 of 25] vs 16.7% [4 of 24] with DCB, respectively, P=0.05). In addition, highly mutated tumors had 2.6-fold higher frequency of variants in genes associated with DNA repair (e.g. MLH3, MSH6, POLD1, POLE, etc) than cases with low mutations, but this difference did not reach statistical significance (32% [8 of 25] vs 12.5% [3 of 24], P=0.31). As expected for a NSCLC population, the majority of cases displayed a mutational signature with predominance of C>A transversions, previously reported to be associated with tobacco exposure (FIG. 5A).

Figure 5B:
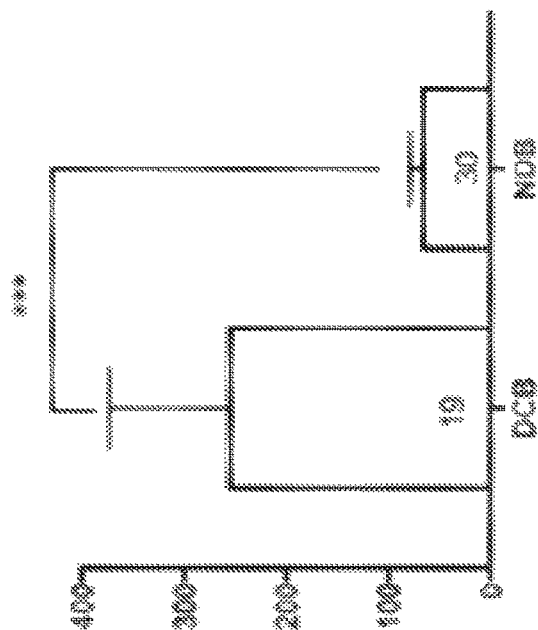

Candidate class-I neoantigens were identified through a bioinformatic pipeline including: i) In silico translation of the nonsynonymous mutant sequences into 17-mer polypeptides flanking the mutant amino acid; ii) calculation of mutant nonamers with $IC_{50}$ below or equal to 500 nM to bind patient-specific class-I HLA alleles; and iii) determination of the predicted recognition of mutant sequences by T-cells[13,23,25]. As shown in FIG. 5B and Table 5, a mean of 138.8 candidate MHC class-I neoantigens per case (range 2-2331) was identified, 25.9% of which were predicted to be high affinity binders (calculated $IC_{50}$≤50 nM), 26.8% intermediate binders (calculated $IC_{50}$ 50≤150 nM) and 47.3% weak binders (calculated $IC_{50}$≤500 nM). There was a high correlation between the mutational load and predicted class-I neoantigen content (Spearman's R=0.95, P<0.0001), as reported.

TABLE 5

| | Neoantigen (n = 49) | | | |
|---|---|---|---|---|
| | Total | Strong (≤50 nM) | Intermediate (>50 & ≤150 nM) | Weak (>150 & ≤500 nM) |
| Median | 72 | 16 | 20 | 34 |
| Mean | 138.78 | 35.94 | 37.14 | 65.69 |

Figure 5C:
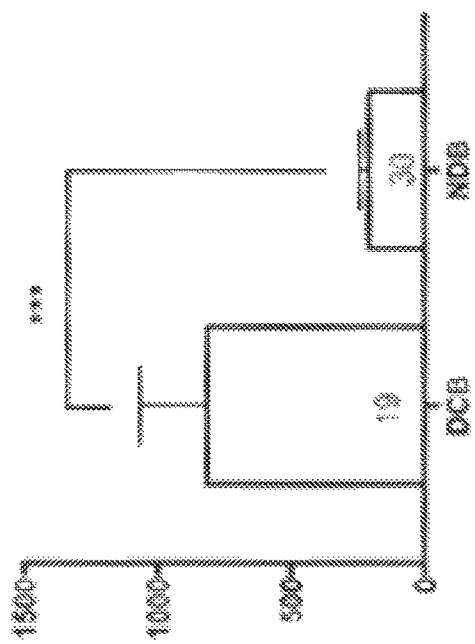
Figure 5D:
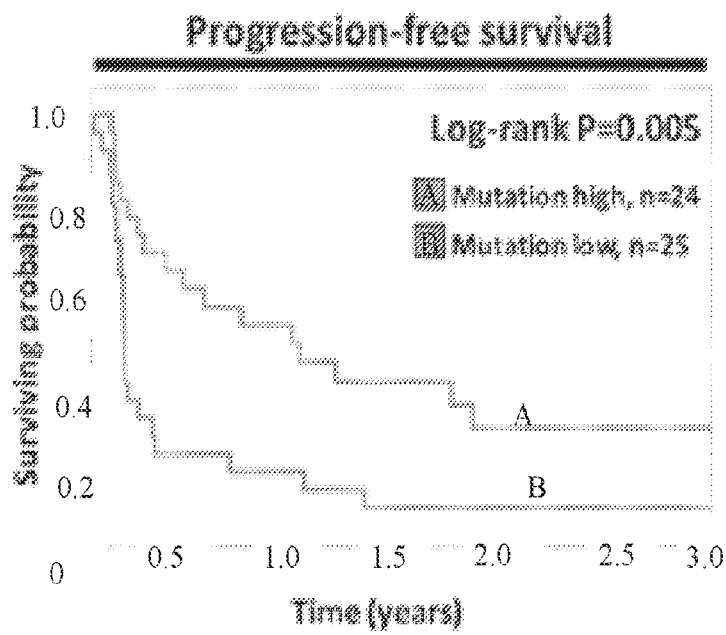
Figure 5E:
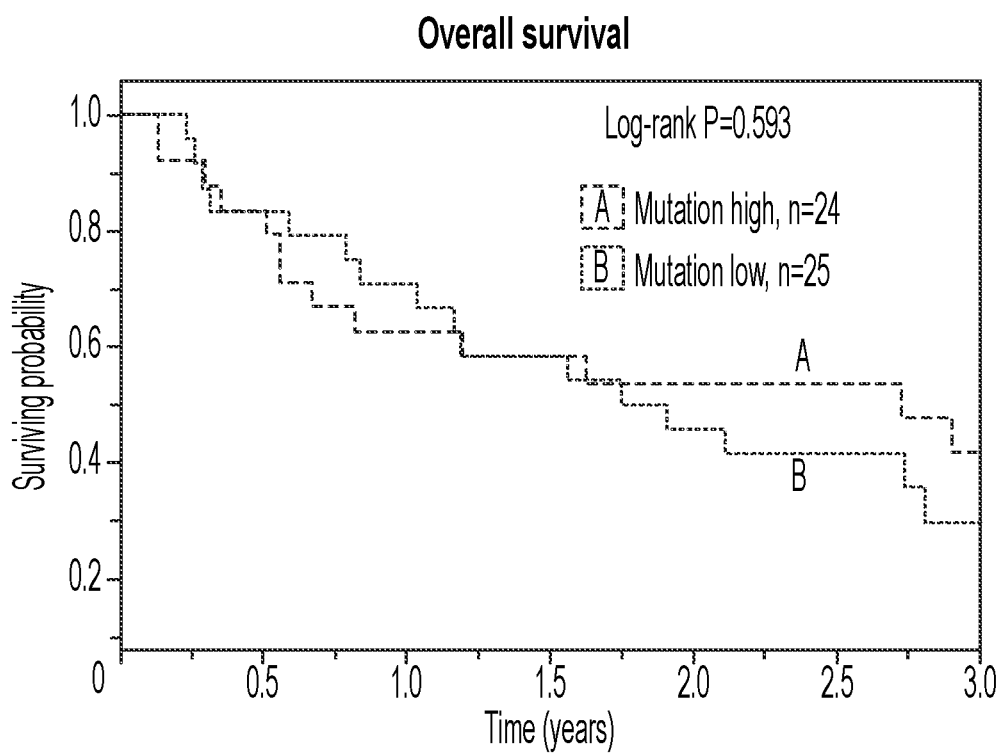
Figure 12:
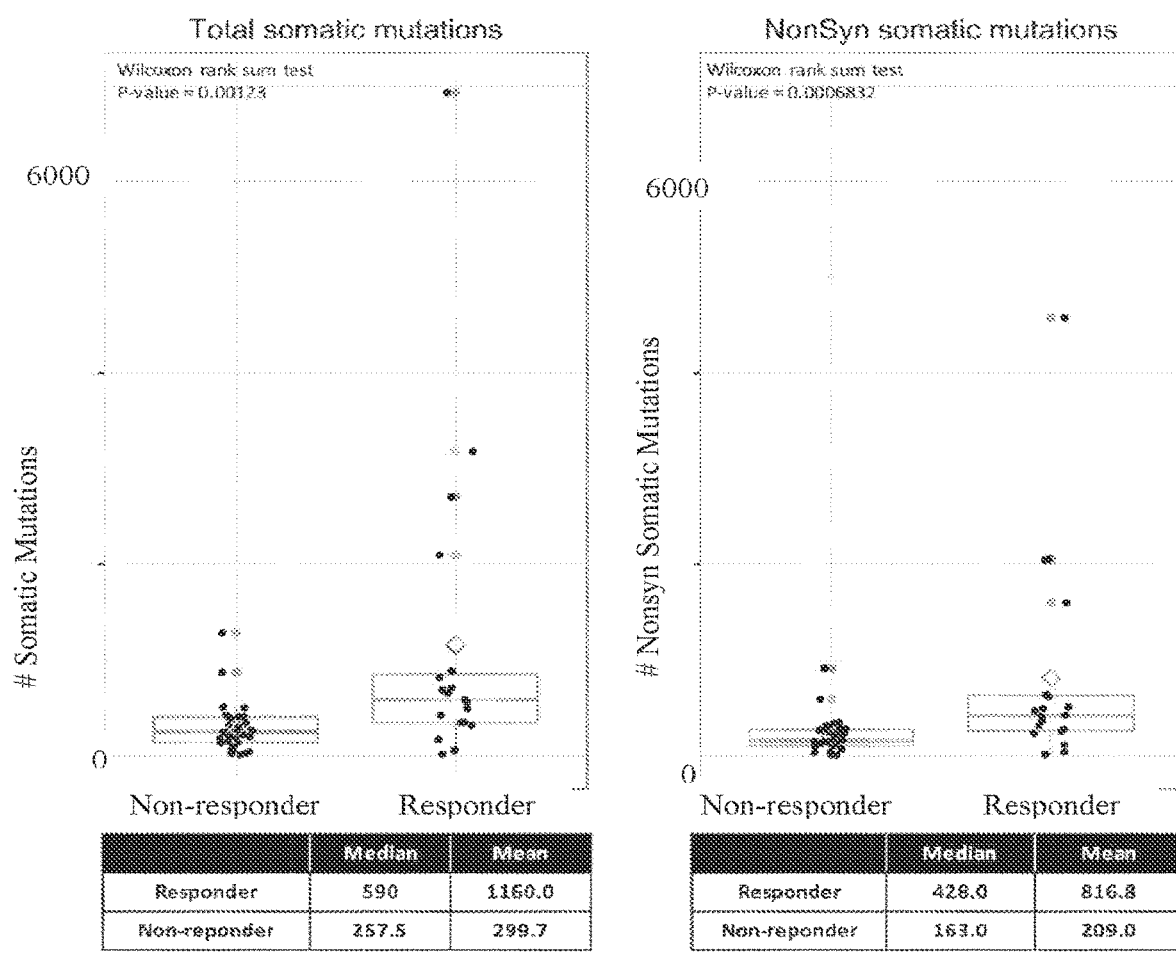
FIG. 12 depicts the association between total somatic mutations, nonsynonymous somatic mutations and response to immune checkpoint blockers in NSCLC.
Figure 13A:
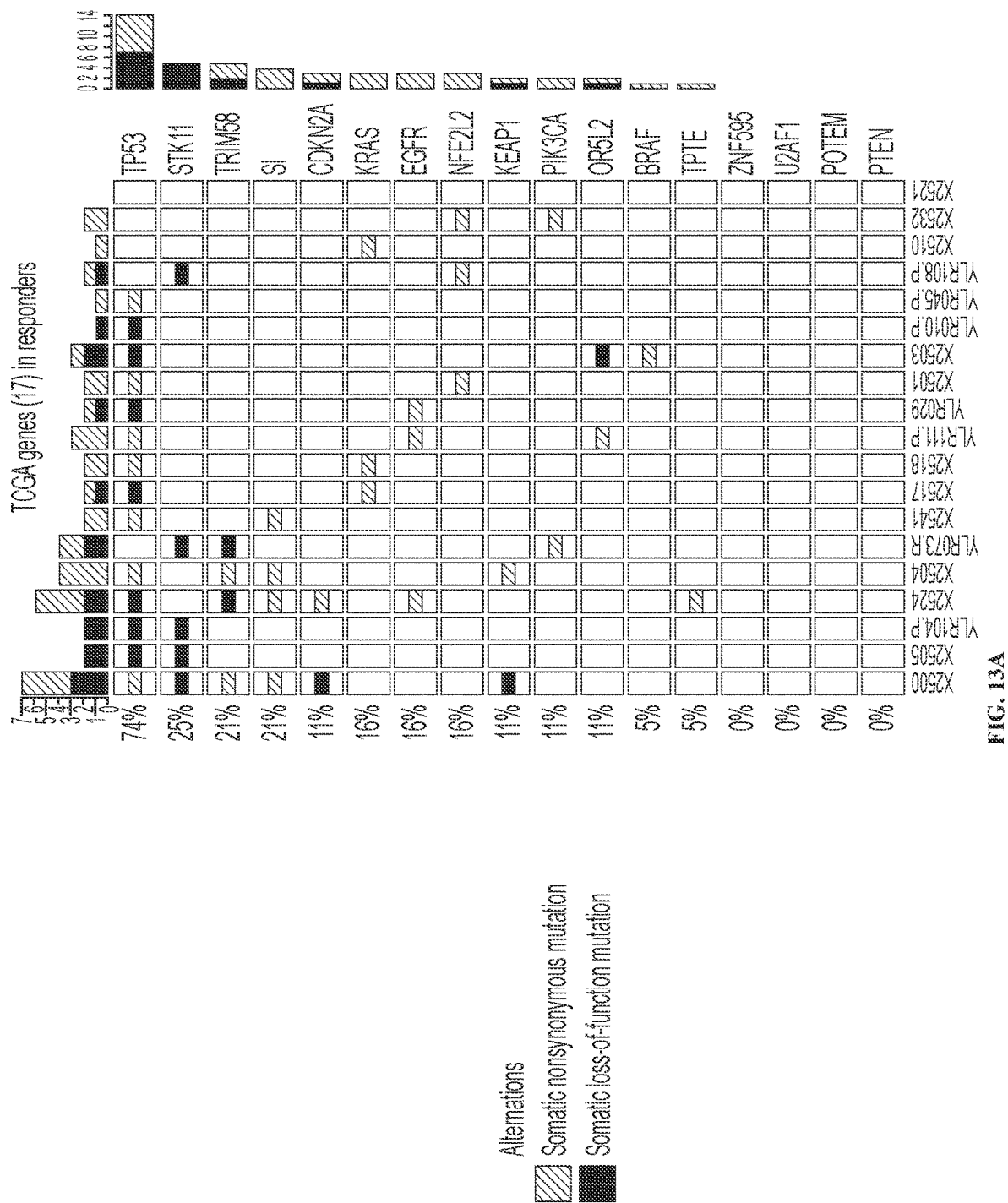
FIG. 13 depicts the association between mutations in cancer-related genes from TCGA and response to immune checkpoint blockers in NSCLC.
Figure 13B:
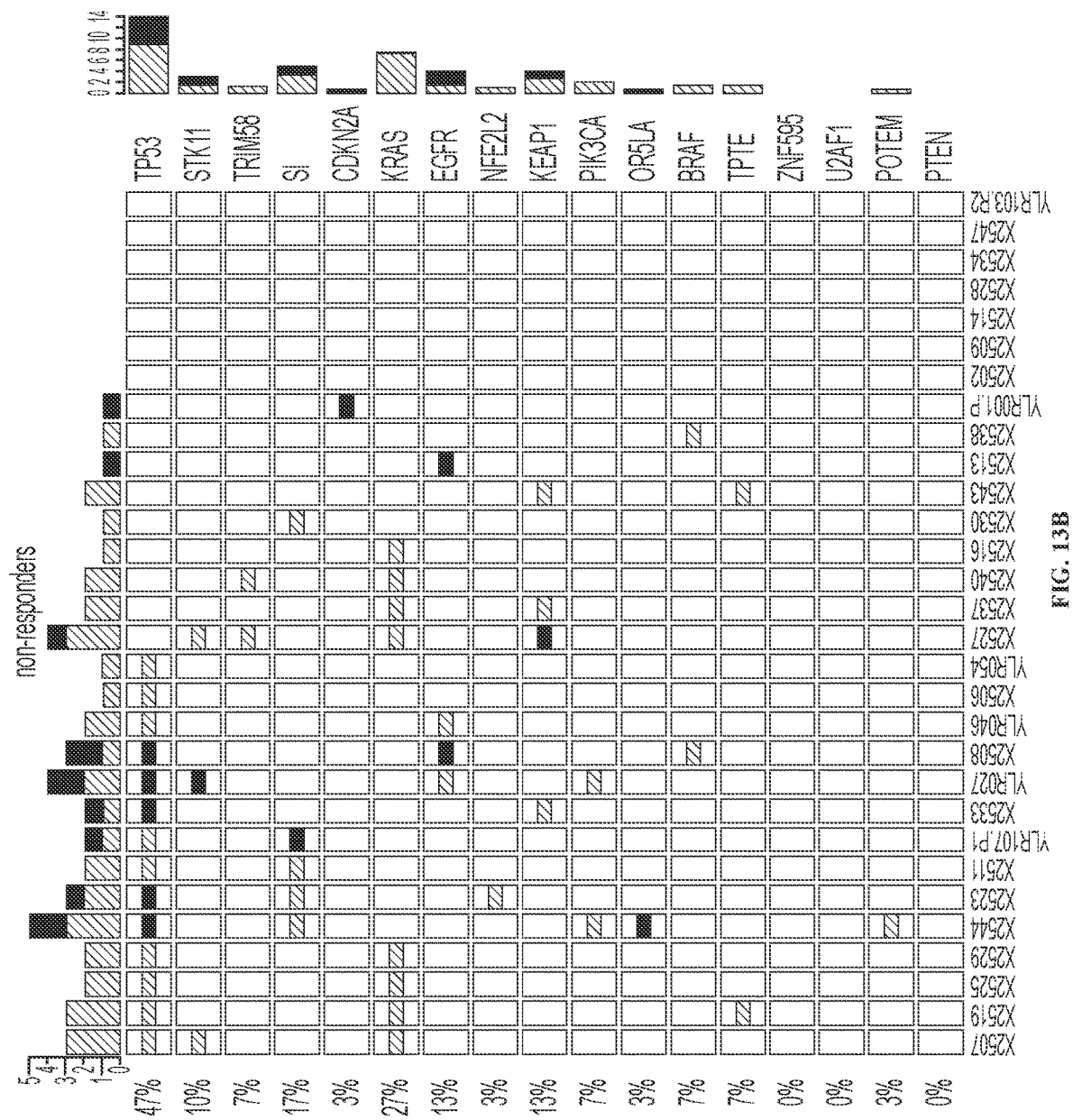
Figure 14A:
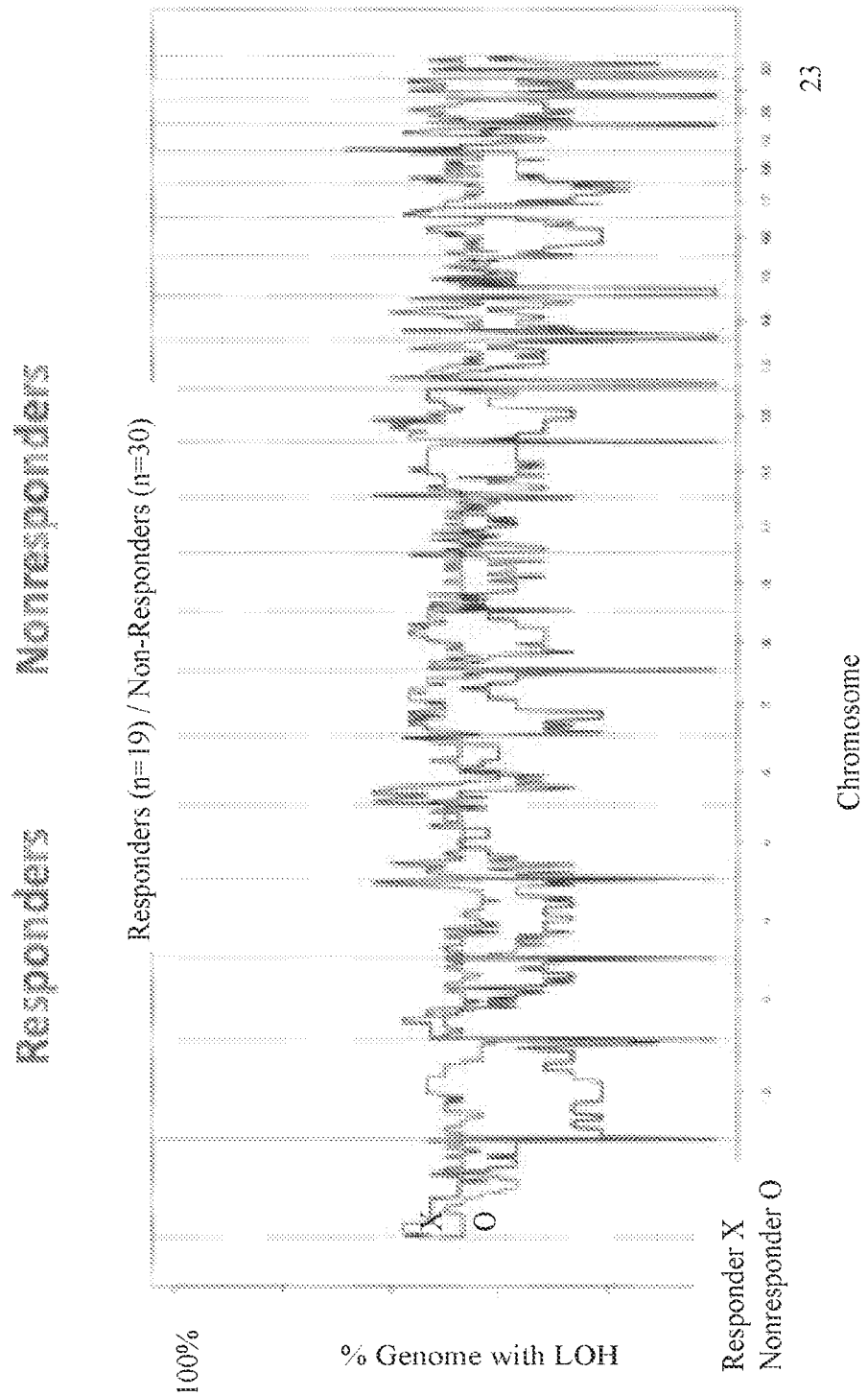
FIGS. 14A and 14B depict the association between response to immune checkpoint blockers (FIG. 14A) and loss of heterozygosity (LOH) (FIG. 14B) in NSCLC.
Figure 14B:
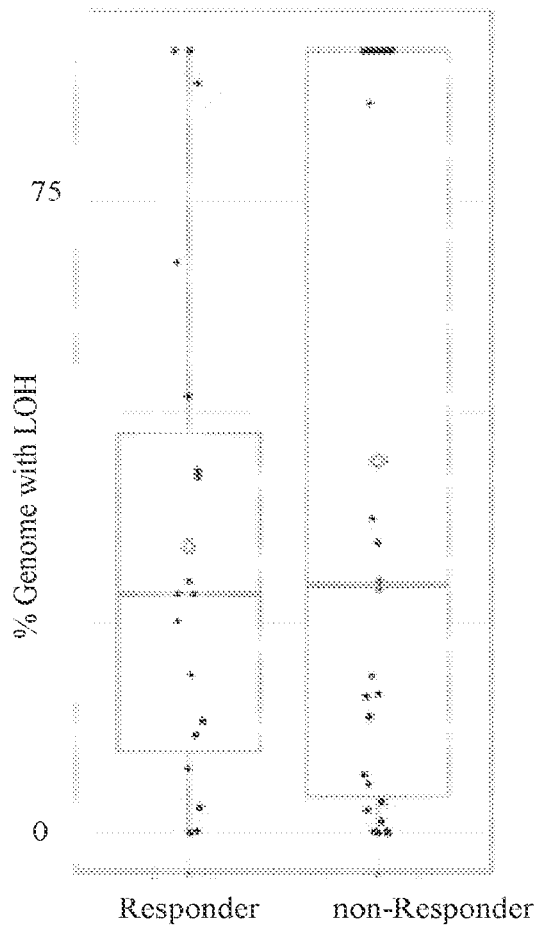

Both the nonsynonymous mutational load and the number of in silico predicted MHC class-I neoantigens were significantly higher in cases with durable clinical benefit than in patients rapidly progressing after immune checkpoint blockade (P=0.0004 and P=0.0009, respectively [FIGS. 5B-C]). However, some patients with low mutations/neoantigens achieved response or prolonged stable disease. A comparable result was obtained using the total mutational burden (FIG. 12). Using the median as a cut-point, the sensitivity of the nonsynonymous mutational load to predict durable clinical benefit was 78.9% and the specificity was 66.6%. The most frequently mutated cancer-related gene in the cohort was TP53 (57.1%). No significant difference in the relative frequency of specific oncogenic mutations was found (FIG. 13), global loss of heterozygosity (LOH) (FIG. 14) or in the amount of copy number gains and losses (CNVs, FIG. 15) between durable responders and patients lacking benefit from immune checkpoint blockers. Increased nonsynonymous mutational load was significantly associated with longer progression free survival (FIG. 5D, P=0.005). However, no significant association between the level of mutations and overall survival at 3-years using the same stratification cut-point (FIG. 5E, log-rank P=0.59) was found. An equivalent association with survival was seen using the number of candidate class-I neoantigens (FIG. 16).

Example 3: In Vitro HLA Binding of Mutant Neoantigenic Peptides Found in NSCLC

Figure 6B:
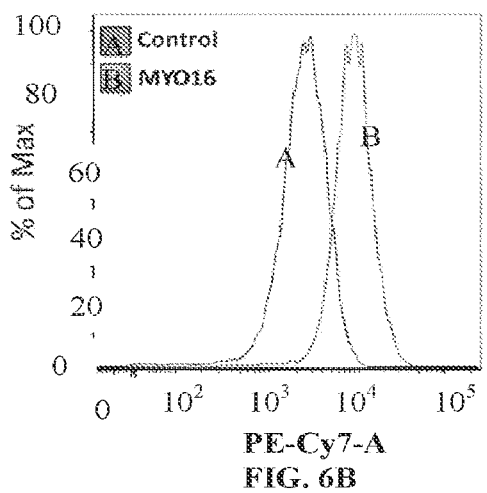
Figure 6C:
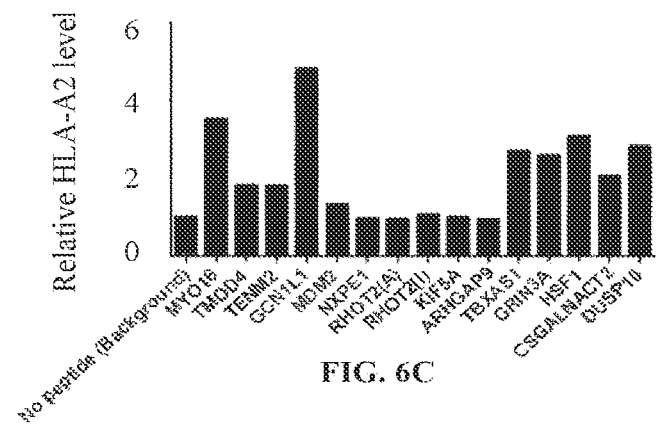
Figure 6D:
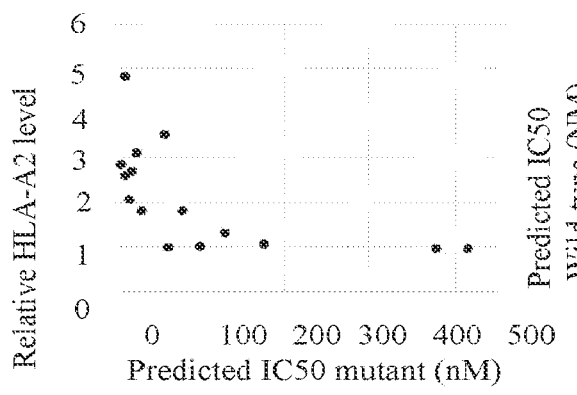
Figure 6E:
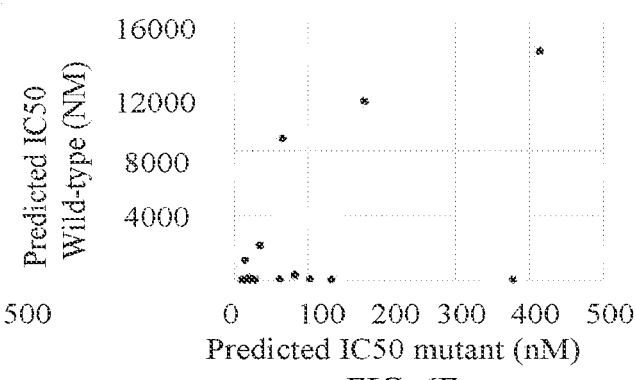

Experimental validation of the HLA binding capacity of in silico predicted class-I mutant neoantigenic peptides found in NSCLC was performed by measuring the stabilization of HLA-A2 protein after incubation of B lymphoblastoid LCL-174 cells lacking MHC-II genes and TAP proteins, with recombinant mutant 9-mer peptides. As shown in FIGS. 6A-C, 9 out of 13 (67.9%) predicted mutant neopeptides found in tumor samples obtained over the course of treatment in a patient with HLA-A*0201 HLA type showed positive surface fluorescence signal, indicating effective peptide-class-I MHC binding. The predicted affinity of the mutant peptide-HLA-A2 interaction was correlated with the in vitro stabilization scores, showing the highest HLA-A2 signal in those cases with the lowest predicted $IC_{50}$ (FIG. 6D). Notably, 4 out of 5 mutant peptides with predicted $IC_{50}$>100 nM failed to show detectable HLA stabilization, indicating limited actual binding. In addition, the predicted binding affinity of the mutant relative to the non-mutated (e.g. wild-type) peptides was prominently higher (mean $IC_{50}$ 103.6±33.2 for the mutant peptides vs 2541±1218 for the wild type sequences) and showed limited correlation (FIG. 6E).

Figure 7B:
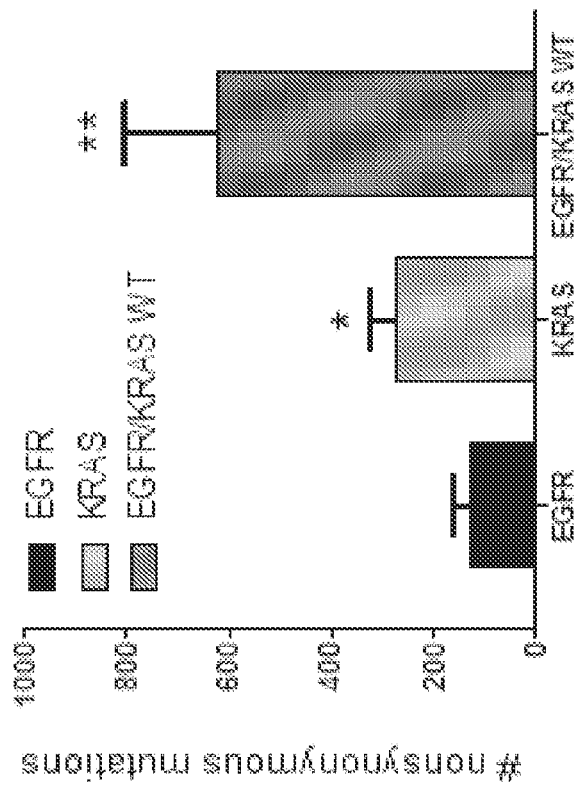
FIGS. 7A-7D depict the association between the mutations, predicted MHC class-I neoantigens, major oncogenic drivers and tobacco consumption.
Figure 7A:
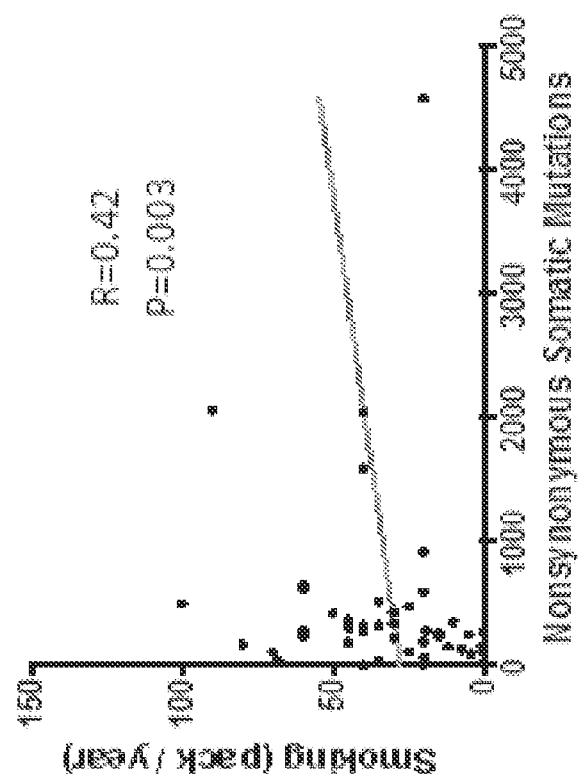
Figure 7C:
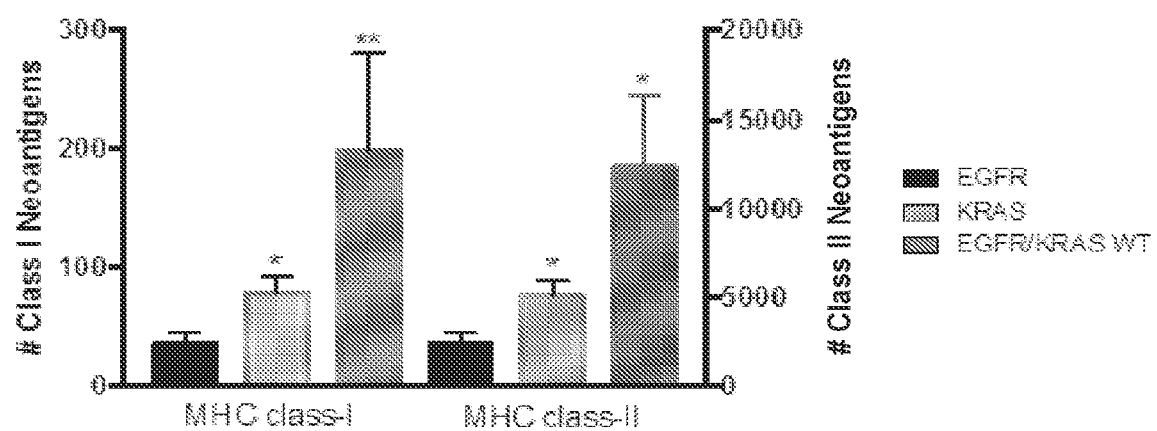
Figure 7D:
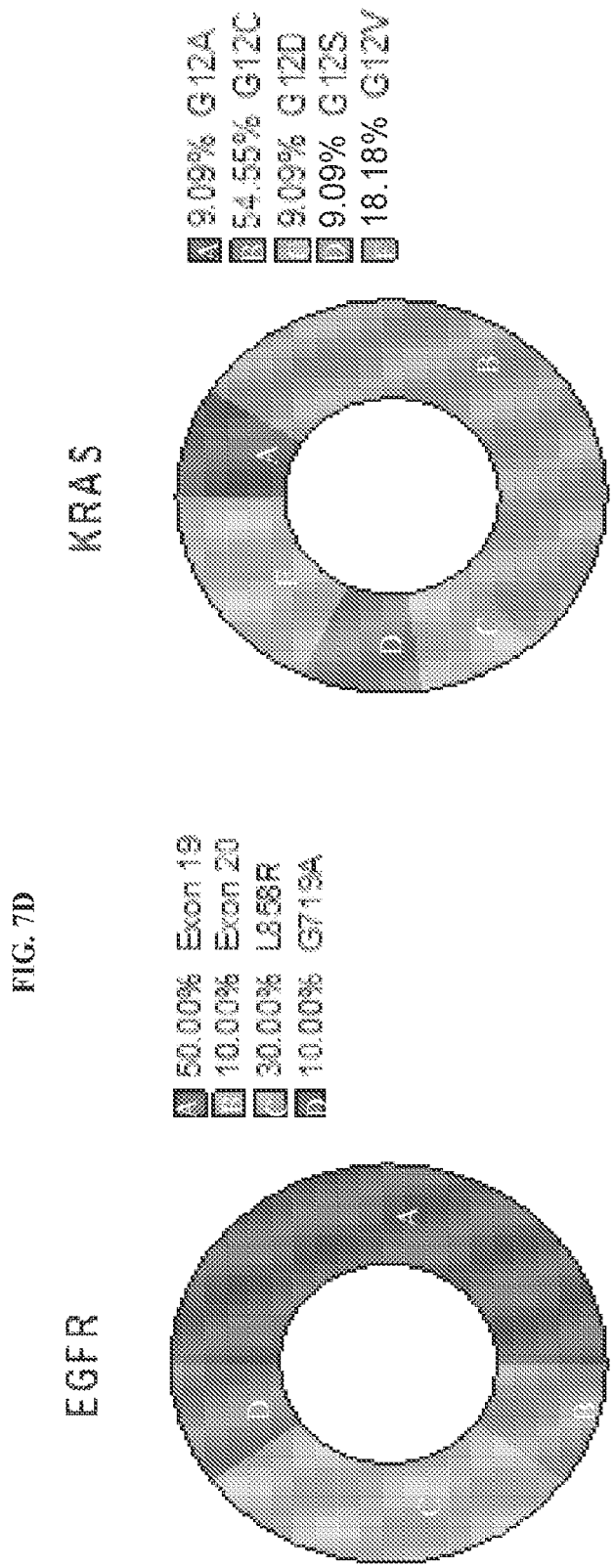

Example 4: Association of Mutations and Candidate Neoantigens with Major Oncogenic Drivers and Tobacco Consumption As expected, the mutational load was positively correlated with the amount of cigarette smoking (Spearman's R=0.42, P=0.01, FIG. 7A). Tumors harboring activating mutations in EGFR had significantly lower somatic mutations and predicted MHC class-I and class-II neoantigens than KRAS-mutant and EGFR/KRAS wild type tumors (P<0.01, FIGS. 7B-C). Although the tumors lacking mutations in EGFR and KRAS showed a higher mutational/candidate class-I/II neoantigen level than KRAS-mutant carcinomas, this difference was not statistically significant. As expected, the majority of EGFR mutations corresponded to Exon 19 deletions (50% of EGFR mutant cases) and all KRAS variants were located in codon 12 with G12C being the most frequently detected (54% of KRAS mutant tumors) (FIGS. 7D-E).

Figure 8A:
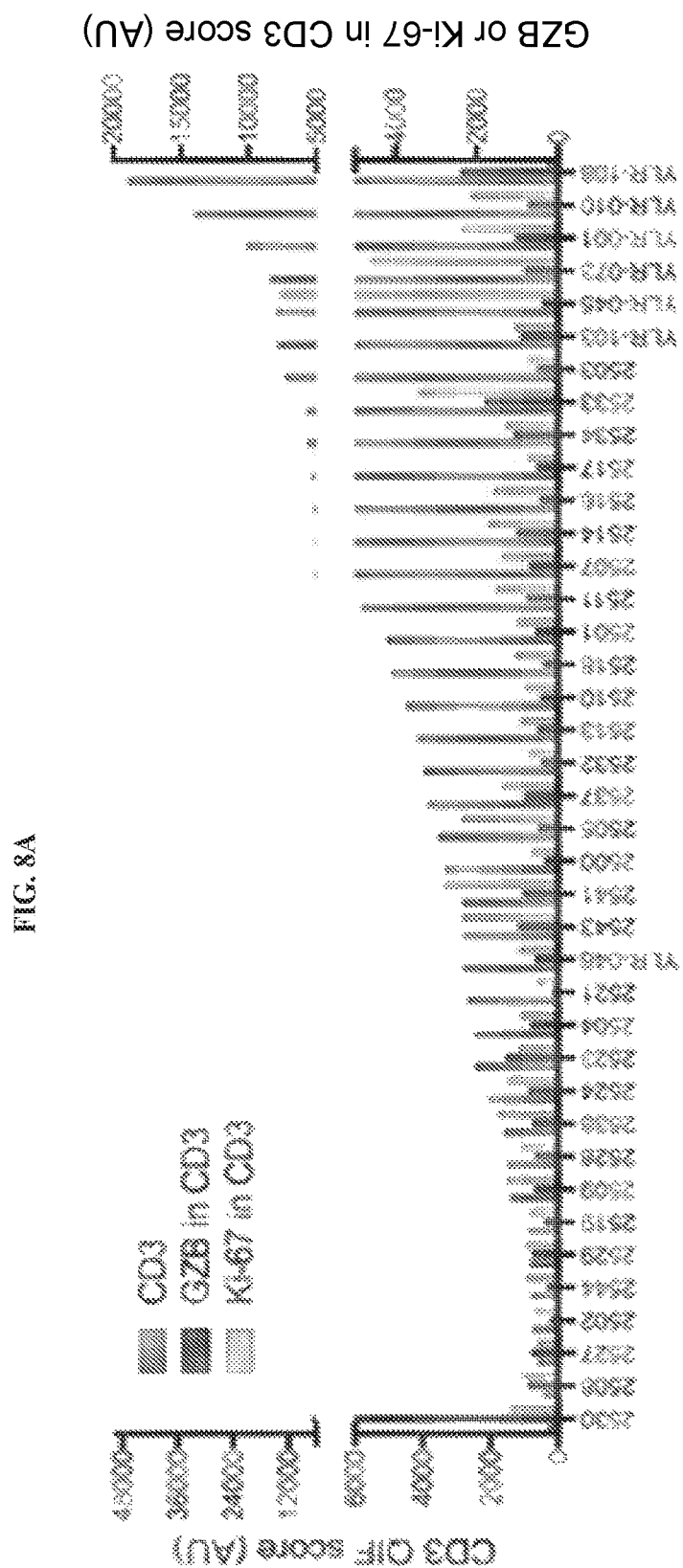
FIGS. 8A-8G depict the association between local T-cell infiltration, activation/proliferation and benefit from immune checkpoint blockers in NSCLC.
Figure 8B:
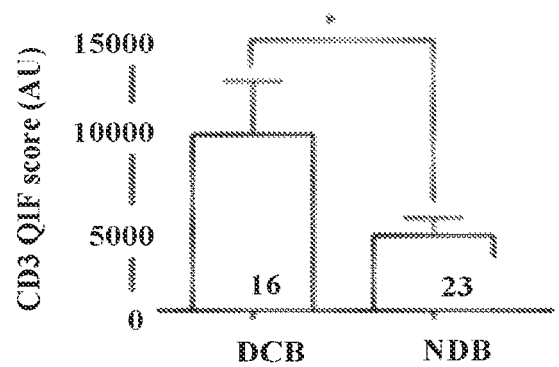
Figure 8C:
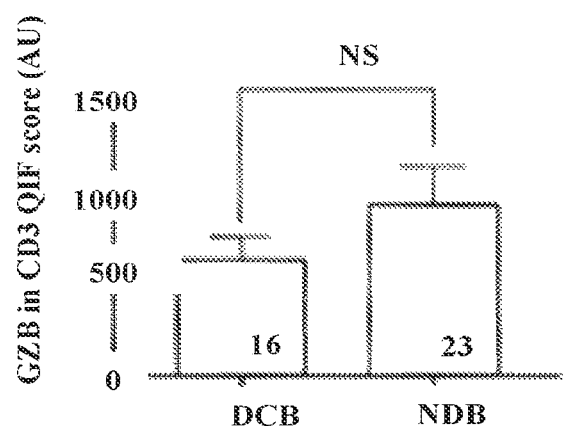
Figure 8D:
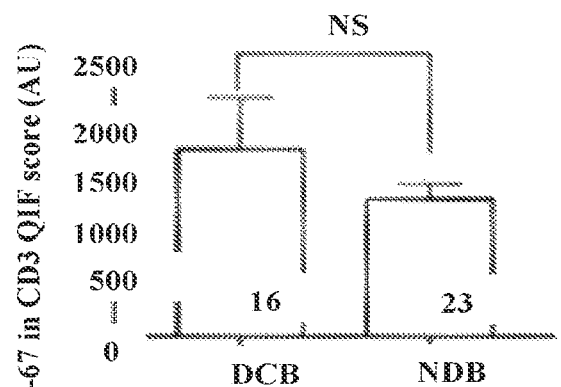
Figure 17A:
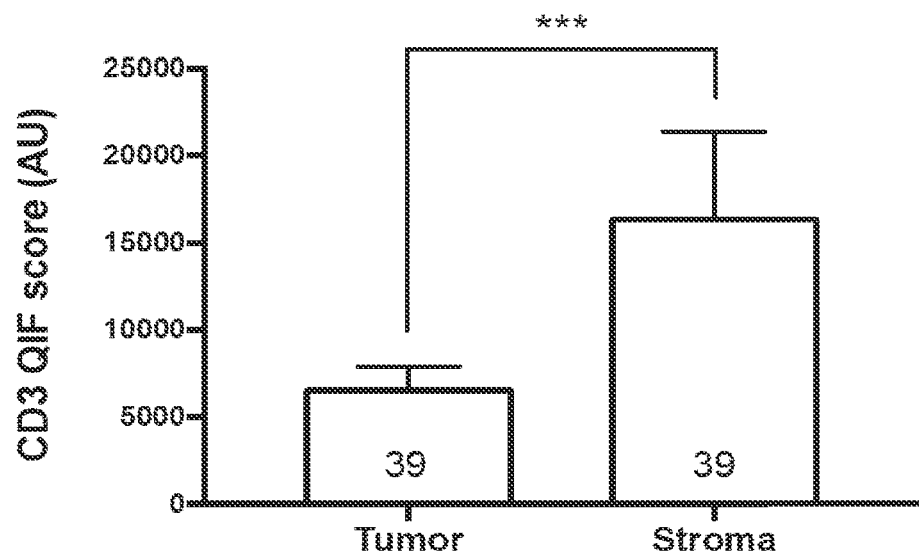
FIG. 17A depicts the association between the level of CD3+ in the tumor and stroma of NSCLC samples.
Figure 17B:
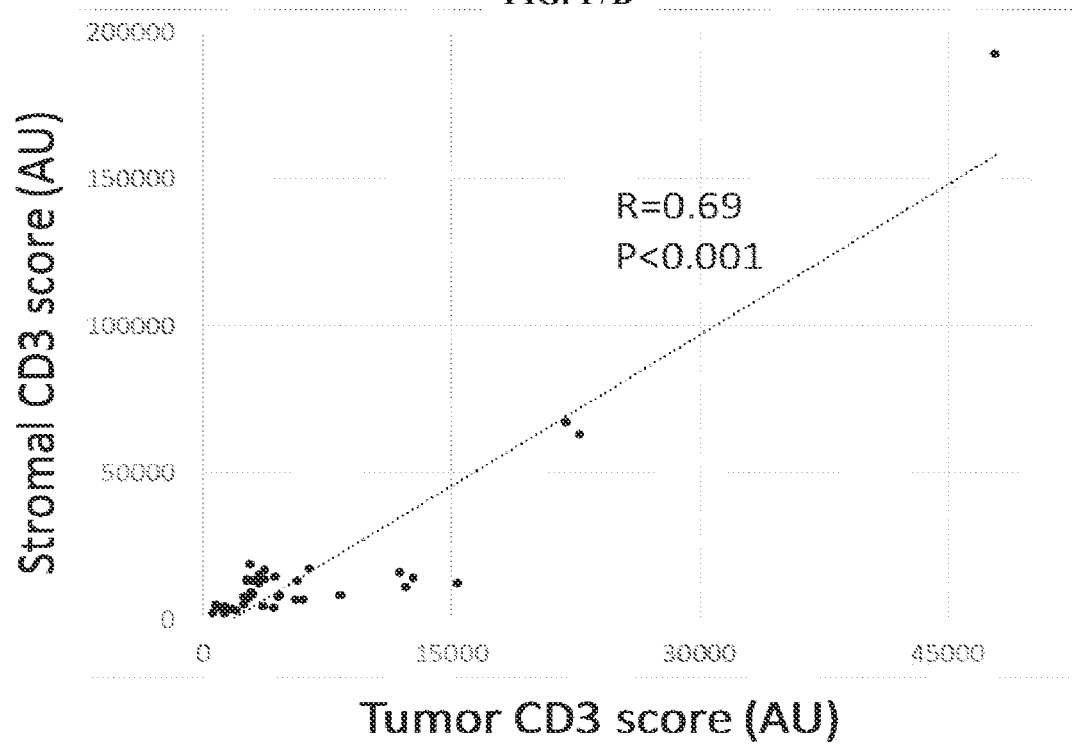
FIG. 17B is a graph depicting that association between stromal and tumor CD3 scores.

Example 5: Tumor Lymphocyte Infiltration, In Situ TIL Activation/Proliferation and Benefit from Immune Checkpoint Blockade in NSCLC The levels of T-cells and in situ T-cell activation/proliferation was measured using multiplex quantitative immunofluorescence (QIF) in 39 cases from the cohort with available tumor tissue. Our QIF panel included DAPI to highlight all cells/nuclei in the sample, cytokeratin to stain tumor epithelial cells, CD3 for T-lymphocytes, granzyme-B (GZB) for T-cell activation and Ki-67 for cell proliferation. The level of CD3 as a metric of T-cell infiltration and the amount of GZB and Ki-67 in CD3-positive cells were measured as indicators for T-cell activation and proliferation, respectively. The design and performance of this panel was validated using control FFPE preparations of human tonsil, lymph node and unstimulated (control) human PBMCs or PBMCs stimulated for 72 h with anti-human CD3 monoclonal antibodies (clone OKT-3) (FIG. 2). The level of CD3 signal showed a continuous distribution and a wide range going from virtually no TILs to prominent T-lymphocyte infiltration (FIG. 8A). As shown in FIG. 17, the stromal CD3 signal (CD3 in CK-negative areas) was 2.5 fold higher (P<0.001) than in the tumor (CD3 in CK-positive areas), indicating that the majority of the T-cells were located in the stromal compartment. However, the stromal and tumor CD3 levels were positively correlated in the cohort. The level of CD3 signal was not correlated with the level of T-cell GZB (Spearman's R=0.23, P=0.14) and only modestly correlated with T-cell proliferation (Spearman's R=0.41, P=0.01). The level of T-cell infiltration was significantly associated with sustained response to immune checkpoint blockers and the scores were 2.4-fold higher in cases with DCB (FIG. 8B, P=0.02). The level of TIL activation and proliferation was not associated with the presence or absence of response to therapy or prolonged stable disease (FIGS. 8C-D).

Figure 8E:
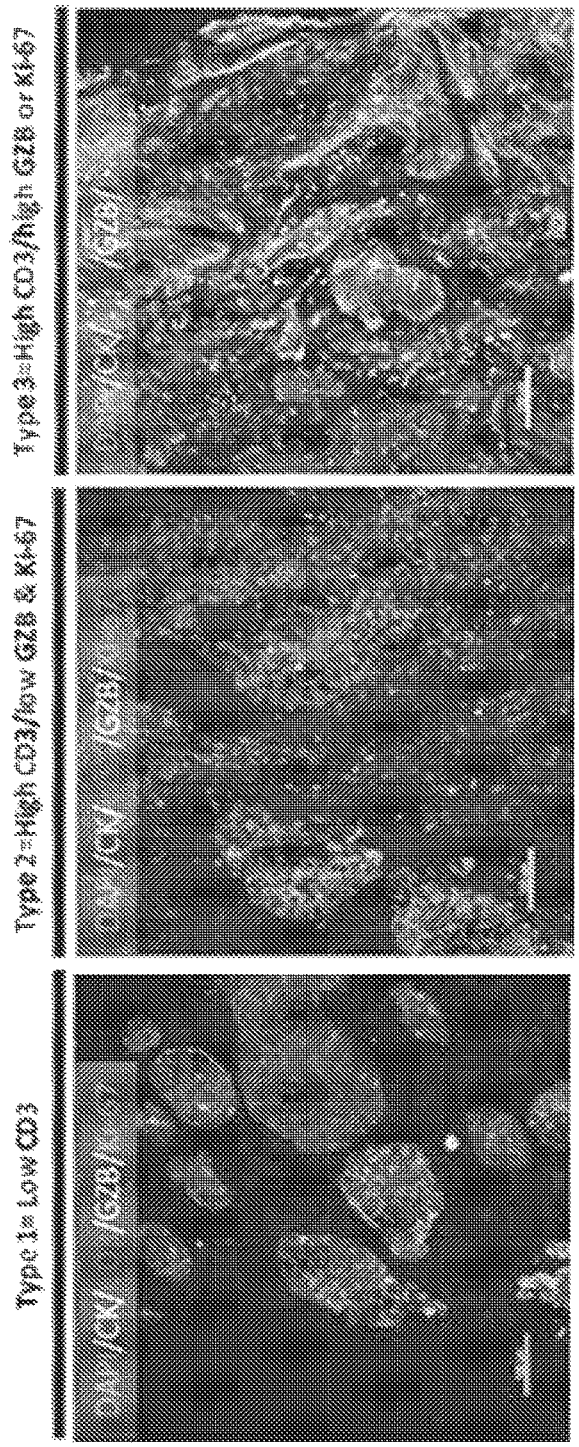
Figure 8F:
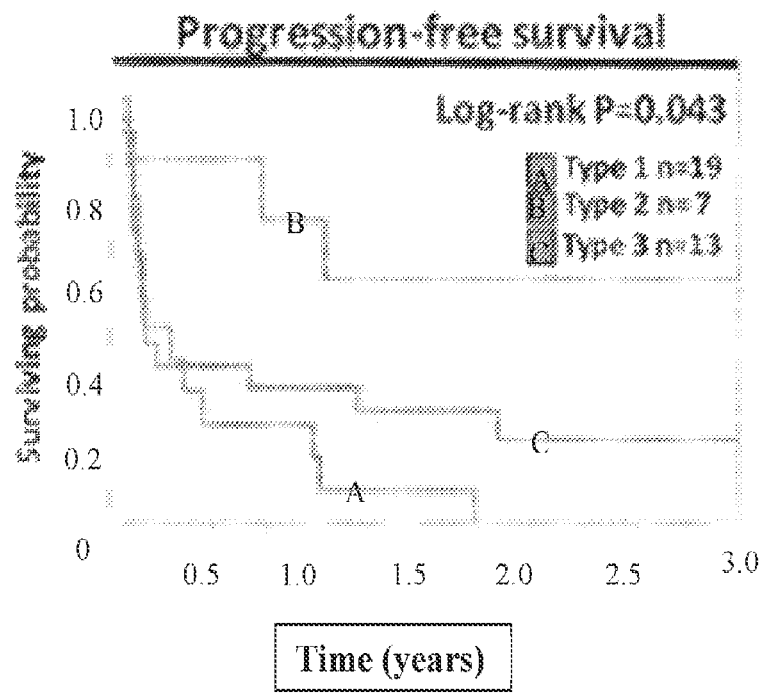
Figure 8G:
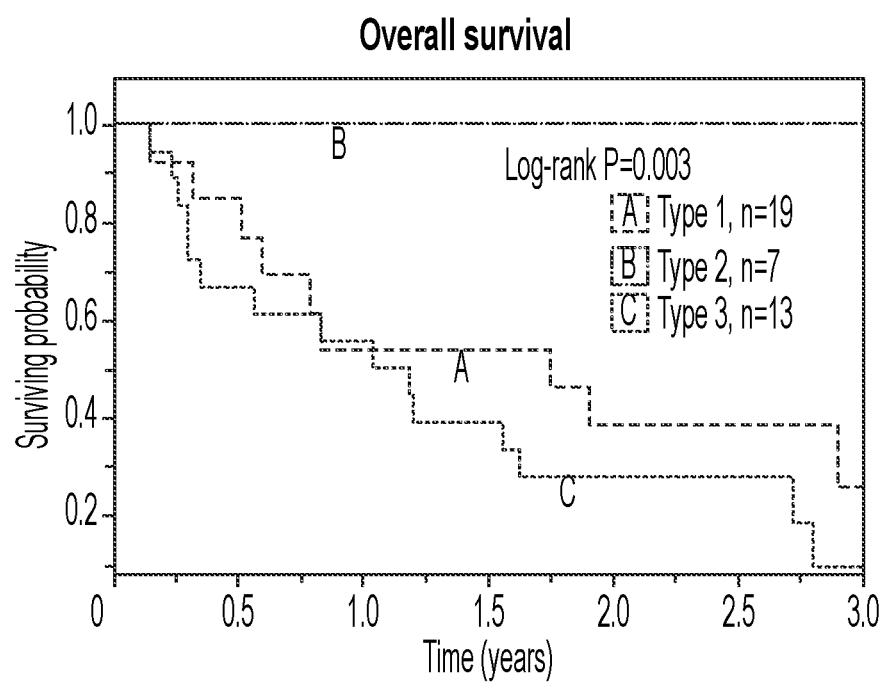

However, stratification of the cases into three groups based on their median CD3, T-cell GZB and T-cell Ki-67 levels (FIGS. 8E-G) identified tumors with a "dormant TIL phenotype" (or Type 2) pattern characterized by elevated CD3 but low T-cell GZB/Ki-67 as the one with the highest response (86% of cases with DCB), progression free (FIG. 8F) and overall survival benefit (FIG. 8G) (log-rank P=0.043 and P=0.003, respectively). Representative multicolor fluorescence pictures of the tumors showing the 3 distinct QIF-based TIL patterns are shown in FIG. 8E. A limited survival benefit was seen in tumors with low T-cell infiltration (Type 1) and those with elevated T-lymphocytes and marked in situ activation/proliferation (e.g. Type 3).

Figure 9B:
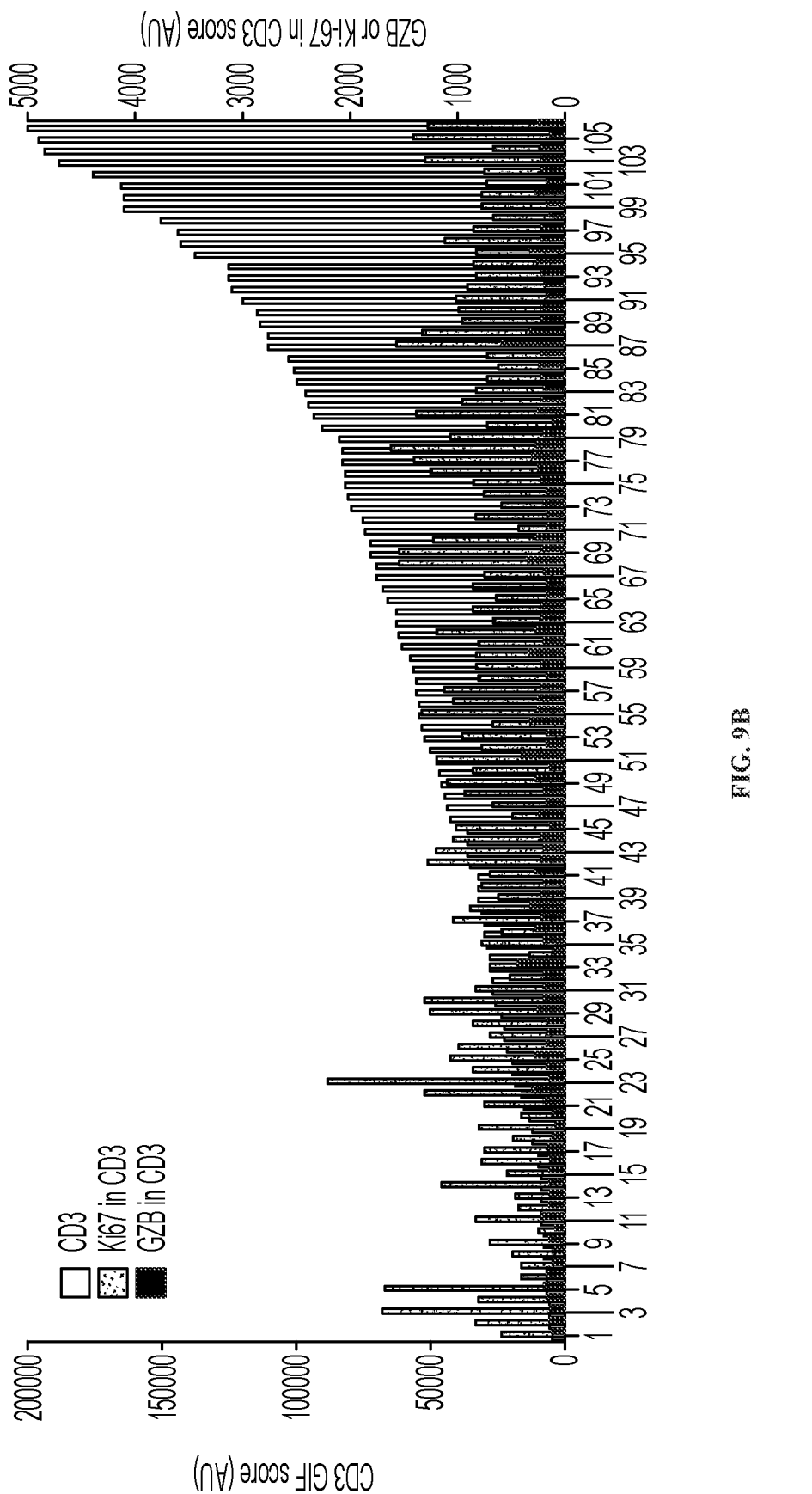
Figures 9C, 9D:
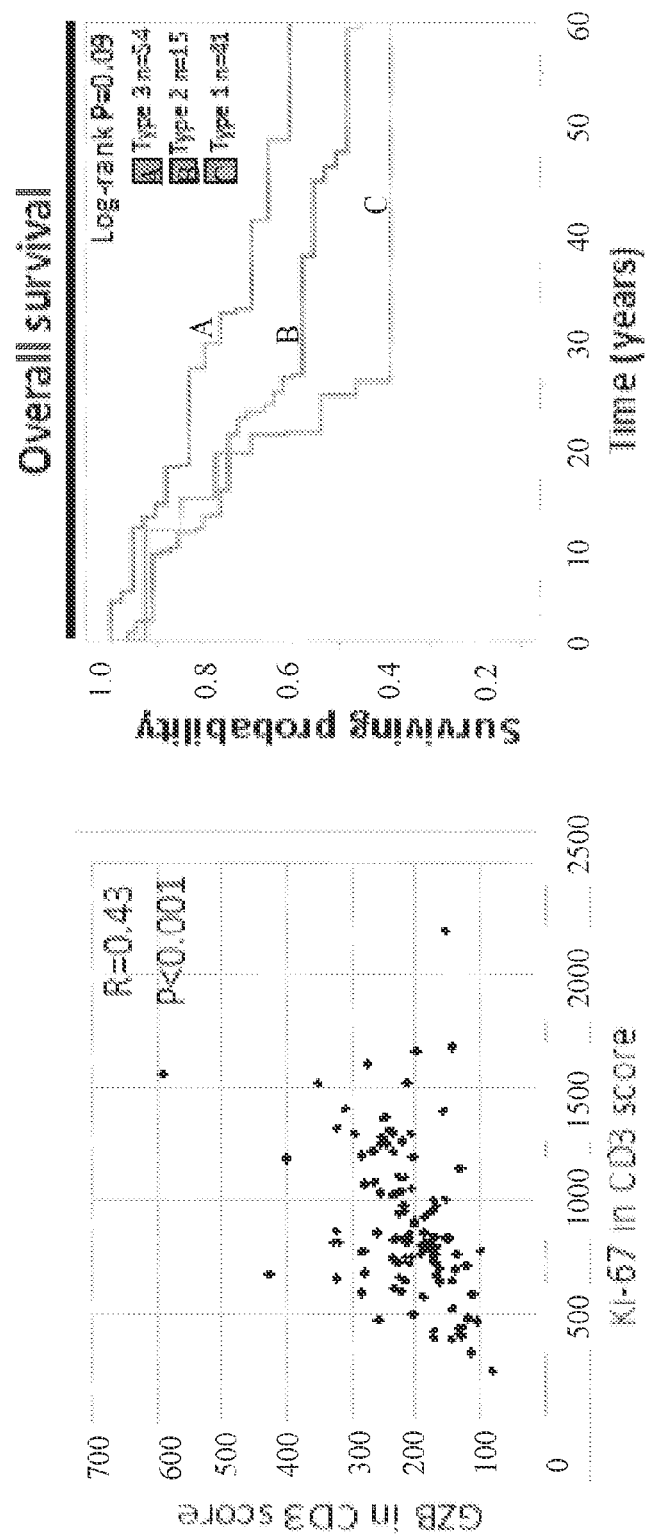

To assess the specificity of the association between the QIF-based TIL signatures and treatment with immune checkpoint blockers, the levels of T-cell infiltration, activation and proliferation in a retrospective collection of 110 stage I-IV NSCLCs not treated with immunotherapy and represented in tissue microarray format were measured (FIG. 9). Similar to the treated cases, the level of CD3+ cells in lung tumors was variable and not directly associated with the markers of T-cell activity/proliferation (FIG. 9B). There was a moderate positive association between the levels of T-cell GZB and Ki-67 (Spearman's R=0.43, FIG. 9C). However, in this population the group with the "dormant" TIL phenotype (Type 2) was not associated with survival benefit, supporting the notion that the presence of inactive TILs is associated with better outcome only in patients treated with immune checkpoint blockers. Notably, the group with a Type 3 TIL profile displaying elevated CD3+ TILs and high lymphocyte GZB and Ki-67 showed a clear trend toward better survival in this population (Log-rank P=0.09, FIG. 9D).

Figure 10B:
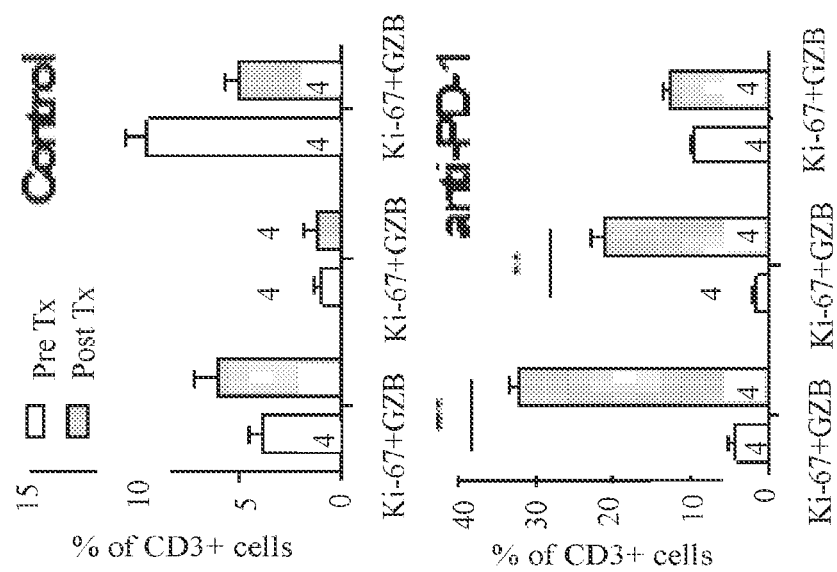
FIGS. 10A-10C depict T-cell reinvigoration with PD-1 blocking antibodies. A surgically resected primary non-small cell lung cancer was engrafted subcutaneously in the flank of NOD-scid IL2rgc−/− mice. Mice were treated intraperitoneally with anti-hPD-1 mAbs (anti-PD-1) or PBS (Control) at days 5 and 10. At day 12 mice were sacrificed and tumor tissues were mechanically digested and single cells studied by mass cytometry.
Figure 10A:
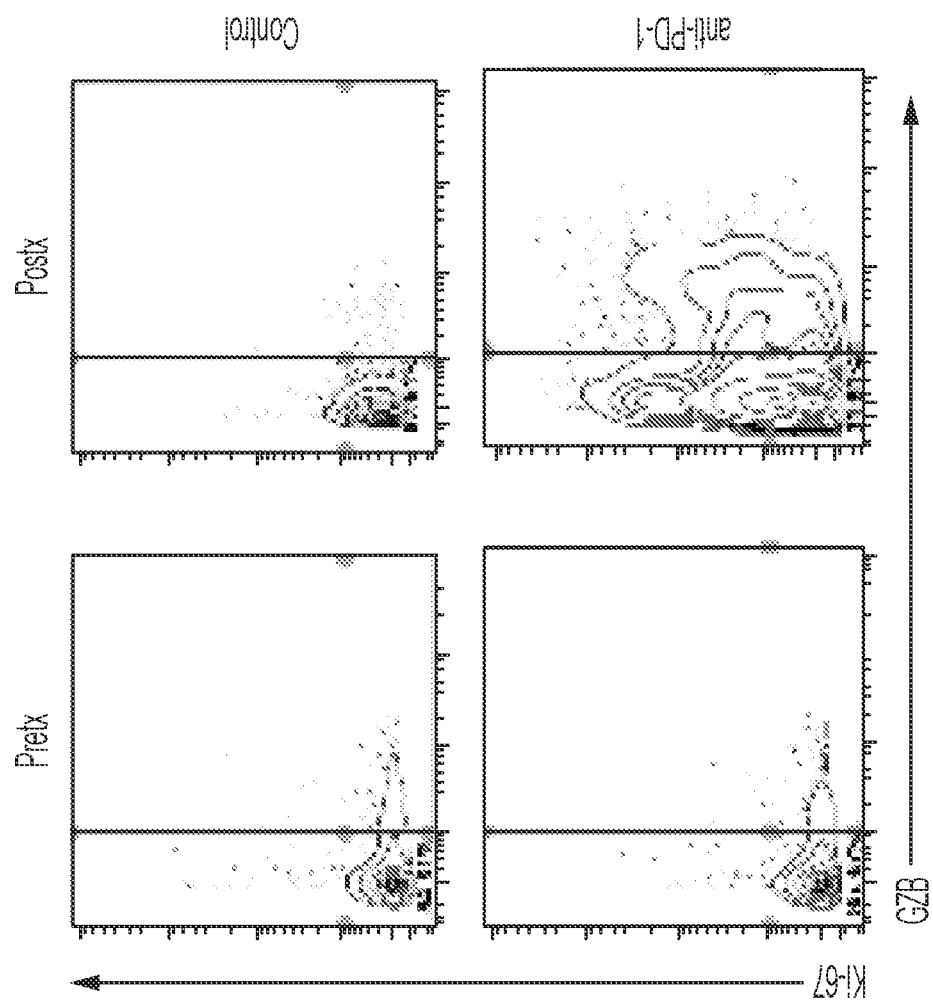
Figure 10C:
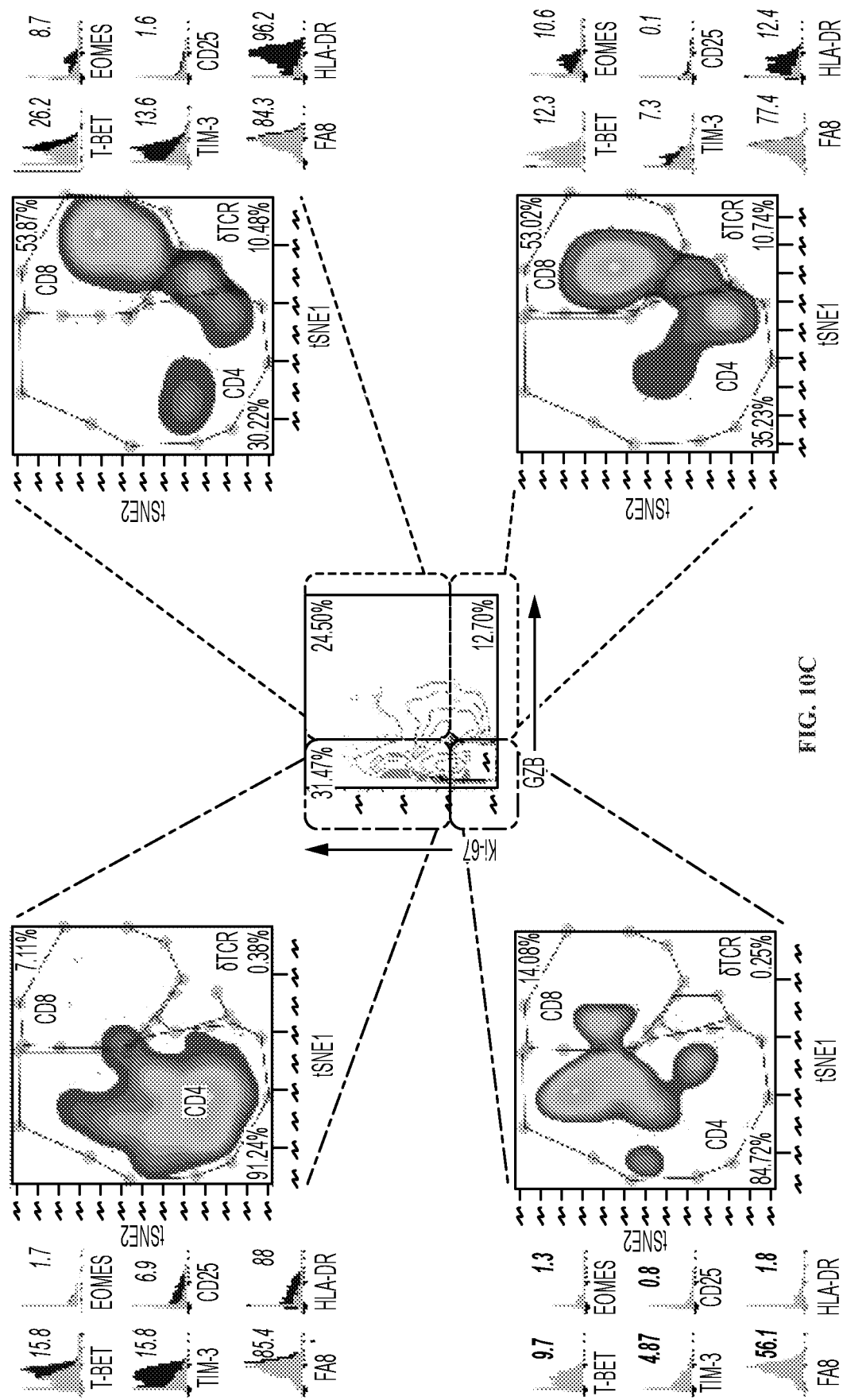

Example 6: Treatment with PD-1 Blocking Antibodies can Reinvigorate Dormant TILs To experimentally demonstrate the cytolytic activation/proliferation of "dormant" TILs upon PD-1 axis blockade, surgically resected primary lung cancer explants were engrafted subcutaneously in immune deficient mice and anti-PD-1 monoclonal antibodies were administered intravenously. Because no tumor passage in mice was performed, these surgical lung cancer explants contain tumor and also original patient-derived TILs. After treatment, cells were isolated from the resected tumor specimens and analyzed using mass cytometry. As shown in FIGS. 10A-B, human CD3+ TILs displaying low basal GZB/Ki-67 prominently increased the levels of both markers in animals treated with PD-1 blockade but not in control mice. The largest difference before and after treatment was seen in T-cells expressing Ki-67 alone or Ki-67 plus GZB (FIG. 10B). Notably, Ki-67 was predominantly increased in CD4+ T-lymphocytes and GZB was higher in the CD8+ population (FIG. 10C). Further characterization of TILs after PD-1 blockade showed elevated levels of T-BET and TIM-3 in T-cells with increased proliferation and higher levels of EOMES and HLA-DR in the GZB-high subpopulation. The fraction of T-cells showing increased Ki-67 and GZB was predominantly CD8+ with relatively high levels of T-BET, EOMES, TIM-3 and HLA-DR.

Figure 11A:
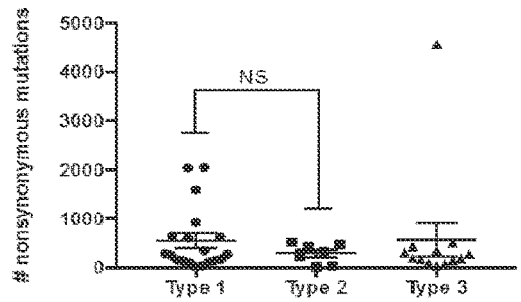
FIGS. 11A-11F depict the association between mutations and tumor immune infiltration, proliferation and cytolytic activity in NSCLC.
Figure 11B:
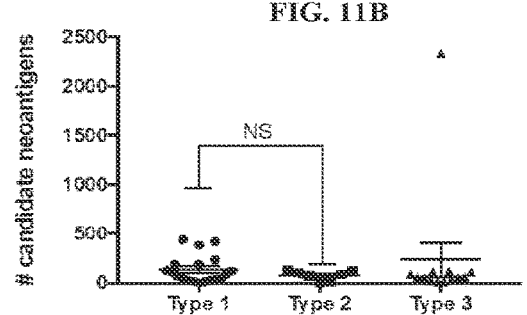
Figure 11C:
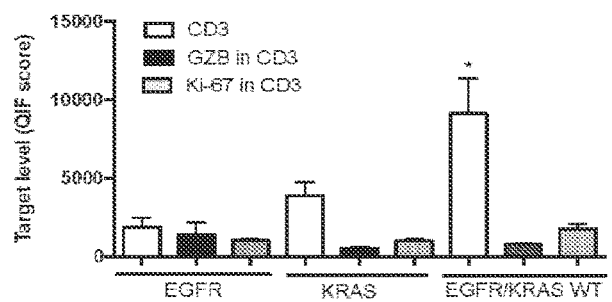
Figure 11D:
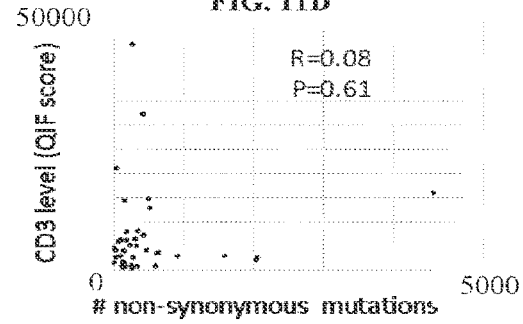
Figure 11E:
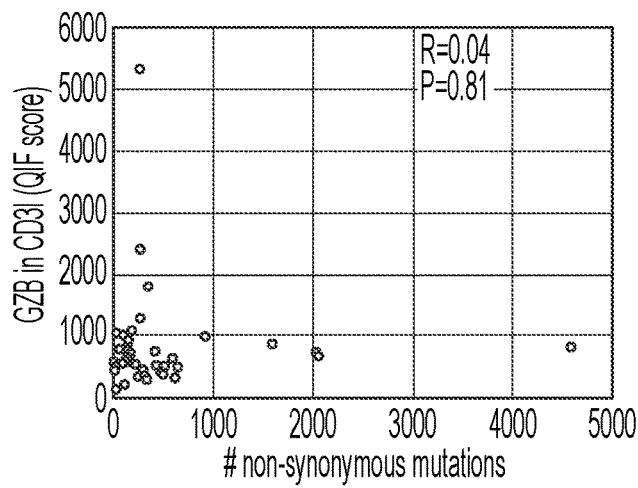
Figure 11F:
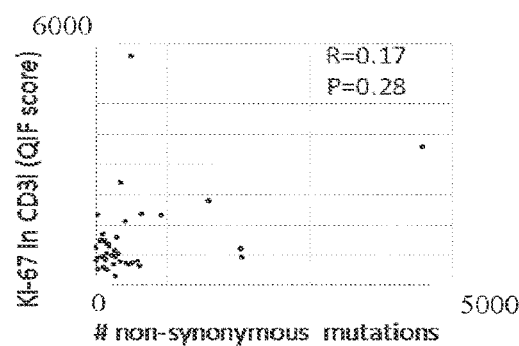
Figure 18A:
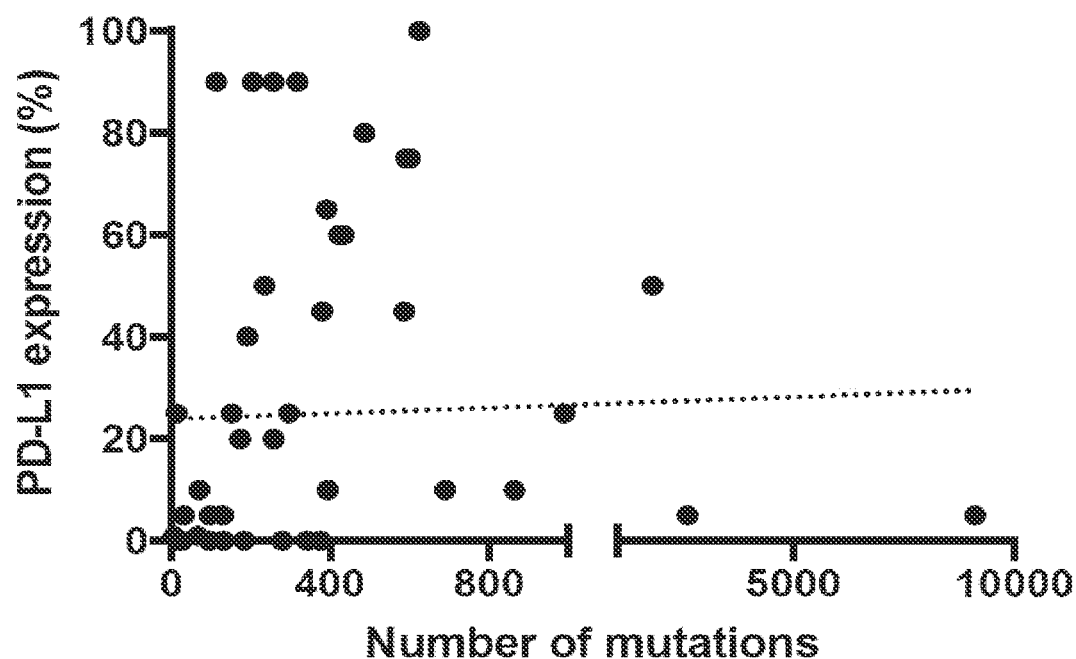
FIGS. 18A and 18B depict the association between the mutational load and PD-L1 expression (FIG. 18A), and TILs subgroups and PD-L1 expression in NSCLC (FIG. 18B).
Figure 18B:
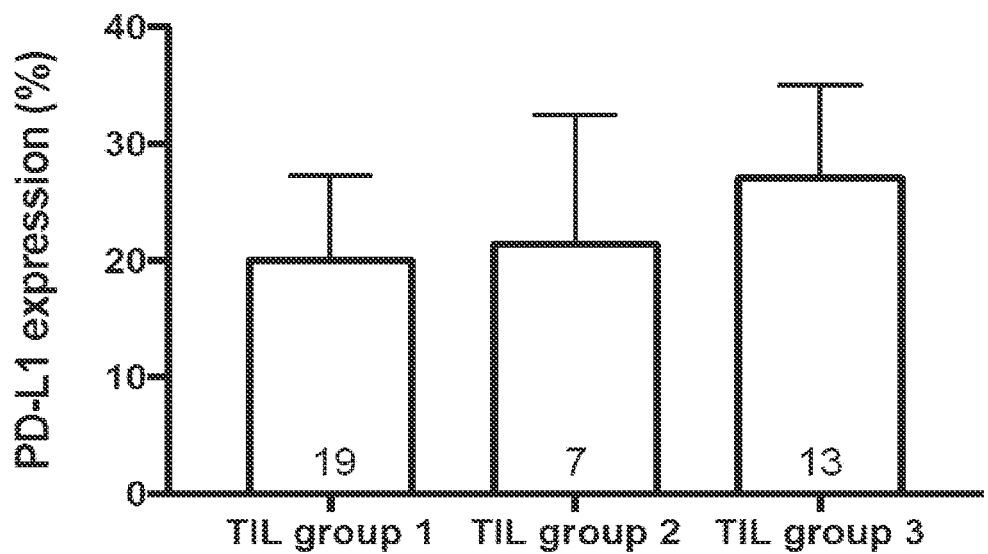

Example 7: Association Between the Genomic Landscape, PD-L1 Expression and T-Cell Metrics in NSCLC Notably, the level of somatic mutations and predicted class-I neoantigens were not significantly different across the three TIL NSCLC subtypes and the majority of cases with very high mutational load or candidate neoantigens displayed a type 1 pattern (FIGS. 11A-B). EGFR mutant cases showed significantly lower levels of T-cell infiltration than tumors lacking EGFR and KRAS mutations (P=0.03, FIG. 11C). KRAS mutant tumors showed approximately 2-fold higher CD3 signal than those with EGFR mutations, but this difference was not statistically significant. The level of GZB and Ki-67 in T-cells was not different across major molecular variants of NSCLC. There was a low association between the nonsynonymous mutational load and the level of T-cell infiltration, T-cell activation and proliferation (Spearman's R=0.04-0.17, FIGS. 11D-F). Consistent with this, the effect of the mutational load and the TIL groups were independently associated with overall survival in a multivariate Cox proportional hazard model (not shown). As shown in FIG. 18, the mutational burden (FIG. 18A) and the TIL subtypes (FIG. 18B) were not associated with the levels of tumor PD-L1 protein measured by immunohistochemistry.

Figure 19A:
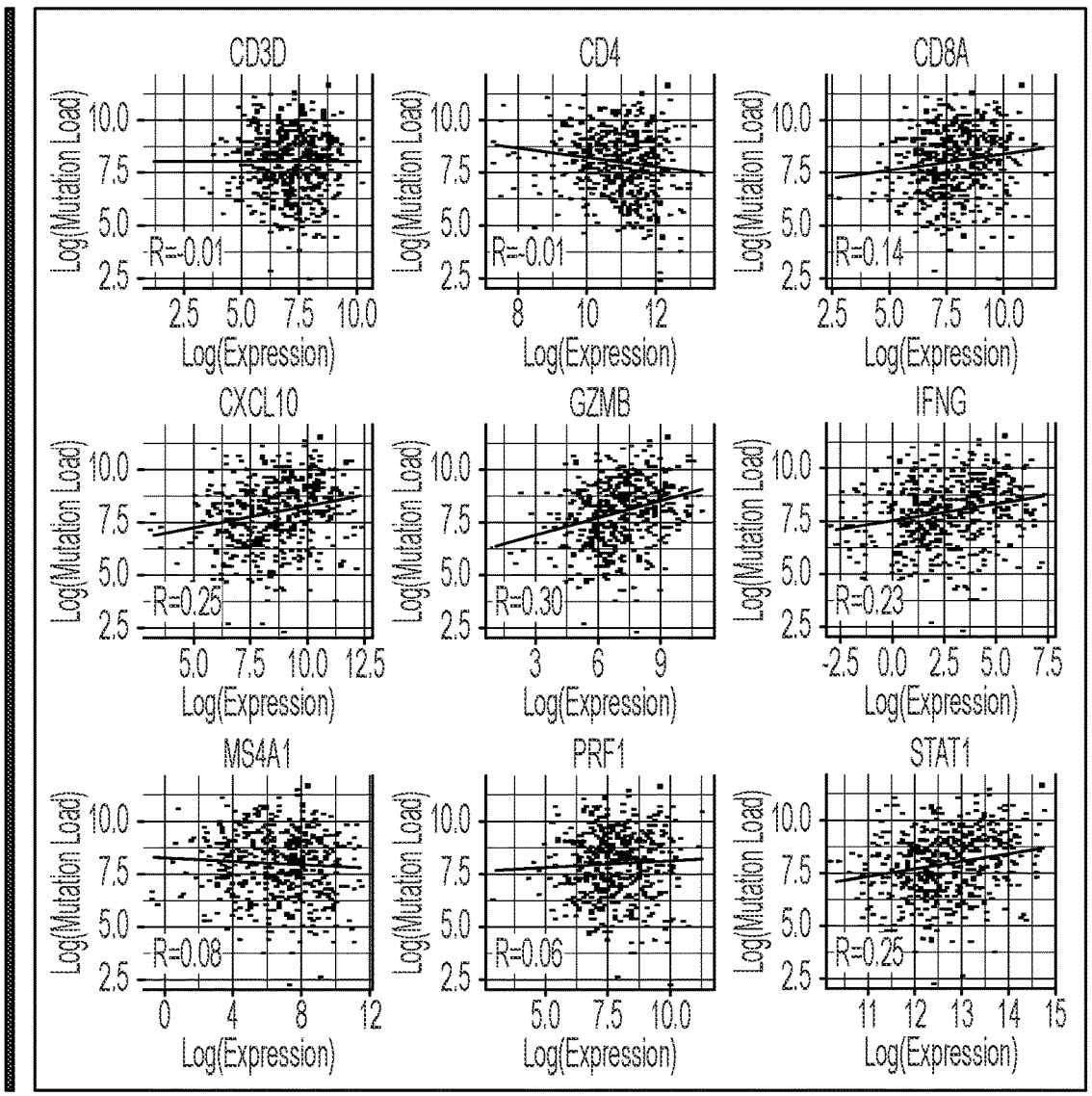
FIGS. 19A and 19B depict the association between the mutational load and expression of diverse immune-related transcripts in adenocarcinoma (FIG. 19A) and squamous carcinoma (FIG. 19B) NSCLC cases from TCGA.
Figure 19B:
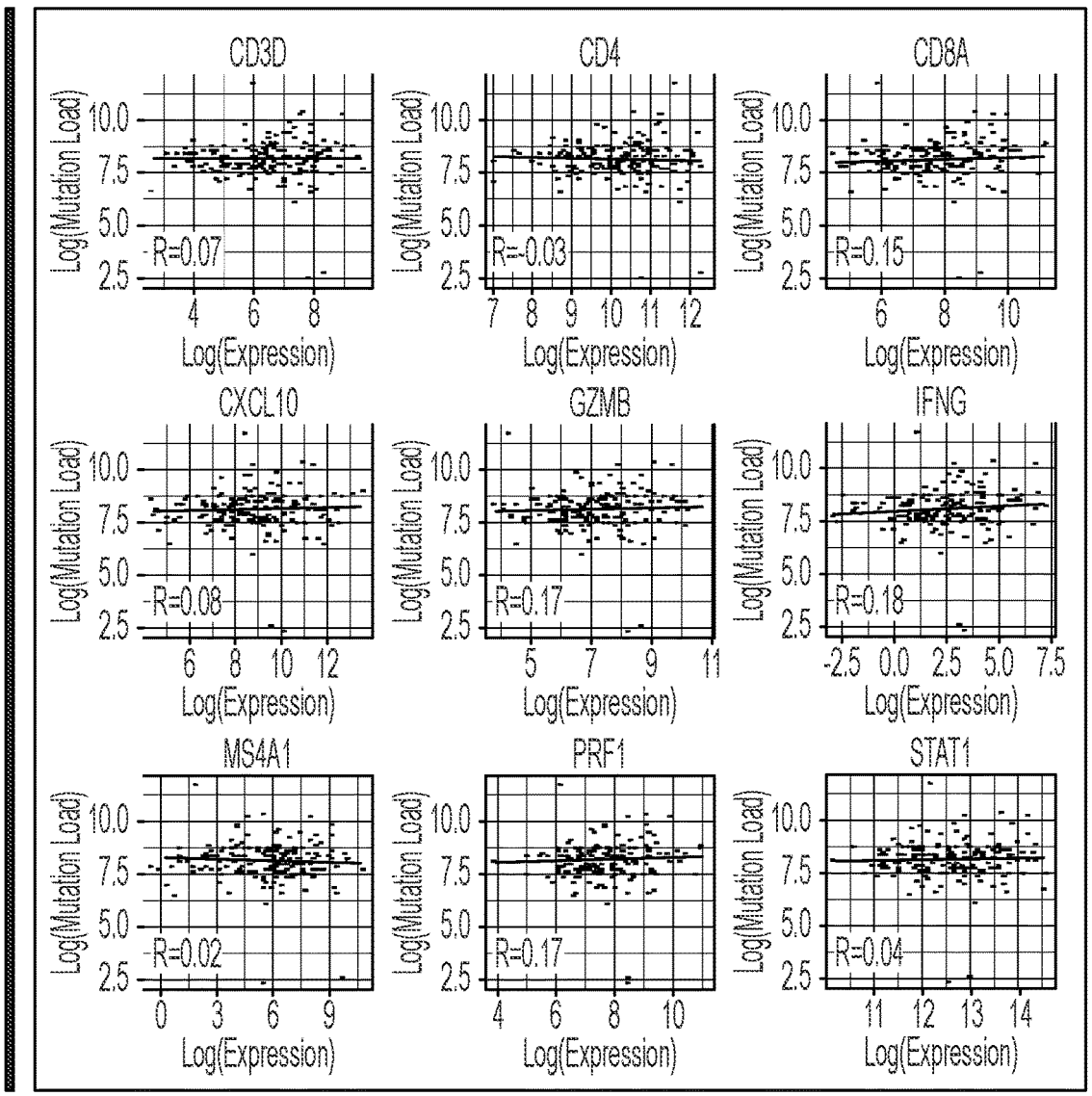
Figure 20E:
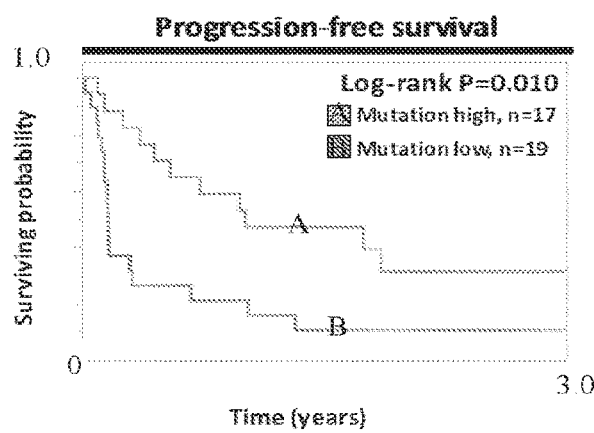
Figure 20F:
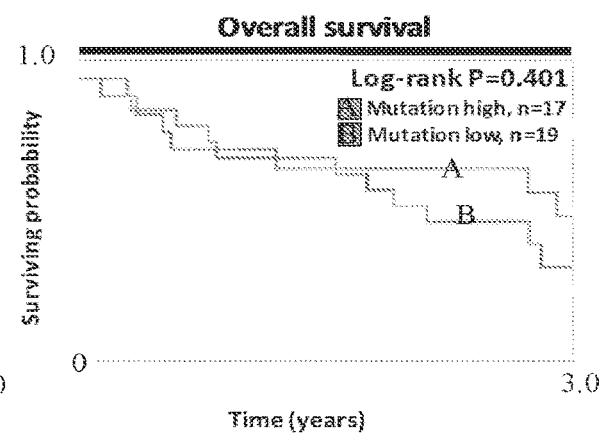

To further explore the association between the mutational load and tumor inflammation, the NSCLC cases from the TCGA collection were analyzed. As shown in FIG. 19, the mutational load was only marginally correlated with the level of adaptive immunity transcripts in lung adenocarcinomas including CD8A, CXCL10, GZMB, IFNG and STAT1 (Spearman's R=0.14-0.3) and there was no relationship with other TIL markers such as CD3, CD4, PRF1 and MS4A1 (R=−0.08-0.006, FIG. 19A). Consistent with previous observations, there was no association between the mutational load and the adaptive immunity markers in lung squamous cell carcinomas (R=−0.03-0.18, FIG. 19B).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating cancer comprising:
   a) measuring a level of at least one marker for T-lymphocytes, a level of at least one marker for proliferation in the T-lymphocytes and a level of at least one marker for activation in the T-lymphocytes in a pre-treatment tumor tissue sample from a patient,
   b) comparing the level of the marker for T-lymphocytes, the level of the marker for activation and the level of the marker for proliferation to corresponding predetermined reference levels,
   c) treating the patient with at least one immune checkpoint blocker when the level of the marker for T-lymphocytes is above the corresponding reference level, when the level of the marker for activation is below the corresponding reference level and when the level of the marker for proliferation is below the corresponding reference level.

2. The method of claim 1 wherein the marker for T-lymphocytes is CD3, CD8, CD4 or CD45RO.

3. The method of claim 1 wherein the marker for activation is granzyme-B, granzyme-A or perforin.

4. The method of claim 1 wherein the marker for proliferation is ki-67, PCNA or a Cyclin or modified cyclin.

5. The method of claim 1 wherein the level of the markers is measured using quantitative immunofluorescence or quantitative in situ assessment by heavy metal tags, nucleic acid tags or bar-codes.

6. The method of claim 1 wherein the tumor tissue is a formalin-fixed paraffin embedded sample from a conventional biopsy.

7. The method of claim 1 wherein the cancer is blastoma, carcinoma, lymphoma, melanoma, myeloma, sarcoma or germ cell tumor.

8. The method of claim 7 wherein the cancer is non-small cell lung cancer or melanoma.

9. The method of claim 1 wherein the immune checkpoint blocker comprises a PD-1 inhibitor or a CTLA4 inhibitor.

10. The method of claim 9 wherein the PD-1 inhibitor is atezolizumab, avelumab, durvalumab, nivolumab or pembrolizumab.

11. The method of claim 9 wherein the CTLA4 inhibitor is ipilimumab or tremilumimab.

12. A method of selecting patients for treatment with immune checkpoint blockers comprising:
    a) measuring a level of at least one marker for T-lymphocytes, a level of at least one marker for proliferation in the T-lymphocytes and a level of at least one marker for activation in the T-lymphocytes in a pre-treatment tumor tissue sample from a patient,
    b) comparing the level of the marker for T-lymphocytes, the level of the marker for activation and the level of the marker for proliferation to corresponding predetermined reference levels,
    c) treating the patient with at least one immune checkpoint blocker when the level of the marker for T-lymphocytes is above the corresponding reference level, when the level of the marker for activation is below the corresponding reference level and when the level of the marker for proliferation is below the corresponding reference level.

13. The method of claim 12 wherein the marker for T-lymphocytes is CD3, CD8, CD4 or CD45RO.

14. The method of claim 12 wherein the marker for activation is granzyme-B, granzyme-A or perforin.

15. The method of claim 12 wherein the marker for proliferation is ki-67, PCNA or a cyclin or modified cyclin.

16. The method of claim 12 wherein the level of the markers is measured using quantitative immunofluorescence or quantitative in situ assessment by heavy metal tags, nucleic acid tags or bar-codes.

17. The method of claim 12 wherein the tumor tissue is a formalin-fixed paraffin embedded sample from a conventional biopsy.

18. The method of claim 12 wherein the cancer is blastoma, carcinoma, lymphoma, melanoma, myeloma, sarcoma or germ cell tumor.

19. The method of claim 18 wherein the cancer is non-small cell lung cancer or melanoma.

20. The method of claim 12 wherein the immune checkpoint blocker comprises a PD-1 inhibitor or a CTLA4 inhibitor.

21. The method of claim 20 wherein the PD-1 inhibitor is atezolizumab, avelumab, durvalumab, nivolumab or pembrolizumab.

22. The method of claim 20 wherein the CTLA4 inhibitor is ipilimumab or tremilumimab.

* * * * *